US012544551B2

(12) United States Patent
Takiguchi et al.

(10) Patent No.: US 12,544,551 B2
(45) Date of Patent: Feb. 10, 2026

(54) URINARY CATHETER CAP

(71) Applicant: OTSUKA TECHNO CORPORATION, Naruto (JP)

(72) Inventors: Osamu Takiguchi, Naruto (JP); Tetsuya Masuda, Naruto (JP); Takashi Hisamoto, Naruto (JP)

(73) Assignee: OTSUKA TECHNO CORPORATION, Naruto (JP)

( * ) Notice: Subject to any disclaimer, the term of this patent is extended or adjusted under 35 U.S.C. 154(b) by 433 days.

(21) Appl. No.: 17/920,168

(22) PCT Filed: Dec. 25, 2020

(86) PCT No.: PCT/JP2020/048769
§ 371 (c)(1),
(2) Date: Oct. 20, 2022

(87) PCT Pub. No.: WO2021/215052
PCT Pub. Date: Oct. 28, 2021

(65) Prior Publication Data

US 2023/0173246 A1 Jun. 8, 2023

(30) Foreign Application Priority Data

Apr. 23, 2020 (JP) ................................ 2020-076920

(51) Int. Cl.
*A61M 39/20* (2006.01)
*A61M 25/00* (2006.01)
*A61M 39/10* (2006.01)

(52) U.S. Cl.
CPC ........ *A61M 39/20* (2013.01); *A61M 25/0017* (2013.01); *A61M 39/10* (2013.01)

(58) Field of Classification Search
CPC ........... A61M 39/20; A61M 2039/205; A61M 2205/7536; A61M 39/10;
(Continued)

(56) References Cited

U.S. PATENT DOCUMENTS 3,598,124 A * 8/1971 Andersen ................ A61F 5/441
604/129
3,952,902 A * 4/1976 Prouty ................. B65D 47/148
215/308
(Continued)

FOREIGN PATENT DOCUMENTS

CN 203107819 U * 8/2013
CN 203694250 U * 7/2014
(Continued)

OTHER PUBLICATIONS

International Search Report (PCT/ISA/210) issued in PCT/JP2020/048769 mailed on Mar. 9, 2021.
(Continued)

*Primary Examiner* — Adam Marcetich
(74) *Attorney, Agent, or Firm* — Birch, Stewart, Kolasch & Birch, LLP

(57) ABSTRACT

A urinary catheter cap includes a main body that includes a urine introduction passage including a connection hole configured to be connected to a urinary catheter and a drain hole for draining urine, a lid portion that has a tubularly formed portion having a first end portion at the drain hole side and a second end portion at an opposite side and opens and closes the drain hole, a partition portion that divides the tubular portion of the lid portion into a plurality of spaces, and a hydrophobic film that is formed such that the hydrophobic film blocks at least two or more of the spaces at the second end portion of the lid portion. The partition portion may include a partitioning plate that is installed between a plurality of locations of an inner circumferential portion of the tubular portion of the lid portion.

29 Claims, 46 Drawing Sheets

(58) Field of Classification Search

CPC .......... A61M 2039/1077; A61M 5/385; A61M 25/0017; A61M 2005/3123; A61M 25/002; A61M 5/36; A61M 2005/1403; A61M 2005/1623; A61M 2210/1085; A61M 16/0816; A61F 5/441; A61F 5/4405; A61B 5/150213; A61B 5/150351; A61B 10/007; A61B 5/150221

See application file for complete search history.

(56) References Cited

U.S. PATENT DOCUMENTS

| | | | | | |
|---|---|---|---|---|---|
| 4,262,668 | A * | 4/1981 | Schmidt | A61M 5/16809 | 604/249 |
| 4,685,472 | A * | 8/1987 | Muto | A61M 1/79 | 210/451 |
| 4,934,545 | A * | 6/1990 | Pezzoli | A61J 1/1406 | 215/250 |
| 5,045,096 | A * | 9/1991 | Quang | A61M 5/36 | 96/155 |
| 5,125,415 | A * | 6/1992 | Bell | A61B 5/150213 | 604/199 |
| 5,290,253 | A * | 3/1994 | Kira | A61M 39/20 | 604/190 |
| 5,417,678 | A * | 5/1995 | Baumann | A61F 5/441 | 604/333 |
| 5,429,620 | A | 7/1995 | Davis | | |
| 5,728,080 | A * | 3/1998 | Suyama | A61F 5/441 | 604/333 |
| 5,817,067 | A | 10/1998 | Tsukada | | |
| 5,855,230 | A * | 1/1999 | Guala | A61M 39/20 | 604/905 |
| 5,957,822 | A * | 9/1999 | Bienhaus | B65D 39/16 | 493/100 |
| 5,958,778 | A * | 9/1999 | Kidd | F26B 5/06 | 436/178 |
| 6,007,525 | A * | 12/1999 | Martell | A61F 5/441 | 604/335 |
| 9,220,866 | B2 | 12/2015 | Van Groningen et al. | | |
| 10,449,328 | B2 | 10/2019 | Tanghoej et al. | | |
| 2002/0121195 | A1* | 9/2002 | Hirayama | B01D 19/0031 | 96/219 |
| 2005/0203460 | A1* | 9/2005 | Kim | A61M 39/20 | 604/126 |
| 2006/0071007 | A1* | 4/2006 | Tsutsumi | B65D 41/14 | 220/254.1 |
| 2006/0111667 | A1* | 5/2006 | Matsuura | A61B 5/15003 | 604/93.01 |
| 2007/0161949 | A1 | 7/2007 | Knox et al. | | |
| 2008/0097315 | A1* | 4/2008 | Miner | A61M 5/1411 | 604/122 |
| 2010/0030181 | A1* | 2/2010 | Helle | A61M 5/162 | 604/411 |
| 2010/0076397 | A1* | 3/2010 | Reed | A61M 5/162 | 604/411 |
| 2011/0212294 | A1* | 9/2011 | Kato | A61M 39/10 | 156/290 |
| 2011/0276010 | A1* | 11/2011 | Davis | A61M 39/20 | 604/257 |
| 2013/0060137 | A1 | 3/2013 | Uber, III et al. | | |
| 2013/0171030 | A1* | 7/2013 | Ferlic | A61M 39/20 | 422/294 |
| 2013/0267896 | A1* | 10/2013 | Dogwiler | B01D 53/22 | 96/6 |
| 2014/0174578 | A1* | 6/2014 | Bonnal | A61M 39/26 | 137/798 |
| 2014/0235960 | A1 | 8/2014 | Addington et al. | | |
| 2015/0320926 | A1* | 11/2015 | Fitzpatrick | A61M 1/3666 | 604/244 |
| 2016/0030293 | A1* | 2/2016 | Dorsey | A61M 5/347 | 604/122 |
| 2016/0279347 | A1* | 9/2016 | Staley | A61M 5/385 | |
| 2016/0339226 | A1* | 11/2016 | Sealfon | A61M 39/1011 | |
| 2017/0341402 | A1* | 11/2017 | Nagashima | B65D 47/06 | |
| 2018/0303655 | A1* | 10/2018 | Glithero | A61L 29/146 | |
| 2019/0329173 | A1* | 10/2019 | Mao | A61M 39/20 | |
| 2019/0343445 | A1* | 11/2019 | Burnett | A61B 5/207 | |
| 2020/0338227 | A1* | 10/2020 | Majhi | A61L 15/46 | |
| 2021/0370020 | A1* | 12/2021 | Gupta | A61M 39/0693 | |

FOREIGN PATENT DOCUMENTS

| | | | | |
|---|---|---|---|---|
| CN | 103990226 | A * | 8/2014 | |
| CN | 104606739 | A * | 5/2015 | A61M 39/20 |
| DE | 3147499 | A1 * | 6/1983 | |
| DE | 29505787 | U1 * | 7/1995 | |
| EP | 0081655 | A1 * | 6/1983 | |
| EP | 0 781 572 | A2 | 7/1997 | |
| JP | 58-51737 | U | 4/1983 | |
| JP | 62-655 | Y2 | 1/1987 | |
| JP | 9-206370 | A | 8/1997 | |
| JP | 2002-17865 | A | 1/2002 | |
| JP | 2004-236999 | A | 8/2004 | |
| JP | 3781803 | B2 | 5/2006 | |
| JP | 5318925 | B2 | 10/2013 | |
| JP | 2014-212873 | A | 11/2014 | |
| JP | 2015-532876 | A | 11/2015 | |
| JP | 5804675 | B2 | 11/2015 | |
| JP | 6163198 | B2 | 7/2017 | |
| JP | 2019-50941 | A | 4/2019 | |
| JP | 3224825 | U * | 1/2020 | |
| WO | WO 2015/075841 | A1 | 5/2015 | |

OTHER PUBLICATIONS

Written Opinion (PCT/ISA/237) issued in PCT/JP2020/048769 mailed on Mar. 9, 2021.

Extended European Search Report for European Application No. 20932778.2, dated Apr. 30, 2024.

* cited by examiner

A4

A9

A10

A10

A5

A5

URINARY CATHETER CAP

TECHNICAL FIELD

The present invention relates to a urinary catheter cap.

BACKGROUND ART

A urinary catheter is conventionally known as a medical device for aiding withdrawing of urine from a patient with difficulty in urination. For example, Patent Literature 1 discloses a urinary catheter that includes a catheter main body with a rod shape, a balloon portion formed at one end portion of the catheter main body, and an operating portion formed at another end portion of the catheter main body.

Also, as a component that controls overflow of urine from a catheter, Patent Literature 2 discloses a cap of self-catheterization catheter that includes an end nozzle with which a lower end portion of a tubular body is formed to a spherical surface, a housing that is provided with a notch and a lumen and slidably houses the lower end portion, and a base connector of the tubular body.

CITATION LIST

Patent Literature

Patent Literature 1: Japanese Patent No. 5318925

Patent Literature 2: Japanese Patent Application Publication No. 2004-236999

SUMMARY OF INVENTION

Technical Problem

A cap for catheter such as that of Patent Literature 2 is useful for controlling overflow of urine from a catheter but has several problems.

For example, with clean intermittent catheterization (CIC), unless a tip of a catheter is directed properly toward a toilet bowl or urinal, urine drained from the catheter may splash to a surrounding of the toilet bowl, etc. Thus, splashing can be prevented by closing a lid of the cap until urine is drained and opening the lid only after directing the tip of the catheter toward the toilet bowl, etc., accurately. However, in a state where the lid of the cap is closed and the catheter is sealed, urine cannot flow to the tip of the catheter, whether or not the catheter has reached an interior of a bladder thus cannot be confirmed, and it is thus difficult to ascertain the timing for opening the cap with the tip of the catheter being directed toward the toilet bowl, etc.

On the other hand, in indwelling catheterization using a catheter such as that of Patent Literature 1, positioning of a balloon for retention is important. As a method, for example, the catheter is inserted into a urethra and when it is confirmed that the bladder interior is reached and excretion of urine has started, the catheter is inserted slightly further and the balloon is inflated to set the position. The reason why the balloon is not inflated at the point at which the start of excretion of urine is confirmed is because there are cases where even when a tip of the catheter has reached the bladder interior, the balloon is positioned inside the urethra and there is a possibility of damaging the urethra if the balloon is inflated in this state. However, as in clean intermittent catheterization (CIC), it cannot be confirmed whether or not the catheter has reached the bladder interior in the state where the lid of the cap is closed and the catheter is sealed. Although the catheter may thus be inserted into the urethra with the lid of the cap being opened, urine that has begun to be excreted cannot be stopped by the cap in this case. Therefore, there is a possibility of becoming flustered by overflow of urine from the cap and inserting the catheter excessively to position the balloon. Consequently, when the bladder contracts during retention of the catheter, the tip of the catheter may contact the bladder wall and damage the bladder wall.

An object of the present invention is thus to provide a urinary catheter cap that can improve usability of a catheter when performing self-catheterization.

Also, another object of the present invention is to provide a urinary catheter cap that can prevent splashing of urine drained from a catheter when performing clean intermittent catheterization (CIC).

Yet another object of the present invention is to provide a urinary catheter cap by which a position of a balloon of catheter can be set appropriately when performing indwelling catheterization.

Solution to Problem

A urinary catheter cap according to a preferred embodiment of the present invention includes a main body that includes a urine introduction passage including a connection hole configured to be connected to a urinary catheter and a drain hole for draining urine, a lid portion that opens and closes the drain hole, an open hole that is formed in the main body or the lid portion and faces the urine introduction passage, and a hydrophobic film that is formed such that the hydrophobic film blocks the open hole.

According to this arrangement, the hydrophobic film is formed on the open hole of the cap. Air inside the urinary catheter can thereby be released to the exterior when inserting the catheter into the urethra and therefore, urine inside a bladder can be guided smoothly to the cap after a tip of the catheter reaches the bladder. On the other hand, urine that is drained from the bladder is obstructed by the hydrophobic film and the urine can thus be retained in the urine introduction passage of the cap. Consequently, a subsequent task can be performed slowly without haste upon confirming that the urine has reached the cap.

For example, in performing clean intermittent catheterization (CIC), splashing of urine can be prevented by confirming the arrival of urine and then opening the lid portion of the cap toward a toilet bowl, etc. On the other hand, in performing indwelling catheterization, positioning of a balloon can be performed satisfactorily because the catheter can be inserted calmly to an appropriate position upon confirming the arrival of urine.

Further, although after self-catheterization is ended, the urinary catheter is disinfected by being placed in a case containing a disinfectant solution, the cap of the present invention is such that even when it remains attached to the urinary catheter, the disinfectant solution can be supplied throughout an interior of the urinary catheter. Consequently, the urinary catheter can be kept sanitary.

With the urinary catheter cap according to the preferred embodiment of the present invention, the open hole may be formed in the lid portion.

With the urinary catheter cap according to the preferred embodiment of the present invention, the lid portion may be openably and closably coupled to the main body via a hinge mechanism and the lid portion may have a plug portion with a tubular shape that is inserted into the drain hole and has the open hole formed therein.

According to this arrangement, the lid portion is coupled to the main body via the hinge mechanism and it is therefore unnecessary to perform positioning of the lid portion with respect to the drain hole when closing the lid portion. Also, the portion that blocks the drain hole is a plug portion and therefore the drain hole can be blocked easily by pressing the lid portion into the drain hole.

With the urinary catheter cap according to the preferred embodiment of the present invention, the lid portion may include a lid portion of a screw type that is detachable from the main body.

According to this arrangement, the main body and the lid portion are screwed together by the lid portion of the screw type and therefore, the drain hole can be blocked securely.

With the urinary catheter cap according to the preferred embodiment of the present invention, the open hole may be formed such that the open hole is connected to an intermediate portion of the urine introduction passage of the main body in a flow direction of urine.

If the urinary catheter cap according to the preferred embodiment of the present invention further includes a film placement portion that is formed projectingly from a side wall of the main body, the hydrophobic film may be disposed at the film placement portion.

With the urinary catheter cap according to the preferred embodiment of the present invention, the lid portion may include a duckbill valve that has a pair of inclining valve elements that extend such as to converge toward the connection hole from an end portion of the drain hole.

According to this arrangement, for example, a urine collection bag, etc., can be inserted directly into the cap.

With the urinary catheter cap according to the preferred embodiment of the present invention, the lid portion may include a lid portion with a stick shape that has a plug portion that is inserted into the drain hole and a columnar portion that is coupled to the plug portion.

According to this arrangement, since the lid portion has a stick shape, the lid portion can be opened easily with one hand, for example, by pushing a side surface of the lid portion with a thumb.

With the urinary catheter cap according to the preferred embodiment of the present invention, the film placement portion may include a supporting body that projects from a side wall of the main body and a film placement plate that is formed to a flange shape with respect to the supporting body and has a first engaging portion at a circumferential edge portion and on which the hydrophobic film is disposed and the lid portion may include a second engaging portion that engages with the first engaging portion of the film placement plate from an outer surface side of the film placement plate.

According to this arrangement, engagement of the first engaging portion and the second engaging portion can be released and the lid portion can be opened by pushing the film placement plate. The lid portion can be opened without touching it directly and therefore, wetting of a hand with urine during opening of the lid portion can be prevented reliably.

With the urinary catheter cap according to the preferred embodiment of the present invention, the main body may be formed of a material that contains a substance with antibacterial action.

According to this arrangement, the cap can be kept sanitary because the main body is formed of the material that contains the substance with antibacterial action. Also, by containing the substance with antibacterial action, an amount of ammonia generated from urea when urine reaches the cap can be reduced and therefore, odor of urine can be alleviated.

With the urinary catheter cap according to the preferred embodiment of the present invention, the drain hole may have a curved shape with which a diameter increases as an open end of the drain hole is approached.

According to this arrangement, draining off of urine from an edge of the drain hole after discarding of urine can be improved and therefore a task of wiping the edge of the drain hole after draining of urine can be omitted.

With the urinary catheter cap according to the preferred embodiment of the present invention, the main body may be formed of a translucent material that contains a substance having a function of generating color by action of water.

According to this arrangement, a color of the main body changes when urine reaches the cap and therefore, the arrival of urine can be easily confirmed visually.

With the urinary catheter cap according to the preferred embodiment of the present invention, an embossment may be formed on an inner surface of the urine introduction passage of the main body.

According to this arrangement, a reflection state of light at the main body changes when urine reaches the cap and therefore, the arrival of urine can be easily confirmed visually.

The urinary catheter cap according to the preferred embodiment of the present invention may further include a detecting means that detects arrival of urine at the urine introduction passage and a transmitting means that transmits arrival information of urine based on detection by the detecting means.

According to this arrangement, various information can be obtained in accordance with the type of the transmitting means. For example, if the transmitting means is a sound generating means, the arrival of urine can be easily confirmed aurally, and if the transmitting means is a vibrating means, the arrival of urine can be easily confirmed by skin sensation. Also, if the transmitting means is a wireless transmitting means, a medical staff or a patient him/herself can indirectly obtain objective information on whether or not the catheter is inserted correctly.

The urinary catheter cap according to the preferred embodiment of the present invention may further include a second lid portion that is openably and closably mounted to the main body or the lid portion and covers the hydrophobic film airtightly.

According to this arrangement, by closing the second lid portion, the odor of the urine that reaches the cap can be prevented from leaking out to the exterior via the hydrophobic film. On the other hand, since the second lid portion is openable and closeable, shutoff of air that flows to the exterior via the hydrophobic film can be avoided by keeping the second lid portion open until the urine reaches the cap.

With the urinary catheter cap according to the preferred embodiment of the present invention, the hydrophobic film may be formed of a material that contains an ammonia degrading enzyme.

According to this arrangement, the odor of the urine that reaches the cap can be alleviated because the ammonia in the urine can be degraded by the urine contacting the hydrophobic film.

With the urinary catheter cap according to the preferred embodiment of the present invention, the hydrophobic film may contain an acidic agent.

According to this arrangement, the odor of the urine that reaches the cap can be alleviated because the ammonia in the urine can be neutralized with the acidic agent by the urine contacting the hydrophobic film.

A urinary catheter cap according to a preferred embodiment of the present invention includes a main body that includes a urine introduction passage including a connection hole configured to be connected to a urinary catheter and a drain hole for draining urine, a lid portion that has a tubularly formed portion having a first end portion at the drain hole side and a second end portion at an opposite side and opens and closes the drain hole, a partition portion that divides the tubular portion of the lid portion into a plurality of spaces, and a hydrophobic film that is formed such that the hydrophobic film blocks at least two or more of the spaces at the second end portion of the lid portion.

According to this arrangement, the hydrophobic film is formed at the lid portion. Air inside the urinary catheter can thereby be released to the exterior when inserting the catheter into the urethra and therefore, urine inside a bladder can be guided smoothly to the cap after a tip of the catheter reaches the bladder. On the other hand, urine that is drained from the bladder is obstructed by the hydrophobic film and the urine can thus be retained in the urine introduction passage of the cap. Consequently, a subsequent task can be performed slowly without haste upon confirming that the urine has reached the cap.

Also, the lid portion is divided into a plurality of spaces and each of the spaces is blocked by the hydrophobic film. Thereby, even if, for example, a disinfectant solution that remains inside the catheter after disinfection flows down into the cap, flowing in of the disinfectant solution into all spaces can be avoided, for example, by tilting the cap obliquely. Consequently, clogging of the hydrophobic film can be avoided in one or some of the spaces and therefore, air permeability of the hydrophobic film can be secured satisfactorily even after disinfection.

With the urinary catheter cap according to the preferred embodiment of the present invention, the partition portion may include a partitioning plate that is installed between a plurality of locations of an inner circumferential portion of the tubular portion of the lid portion.

According to this arrangement, volumes of the respective spaces can be secured such as to be comparatively large. Therefore, even if the disinfectant solution flows into the spaces, influence of surface tension of the disinfectant solution inside the spaces can be reduced. Consequently, the disinfectant solution inside the spaces can be eliminated quickly.

With the urinary catheter cap according to the preferred embodiment of the present invention, the lid portion may include a cover member that is formed at the second end portion of the tubular portion of the lid portion such that the cover member covers the hydrophobic film and the cover member may have a projecting portion that projects outward from a side wall thereof.

According to this arrangement, the projecting portion for opening and closing of the lid portion can be separated from an opening/closing position of the lid portion of the cap. Contact of urine with a hand can thus be avoided when opening the lid portion to drain the urine.

With the urinary catheter cap according to the preferred embodiment of the present invention, the projecting portion may include a flange portion with an annular shape that is formed across an entire outer circumference of the cover member.

With the urinary catheter cap according to the preferred embodiment of the present invention, the cover member may include a top wall portion that covers the hydrophobic film and has an upper surface constituted of a plain surface without holes formed therein and a flow port that secures flow of air inside and outside the cover member in a lateral direction along the upper surface of the top wall portion may be formed in a side wall of the cover member.

According to this arrangement, the upper surface of the top wall portion is completely closed and therefore, even if, for example, water contacts the cap during cleaning of the catheter, contact of water and the hydrophobic film can be prevented. The hydrophobic film can thereby be protected from water pressure.

With the urinary catheter cap according to the preferred embodiment of the present invention, the hydrophobic film may have a thickness of 10 μm to 2 mm and its air permeation (Gurley value) measured in conformance to JIS P 8117 (Gurley method) may be 0.1 seconds to 500 seconds/100 mL and its water pressure resistance measured in conformance to JIS L 1092-B (high water pressure method) may be not less than 0.1 kPa.

According to this arrangement, water repellency, air permeability, pressure resistance, and long-term water repellency of the hydrophobic film can be maintained even when the cap is used over a long term.

DESCRIPTION OF EMBODIMENTS

Preferred embodiments of the present invention shall now be described in detail with reference to the attached drawings.

[Overall Arrangement of Catheter 1]

Figure 1:
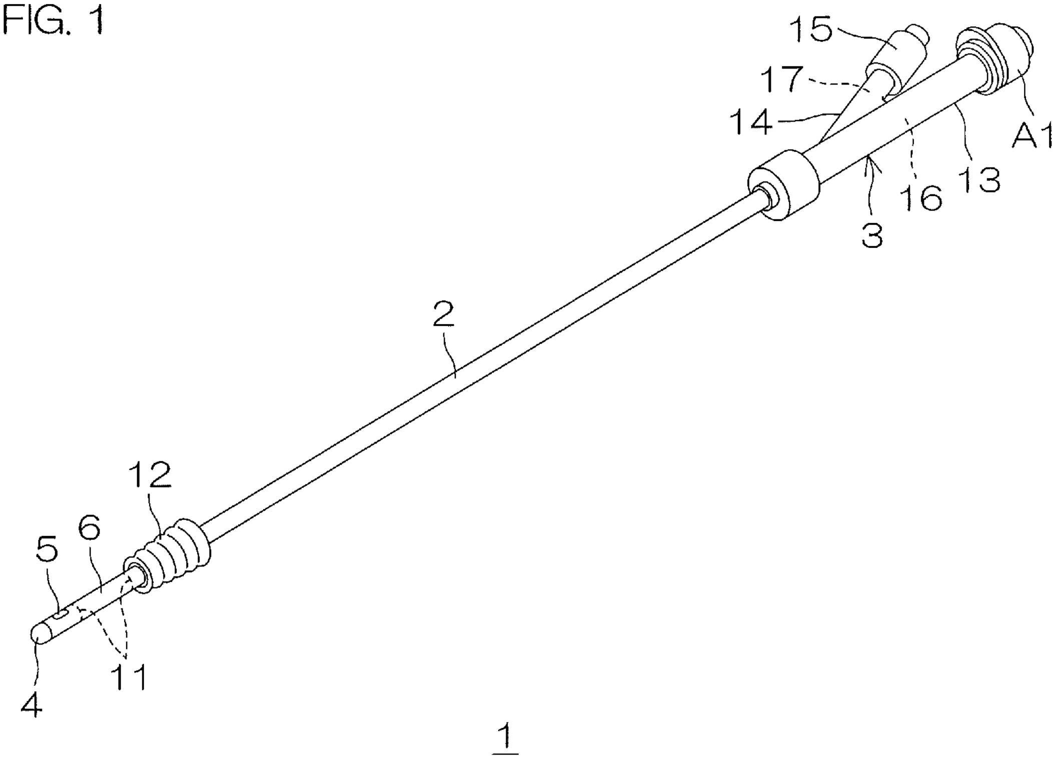
FIG. 1 is a perspective view of a catheter mounted with a cap according to a first preferred embodiment of the present invention.
Figure 2A:
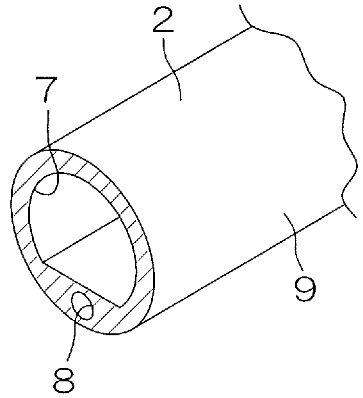
FIG. 2A and FIG. 2B are diagrams for describing a cross-sectional structure of a shaft of FIG. 1.
Figure 2B:
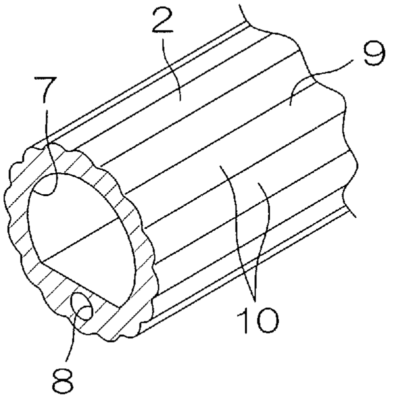

FIG. 1 is a schematic perspective view of a catheter 1 mounted with a cap A1 according to a first preferred embodiment of the present invention. FIG. 2A and FIG. 2B are diagrams for describing a cross-sectional structure of a shaft 2 of FIG. 1. Here, FIG. 1 shows a state where a balloon 6 of the catheter 1 is uninflated.

The catheter 1 is a medical device (urinary catheter), for example, for aiding withdrawing of urine from a patient with difficulty in urination and includes the shaft 2 and a base 3.

The shaft 2 is constituted, for example, of a flexible tube and a cap 4 made of hard material is mounted to a tip thereof. For example, the shaft 2 is inserted into the cap 4 to arrange a spigot structure and mating surfaces of the spigot structure are welded or adhered, etc., to affix the two together.

The shaft 2 and the cap 4 may each be arranged, for example, by applying a surface treatment to a base member of a rubber latex base material such as a natural rubber latex, a synthetic rubber latex, etc., a silicone base material, a thermoplastic elastomer, etc. As the surface treatment, for example, hydrophilic coating that imparts lubricity to the base member, urethane coating or fluorine coating that imparts smoothness to the base member, silver coating that imparts an antibacterial property to the base member, etc., can be cited. Two or more types of these surface treatments may be used in combination.

A side hole 5 and the balloon 6 are formed at the tip of the shaft 2. As shown in FIG. 2A and FIG. 2B, a urine withdrawing lumen 7 and a balloon lumen 8 that are in communication with the side hole 5 and the balloon 6, respectively, are formed in an interior of the shaft 2. Also, a circumferential surface 9 of the shaft 2 may be a smooth surface such as shown in FIG. 2A or may be an uneven surface such as shown in FIG. 2B. In the arrangement of FIG. 2B, the circumferential surface 9 of the shaft 2 is formed as the uneven surface by a plurality of ribs 10 (projecting ridges) that extend in a length direction of the shaft 2. By the ribs 10, friction during insertion of the catheter 1 into a urethra or extraction of the catheter 1 from the urethra can be lessened and therefore, discomfort of a patient can be eased.

In this preferred embodiment, the balloon 6 may be formed integral to the shaft 2. In other words, a connection portion does not have to be formed between the balloon 6 and the shaft 2 (here, in FIG. 1, vague boundaries 11 between the balloon 6 and the shaft 2 is represented by broken lines). A surface of the balloon 6 and a surface (circumferential surface 9) of the shaft 2 can thereby be made continuous with a smooth surface. Consequently, the friction during insertion of the catheter 1 into the urethra or extraction of the catheter 1 from the urethra can be lessened and therefore, the discomfort of the patient can be eased.

Also, a sleeve 12 with a tubular shape may be fitted on the shaft 2. The sleeve 12 is mounted such as to be movable in the length direction of the shaft 2. When inserting the catheter 1 into the urethra, the catheter 1 can be inserted sanitarily by inserting while holding the shaft 2 via the sleeve 12.

The base 3 may include a urine drain base 13 and a balloon base 14. The urine drain base 13 is an outlet through which urine guided from the side hole 5 to the urine withdrawing lumen 7 is drained. On the other hand, the balloon base 14 is an injection port for sterilized water for inflating the balloon 6 and includes a check valve 15. The urine drain base 13 and the balloon base 14 are formed to tubular shapes with a urine introduction passage 16 and a water introduction passage 17 formed in interiors, respectively. Here, although in FIG. 1 the urine drain base 13 and the balloon base 14 are formed to tubular shapes of substantially fixed diameter, the urine drain base 13 and the balloon base 14 may instead be formed, for example, to funnel shapes that spread in outer diameter toward the respective open ends. In this case, the urine drain base 13 and the balloon base 14 may be referred to as a urine drain funnel and a balloon funnel, respectively.

The cap A1 for urinary catheter according to the first preferred embodiment is provided at an open end portion of the urine drain base 13. The cap A1 is detachably mounted to the urine drain base 13 by a connection portion 23 to be described later being inserted into the urine introduction passage 16 of the urine drain base 13.

First Preferred Embodiment

Figure 3:
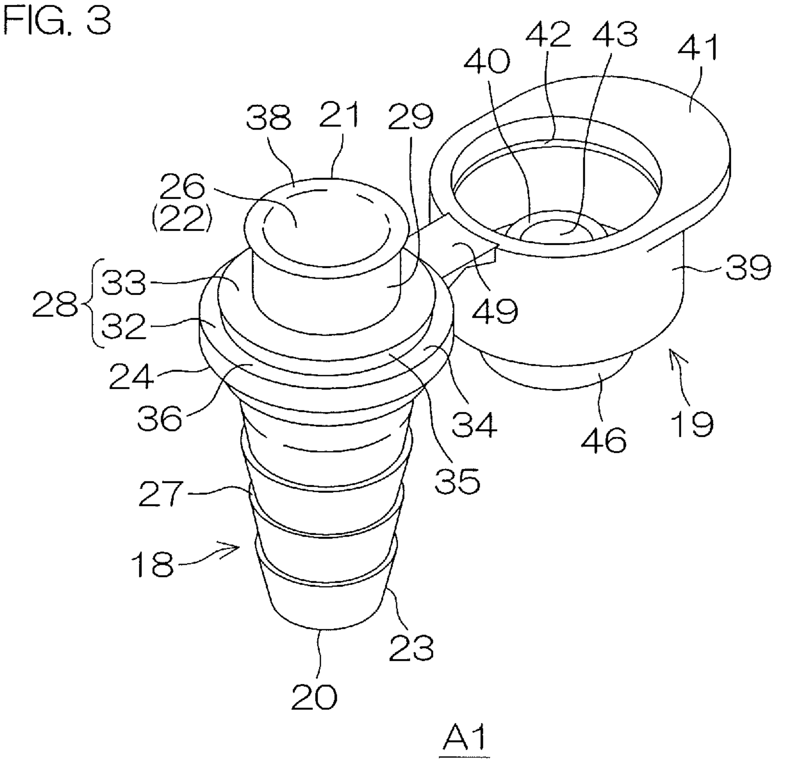
FIG. 3 is a perspective view of the cap according to the first preferred embodiment of the present invention.
Figure 4:
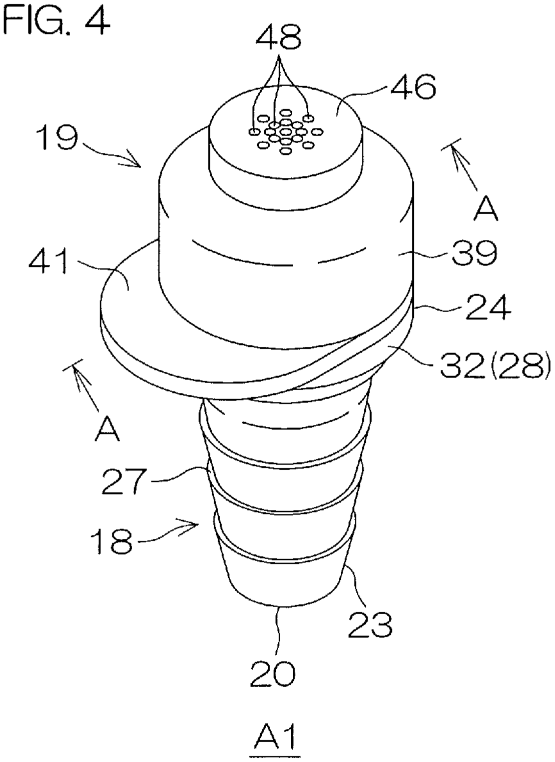
FIG. 4 is a perspective view of the cap according to the first preferred embodiment of the present invention.
Figure 5:
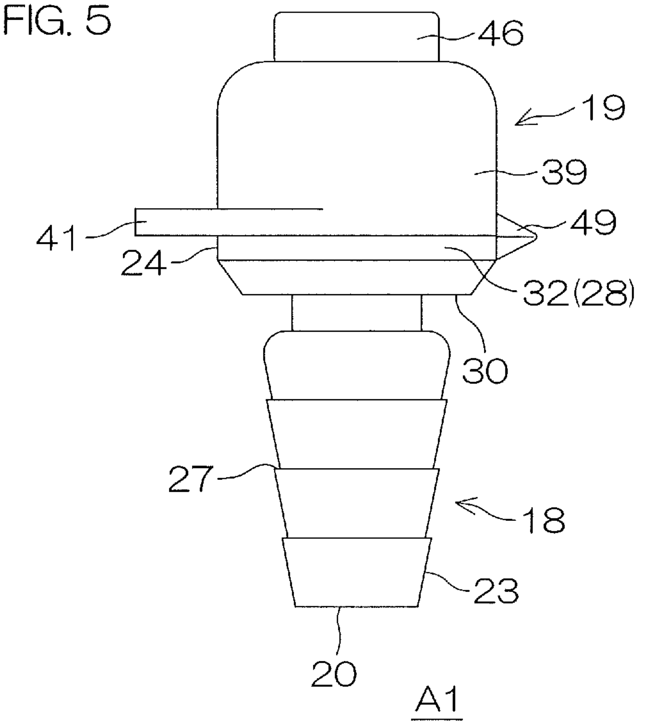
FIG. 5 is a side view of the cap according to the first preferred embodiment of the present invention.
Figure 6:
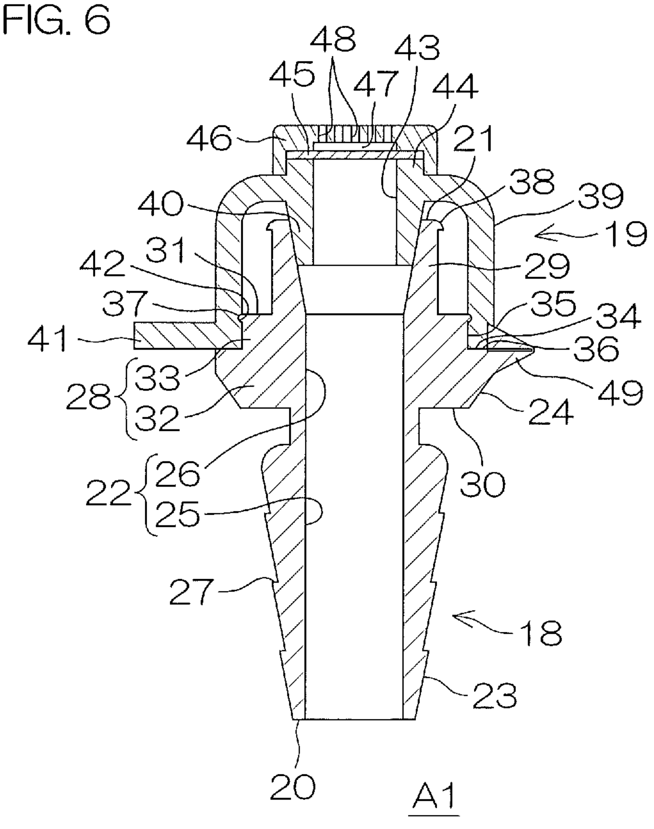
FIG. 6 is a diagram showing a section taken along A-A of FIG. 4.

FIG. 3 and FIG. 4 are perspective views of the cap A1 according to the first preferred embodiment of the present invention, with FIG. 3 showing a state where a lid portion 19 is opened and FIG. 4 showing a state where the lid portion 19 is closed. FIG. 5 is a side view of the cap A1 according to the first preferred embodiment of the present invention. FIG. 6 is a diagram showing a section taken along A-A of FIG. 4.

The cap A1 may include a main body 18 and the lid portion 19. In this preferred embodiment, the main body 18 and the lid portion 19 are formed of an integral resin and further, these may be an integral resin molded article.

The main body 18 and the lid portion 19 may be constituted, for example, of a general-purpose plastic (for example, polypropylene, polyethylene, ABS resin, polycarbonate, polyamide, etc.). Also, these general-purpose plastics may have translucency. The main body 18 and the lid portion 19 can be manufactured as a molded article by a known molding method, for example, injection molding, compression molding, 3D printer molding, etc.

Also, the main body 18 and the lid portion 19 may contain a substance with antibacterial action, a substance having a function of generating color by action of water, etc. As the substance with antibacterial action, for example, an antibacterial agent that is zeolite-based, silica gel-based, glass-based, or phosphate-based, etc., can be used. As the substance having the function of generating color by action of water, for example, Hydrochromic (registered trademark) manufactured by The Pilot Ink Co., Ltd., etc., can be used.

To make the main body 18 and the lid portion 19 contain the abovementioned substances, for example, the substance with antibacterial action and the substance having the function of generating color by action of water should be mixed by kneading into an abovementioned general-purpose plastic and the mixture should be molded.

If the main body 18 and the lid portion 19 thus contain the substance with antibacterial action, the cap A1 can be kept sanitary. Also, if the substance with antibacterial action is contained, an amount of ammonia generated from urea when urine reaches the cap A1 can be reduced and therefore, odor of urine can be alleviated. Also, if the main body 18 and the lid portion 19 contain the substance having the function of generating color by action of water, a color of the main body 18 changes when urine reaches the cap A1 and therefore, the arrival of urine can be easily confirmed visually.

The main body 18 has a first end portion 20 and a second end portion 21 and is formed to a tubular shape with a urine introduction passage 22, extending from the first end portion 20 to the second end portion 21, formed in an interior. An embossment may be formed on an inner surface of the urine introduction passage 22. The embossment may be applied to the inner surface of the urine introduction passage 22, for example, by forming a pattern corresponding to the embossment on a surface of a molding die for the cap A1. If the embossment is thus formed on the urine introduction passage 22, a reflection state of light at the main body 18 changes when urine reaches the cap A1 and therefore, the arrival of urine can be easily confirmed visually. Here, that the main body 18 contains the substance having the function of generating color by action of water and that the embossment is formed on the main body 18 may both be provided as features of the cap A1 or just one of either may be provided.

Also, in this preferred embodiment, the main body 18 may include the connection portion 23 and a drain portion 24 as external shapes. The urine introduction passage 22 may be differentiated into a connection hole 25 at the connection portion 23 side and a drain hole 26 at the drain portion 24 side. More specifically, the connection portion 23 is a portion that is connected to the urine drain base 13 of the catheter 1 and the drain portion 24 is the portion besides the connection portion 23 and is the portion from which urine is ultimately drained. Here, each of the connection portion 23 and the drain portion 24 is not required to be a functional name and, for example, the connection portion 23 may be referred to as a first portion of the main body 18 and the drain portion 24 may be referred to as a second portion of the main body 18.

The connection portion 23 may, for example, be a plug portion with a tapered shape that narrows in outer diameter toward the first end portion 20 side of the main body 18. On a circumferential surface of the connection portion 23, a plurality (three in this preferred embodiment) of step portions 27 for retention of the connection portion 23 with respect to the base 3 are formed at intervals from each other in an axial direction (direction along the urine introduction passage 22) of the connection portion 23. Each step portion 27 is formed across an entire circumference in a circumferential direction of the connection portion 23.

The drain portion 24 may include a base portion 28 with a flange shape that is connected to the connection portion 23 and a drain outlet 29 that extends from the base portion 28 to the second end portion 21 side of the main body 18.

The base portion 28 may have a first surface 30 at the connection portion 23 side and a second surface 31 at an opposite side thereto. The base portion 28 may integrally include a first portion 32 with a circular annular shape at the first surface 30 side and a second portion 33 with a circular annular shape that is formed at the second surface 31 side and has a smaller outer diameter than the first portion 32. A step portion 34 with a circular shape is thereby formed across an entire circumference in a circumferential direction of the base portion 28 between the first portion 32 and the second portion 33. The step portion 34 has a side surface 35 and a bottom surface 36 that are respectively formed of a side surface of the second portion 33 and an upper surface of the first portion 32. At an upper end of the side surface 35 of the step portion 34, a projecting ridge 37 that projects in a lateral direction from the side surface 35 is formed in a circular shape across an entire circumference in a circumferential direction of the first portion 32.

The drain outlet 29 is formed to a circular tubular shape. At an open end portion of the drain outlet 29, a curved portion 38 is formed such as to increase in outer diameter as an open end is approached. That is, an outer circumferential surface of the drain outlet 29 is a surface that is outwardly curved at the open end portion. The curved portion 38 improves draining off of urine from an edge of the drain outlet 29 and suppresses occurrence of urine drip from the drain outlet 29 when urine is drained from the drain outlet 29. A task of wiping the edge of the drain outlet 29 after the drain of urine can thereby be omitted and also, contamination of the cap A1 by urine after the drain of urine from the drain outlet 29 can be suppressed. Also, even if urine drip occurs, the urine can be retained by an upper surface of the second portion 33 (the second surface 31 of the base portion 28) because the base portion 28 is of the two-step structure of the first portion 32 and the second portion 33. Also, since the upper surface of the second portion 33 is a portion that is covered by the lid portion 19 when the lid portion 19 is closed as shown in FIG. 6, the dripped urine can be prevented from being exposed to the exterior. Also, the drain hole 26 in the drain outlet 29 has a tapered shape that narrows in diameter from an open end (the second end portion 21 of the main body 18) toward the connection portion 23.

The lid portion 19 may include a base portion 39 with an interior that is formed to a hollow, dome shape and a plug portion 40 that projects from a top portion inner surface of the base portion 39 to the interior of the base portion 39.

The base portion 39 with a dome shape may include the top portion that is an upper end portion and a base that is a lower end portion. A flange portion 41 that protrudes outward from a circumferential surface of the base portion 39 is formed on the base of the base portion 39. The flange portion 41 is formed selectively from a portion of the base of the base portion 39. The base portion 39 is thereby formed to a cap shape as a whole. In an internal side surface of the base portion 39, a recessed groove 42 is formed to a circular shape across an entire circumference in a circumferential direction of the base portion 39. The recessed groove 42 is formed to a width enabling fitting of the projecting ridge 37 described above.

The plug portion 40 is formed to a tubular shape with an open hole 43 formed therein and is formed to be shorter than a height of the base portion 39. Also, the plug portion 40 has a tapered shape that narrows in outer diameter toward a tip of the plug portion 40.

A film placement portion 44 with a circular annular shape that projects upward is formed at the top portion of the base portion 39. The open hole 43 is formed in the lid portion 19 such as to pass continuously through the film placement portion 44 and the plug portion 40. A hydrophobic film 45 is disposed on the film placement portion 44 such as to block the open hole 43.

The hydrophobic film 45 may, for example, be a porous film with an action of allowing air to pass and preventing passage of a liquid. For example, a diameter (pore diameter) of pores formed in the hydrophobic film 45 may be 0.05 μm to 50 μm. Also, a thickness of the hydrophobic film 45 may be 0.01 mm to 2 mm. Also, from a standpoint of providing an action of selectively removing a liquid inside the cap A1, the hydrophobic film 45 may be referred to as a hydrophobic filter. In this case, the film placement portion 44 may be referred to as a filter placement portion (film placement portions 61, 65, 83, and 84 and a film placement plate 67 to be described later may also be referred to as filter placement portions and a filter placement plate).

As such a hydrophobic film 45, for example, a known hydrophobic film, such as that of polytetrafluoroethylene (PTFE), acrylic copolymer, polyethersulfone (PES), glass fiber, etc., can be used.

Also, a material that forms the hydrophobic film 45 may contain an ammonia degrading enzyme. May be formed of a material that. The odor of the urine that reaches the cap A1 can thereby be alleviated because the ammonia in the urine can be degraded by the urine contacting the hydrophobic film 45.

Further, the hydrophobic film 45 may contain an acidic agent. Here, that the acidic agent is contained may mean that the hydrophobic film 45 contains the acidic agent as a component or may mean a state where the hydrophobic film 45 has the acidic agent adhered to its surface by being loaded into the acidic agent.

As the acidic agent, a known acidic agent, for example, an organic acid such as succinic acid, fumaric acid, tartaric acid, citric acid, malic acid, adipic acid, gluconic acid, lactic acid, etc., or a salt of any of these or the like can be used. The odor of the urine that reaches the cap A1 can thereby be alleviated because the ammonia in the urine can be neutralized with the acidic agent by the urine contacting the hydrophobic film 45. The acidic agent may be contained in the hydrophobic film 45 in advance or may be added to the hydrophobic film 45, for example, before the catheter 1 is inserted into the urethra.

Also, a cover member 46 is provided at the top portion of the base portion 39 such as to cover the hydrophobic film 45. The cover member 46 is formed to a bottomed circular tubular shape having a larger outer diameter than the film placement portion 44. The cover member 46 is bonded to the top portion of the base portion 39 at a circumference of the film placement portion 44 such that the hydrophobic film 45 and the film placement portion 44 are housed in its interior. The cover member 46 may be bonded to the base portion 39, for example, by heat welding, adhesive agent, etc.

Also, a recess portion 47 is formed in the cover member 46 by a portion of its bottom portion being recessed selectively. In this preferred embodiment, the recess portion 47 is formed in a central portion of the circular bottom portion of the cover member 46. Thereby, in a state where the hydrophobic film 45 is covered, a space portion corresponding to the recess portion 47 is formed between a portion of a bottom surface of the cover member 46 and the hydrophobic film 45. That is, the bottom surface of the cover member 46 selectively contacts the hydrophobic film 45 at a portion of circular annular shape at a circumference of the recess portion 47. By the forming of the space portion, air inside the catheter 1 can be vented satisfactorily.

Also, a plurality of flow ports 48 that enable flow of air in a thickness direction of the cover member 46 are formed in the cover member 46. As shown in FIG. 6, the plurality of flow ports 48 may be formed in a region facing the recess portion 47.

Also, the lid portion 19 is integrally coupled to the main body 18 via a hinge mechanism 49. In this preferred embodiment, the hinge mechanism 49 is formed of a living hinge that is constituted of the resin integral to the main body 18 and the lid portion 19. The hinge mechanism 49 is connected to the base of the base portion 39 at an opposite side to the flange portion 41.

The lid portion 19 can be closed, for example, by pinching the flange portion 41 to fold the hinge mechanism 49 and pressing the top portion of the base portion 39. By pressing the top portion of the base portion 39, the plug portion 40 is inserted into the drain hole 26 and the projecting ridge 37 and the recessed groove 42 are fitted together. Thereby, the lid portion 19 is locked with respect to the main body 18 and the drain hole 26 can be closed. In this state, the urine introduction passage 22 of the main body 18 and the open hole 43 of the lid portion 19 are in mutual communication as shown in FIG. 6.

With the cap A1, positioning of the lid portion 19 with respect to the drain hole 26 does not have to be performed in closing the lid portion 19 because the lid portion 19 is coupled to the main body 18 via the hinge mechanism 49. Also, the drain hole 26 can be blocked easily by pressing the lid portion 19 into the drain hole 26 because the portion that blocks the drain hole 26 is the plug portion 40.

Second Preferred Embodiment

Figure 7:
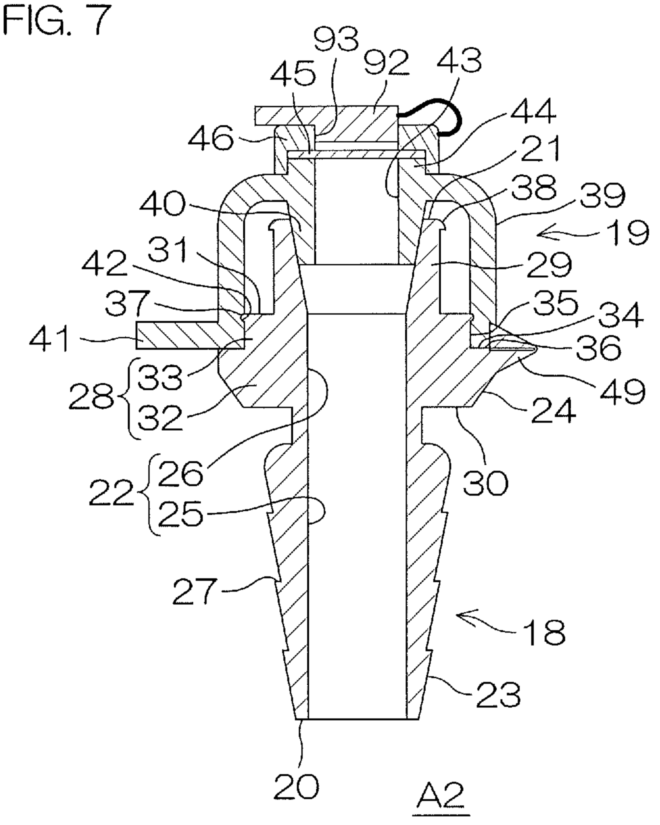
FIG. 7 is a sectional view of a cap according to a second preferred embodiment of the present invention.
Figure 8:
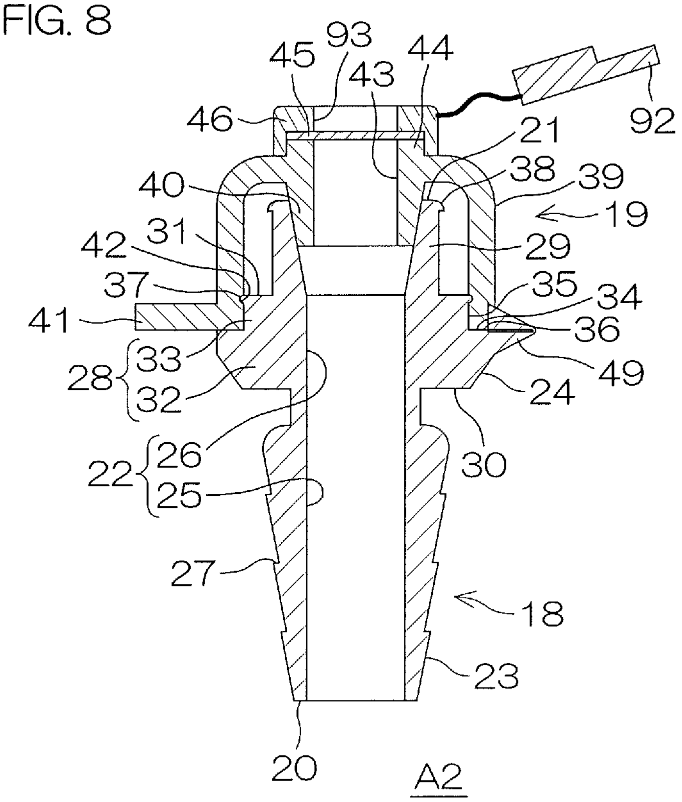
FIG. 8 is a sectional view of the cap according to the second preferred embodiment of the present invention.

FIG. 7 and FIG. 8 are sectional views of a cap A2 according to a second preferred embodiment of the present invention, with FIG. 7 showing a state where a second lid portion is closed and FIG. 8 showing a state where the second lid portion is opened. In FIG. 7 and FIG. 8, arrangements equivalent to arrangements indicated in the preferred embodiment described above shall be provided with the same reference signs and description thereof shall be omitted.

The cap A2 according to this preferred embodiment further includes the second lid portion 92 that covers the hydrophobic film 45 airtightly. More specifically, an opening 93 is formed in the cover member 46 of the lid portion 19 and the second lid portion 92 is mounted openably and closably to the cover member 46 such as to block the opening 93. In this case, the flow ports 48 may be omitted.

With the cap A2, by closing the second lid portion 92 as shown in FIG. 7, the odor of the urine that reaches the cap A2 can be prevented from leaking to the exterior via the hydrophobic film 45. On the other hand, since the second lid portion 92 is openable and closeable, shutoff of air that flows to the exterior via the hydrophobic film 45 can be avoided by keeping the second lid portion 92 open as shown in FIG. 8 until the urine reaches the cap A2.

Third Preferred Embodiment

Figure 9:
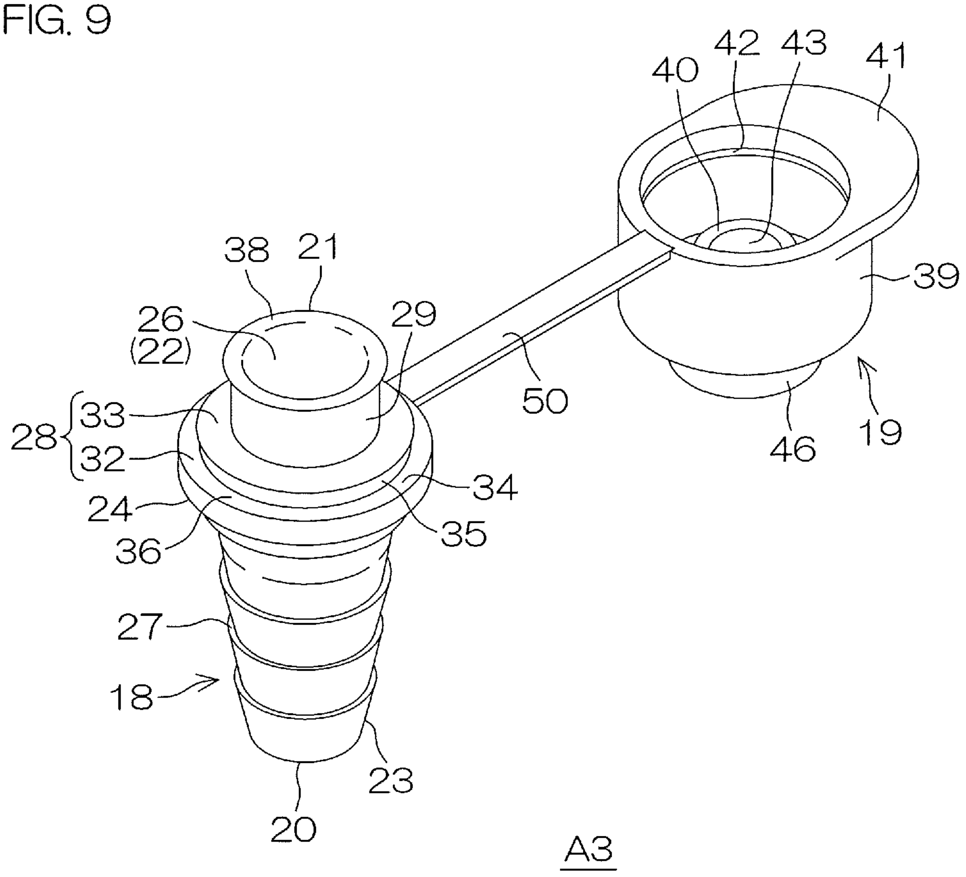
FIG. 9 is a perspective view of a cap according to a third preferred embodiment of the present invention.

FIG. 9 is a perspective view of a cap A3 according to a third preferred embodiment of the present invention. In FIG. 9, arrangements equivalent to arrangements indicated in the preferred embodiments described above shall be provided with the same reference signs and description thereof shall be omitted.

With the cap A3 according to this preferred embodiment, the main body 18 and the lid portion 19 are connected by a string 50 in place of the hinge mechanism 49. The string 50 may be constituted of the resin integral to the main body 18 and the lid portion 19.

With the cap A3, the drain hole 26 can be blocked easily by pressing the lid portion 19 into the drain hole 26 because the portion that blocks the drain hole 26 is the plug portion 40.

Fourth Preferred Embodiment

Figure 10:
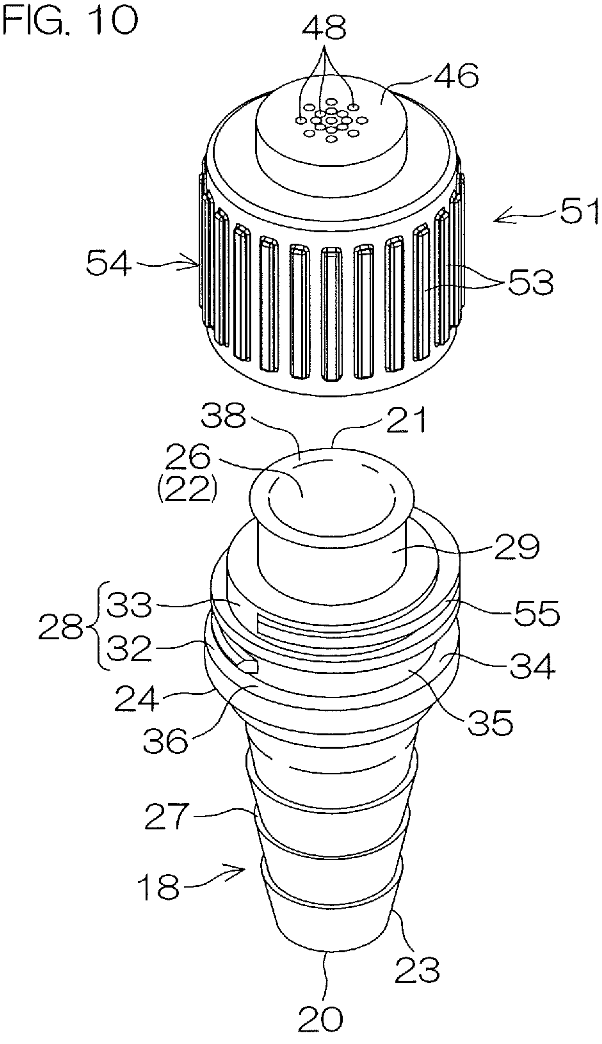
FIG. 10 is a perspective view of a cap according to a fourth preferred embodiment of the present invention.
Figure 11:
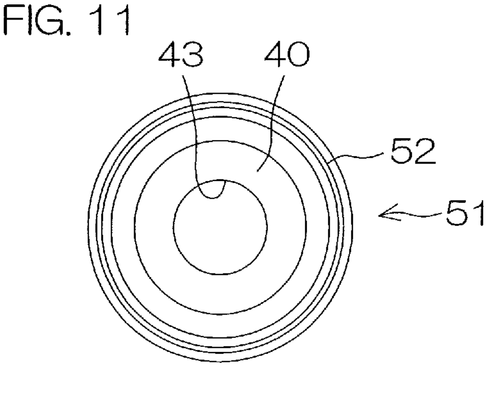
FIG. 11 is a bottom view of a lid portion of FIG. 10.
Figure 12:
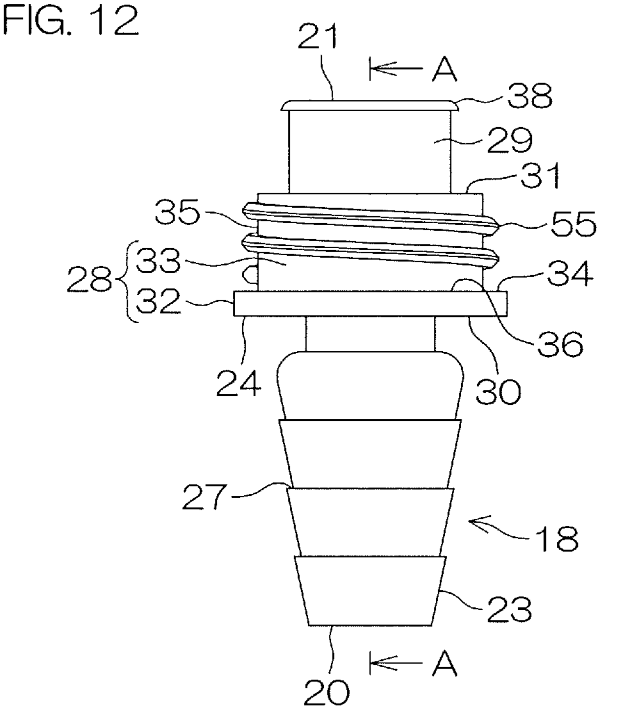
FIG. 12 is a side view of a main body of FIG. 10.
Figure 13:
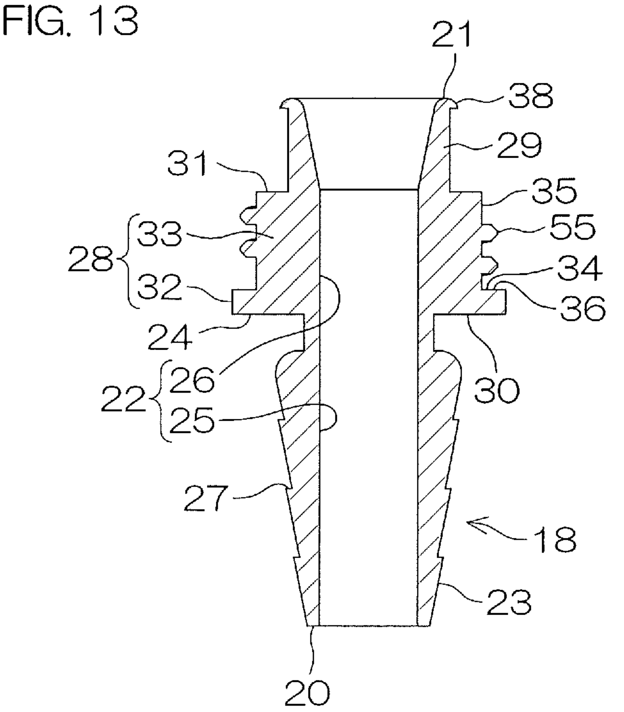
FIG. 13 is a diagram showing a section taken along A-A of FIG. 10.

FIG. 10 is a perspective view of a cap A4 according to a fourth preferred embodiment of the present invention. FIG. 11 is a bottom view of a lid portion 51 of FIG. 10. FIG. 12 is a side view of the main body 18 of FIG. 10. FIG. 13 is a diagram showing a section taken along A-A of FIG. 10. In FIG. 10 to FIG. 13, arrangements equivalent to arrangements indicated in the preferred embodiments described above shall be provided with the same reference signs and description thereof shall be omitted.

The cap A4 according to this preferred embodiment includes a lid portion 51 of a screw type in place of the lid portion 19 that is connected to the main body 18 by the hinge mechanism 49. The lid portion 51 is formed to a dome shape and a screw thread 52 with a spiral shape is formed on an inner circumferential surface of the lid portion 51. Also, an anti-slip structure 54 constituted of a plurality of projecting ridges 53 is formed on an outer circumferential surface of the lid portion 51. The plurality of projecting ridges 53 are aligned at intervals across an entire circumference in a circumferential direction of the lid portion 51. Each projecting ridge 53 extends in an axial direction (drain direction of urine) of the lid portion 51.

A screw thread 55 with a spiral shape that is screwed to the screw thread 52 of the lid portion 51 is formed on the side surface 35 of the base portion 28 of the drain portion 24 of the main body 18. For example, by turning and fastening the lid portion 51 onto the main body 18, the plug portion 40 is inserted into the drain hole 26 and the drain hole 26 can be closed.

With the cap A4, the main body 18 and the lid portion 51 are screwed together by the lid portion 51 of the screw type and therefore, the drain hole 26 can be blocked securely.

Fifth Preferred Embodiment

Figure 14:
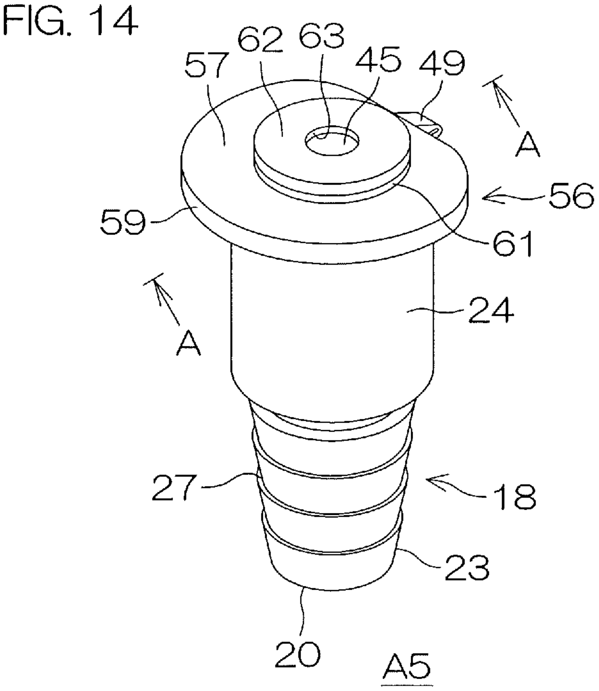
FIG. 14 is a perspective view of a cap according to a fifth preferred embodiment of the present invention.
Figure 15:
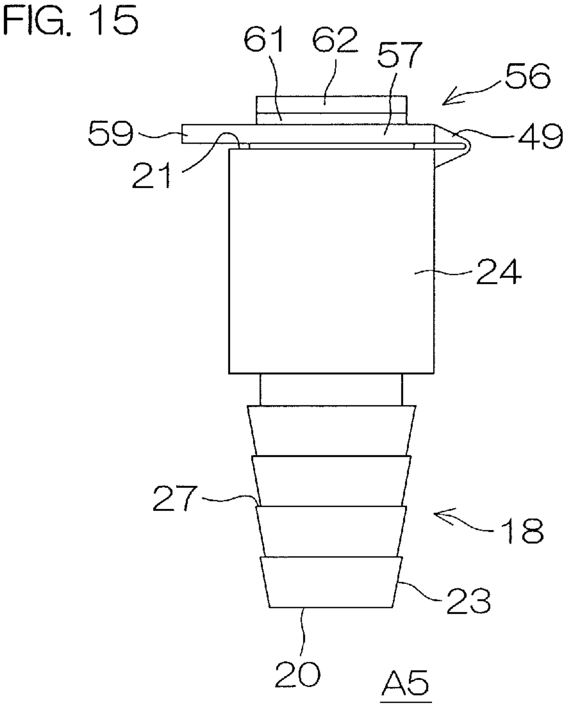
FIG. 15 is a side view of the cap according to the fifth preferred embodiment of the present invention.
Figure 16:
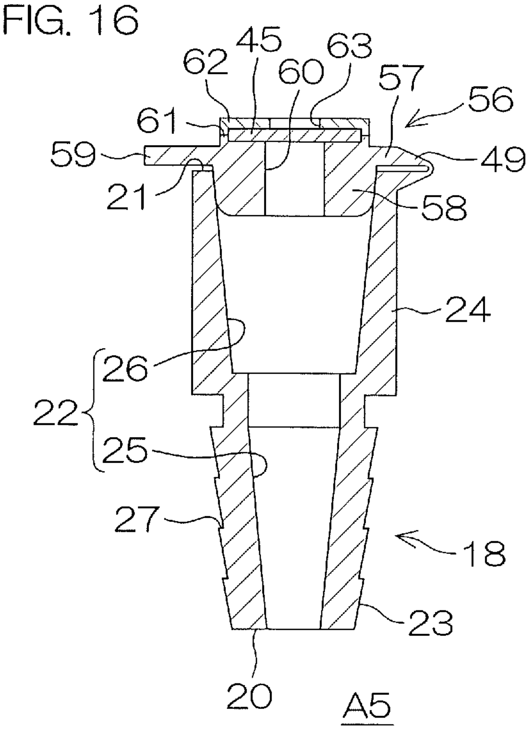
FIG. 16 is a diagram showing a section taken along A-A of FIG. 14.

FIG. 14 is a perspective view of a cap A5 according to a fifth preferred embodiment of the present invention. FIG. 15 is a side view of the cap A5 according to the fifth preferred embodiment of the present invention. FIG. 16 is a diagram showing a section taken along A-A of FIG. 14. In FIG. 14 to FIG. 16, arrangements equivalent to arrangements indicated in the preferred embodiments described above shall be provided with the same reference signs and description thereof shall be omitted.

With the cap A5 according to this preferred embodiment, there is no differentiation into the base portion 28 and the drain outlet 29 at the drain portion 24. The drain portion 24 is formed to a circular tubular shape that is connected to the connection portion 23. Unlike in the caps A1 to A4 according to the first to fourth preferred embodiments, an open end portion of the drain portion 24 has a flat shape with an outer diameter being substantially fixed. The drain hole 26 has a tapered shape that narrows in diameter from an open end of the drain portion 24 (second end portion 21 of the main body 18) toward the connection portion 23.

A lid portion 56 may include a base portion 57 with a disc shape having a larger outer diameter than the drain portion 24 and a plug portion 58 that projects from a lower surface (surface opposing the drain hole 26) of the base portion 57. An outer circumferential portion 59 of the base portion 57 is of an arrangement that protrudes in a flange shape toward an outer side of the drain portion 24 in a state where the lid portion 56 is closed.

The plug portion 58 is formed to a tubular shape with an open hole 60 formed therein. Also, the plug portion 58 has a tapered shape that narrows in outer diameter toward a tip of the plug portion 58.

A film placement portion 61 with a circular annular shape that projects upward is formed on an upper surface of the base portion 57. The open hole 60 is formed in the lid portion 56 such as to pass continuously through the film placement portion 61 and the plug portion 58. The hydrophobic film 45 is disposed on the film placement portion 61 such as to block the open hole 60. Also, the film placement portion 61 has a larger outer diameter than the hydrophobic film 45.

Also, a cover member 62 is provided on the film placement portion 61 such as to cover the hydrophobic film 45. The cover member 62 is formed to a disc shape having substantially the same outer diameter as the film placement portion 61. The cover member 62 is bonded to an outer circumferential portion of the film placement portion 61 such that its outer circumferential portion contacts the film placement portion 61 and a central portion surrounded by the outer circumferential portion contacts the hydrophobic film 45. The cover member 62 may be bonded to the film placement portion 61, for example, by heat welding, adhesive agent, etc.

Also, a flow port 63 that enables flow of air in a thickness direction of the cover member 62 is formed in the cover member 62. The hydrophobic film 45 is exposed from the flow port 63.

The lid portion 56 can be closed, for example, by pinching the outer circumferential portion 59 of the base portion 57 to fold the hinge mechanism 49 and pressing the upper surface of the base portion 57. By pressing the upper surface of the base portion 57, the plug portion 58 is inserted into the drain hole 26. The drain hole 26 can thereby be closed. In this state, the urine introduction passage 22 of the main body 18 and the open hole 60 of the lid portion 56 are in mutual communication as shown in FIG. 16.

With the cap A5, positioning of the lid portion 56 with respect to the drain hole 26 does not have to be performed in closing the lid portion 56 because the lid portion 56 is coupled to the main body 18 via the hinge mechanism 49. Also, the drain hole 26 can be blocked easily by pressing the lid portion 56 into the drain hole 26 because the portion that blocks the drain hole 26 is the plug portion 58.

Sixth Preferred Embodiment

Figure 17:
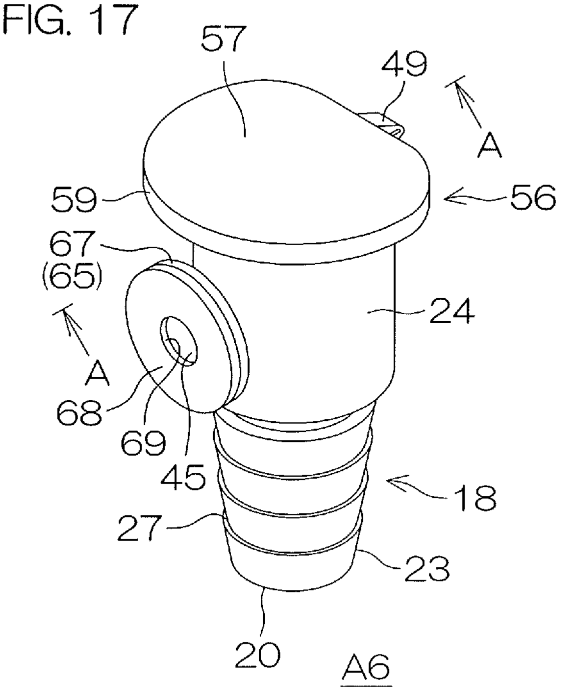
FIG. 17 is a perspective view of a cap according to a sixth preferred embodiment of the present invention.
Figure 18:
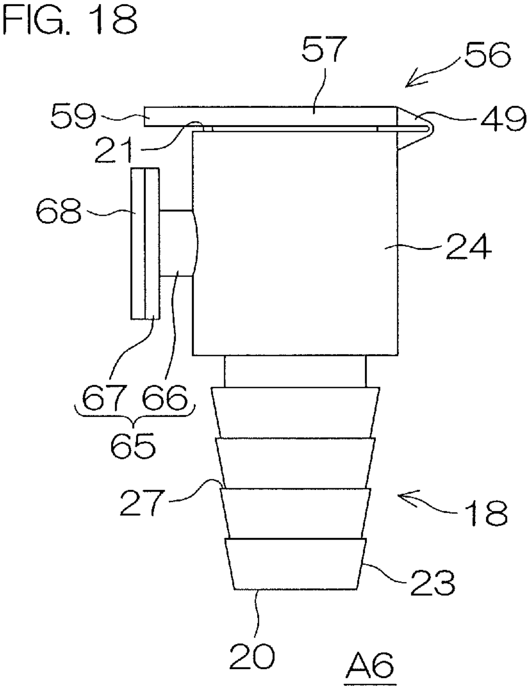
FIG. 18 is a side view of the cap according to the sixth preferred embodiment of the present invention.
Figure 19:
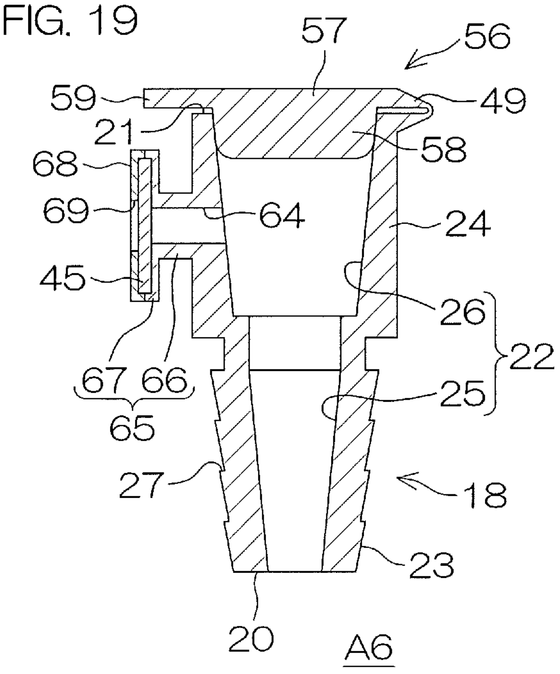
FIG. 19 is a diagram showing a section taken along A-A of FIG. 17.

FIG. 17 is a perspective view of a cap A6 according to a sixth preferred embodiment of the present invention. FIG. 18 is a side view of the cap A6 according to the sixth preferred embodiment of the present invention. FIG. 19 is a diagram showing a section taken along A-A of FIG. 17. In FIG. 17 to FIG. 19, arrangements equivalent to arrangements indicated in the preferred embodiments described above shall be provided with the same reference signs and description thereof shall be omitted.

With the cap A6 according to this preferred embodiment, the open hole 60 that is blocked by the hydrophobic film 45 is not formed in the lid portion 56 but is formed such as to be connected to an intermediate portion of the urine introduction passage 22 of the main body 18. More specifically, an open hole 64 is formed such as to penetrate through a side wall of the drain portion 24 of the main body 18.

A film placement portion 65 is formed to project from the side wall of the main body 18. More specifically, the film placement portion 65 includes a supporting body 66 that projects from the side wall of the main body 18 (drain portion 24) and a film placement plate 67 that is formed to a flange shape with respect to the supporting body 66. The supporting body 66 is formed to a circular tubular shape and the film placement plate 67 is formed to a disc shape. The open hole 64 is formed such as to pass continuously through the film placement plate 67, the supporting body 66, and the side wall of the main body 18.

The hydrophobic film 45 is disposed on the film placement plate 67 such as to block the open hole 64. Also, the film placement plate 67 has a larger outer diameter than the hydrophobic film 45.

Also, a cover member 68 is provided on the film placement plate 67 such as to cover the hydrophobic film 45. The cover member 68 is formed to a disc shape having substantially the same outer diameter as the film placement plate 67. The cover member 68 is bonded to an outer circumferential portion of the film placement plate 67 such that its outer circumferential portion contacts the film placement plate 67 and a central portion surrounded by the outer circumferential portion contacts the hydrophobic film 45. The cover member 68 may be bonded to the film placement plate 67, for example, by heat welding, adhesive agent, etc.

Also, a flow port 69 that enables flow of air in a thickness direction of the cover member 68 is formed in the cover member 68. The hydrophobic film 45 is exposed from the flow port 69.

Seventh Preferred Embodiment

Figure 20:
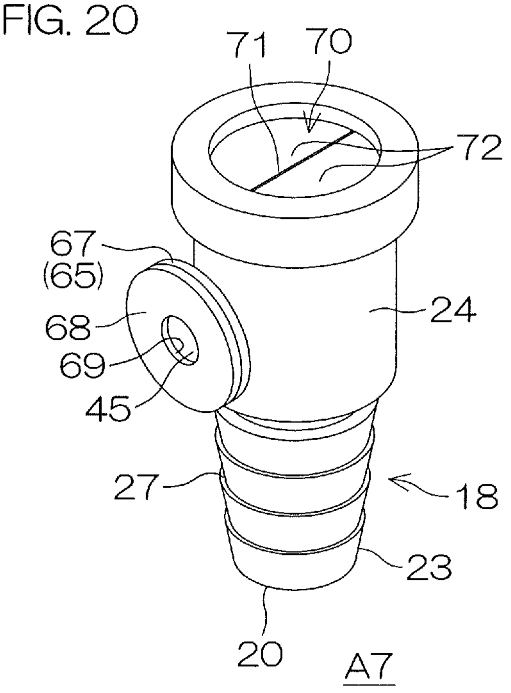
FIG. 20 is a perspective view of a cap according to a seventh preferred embodiment of the present invention.
Figure 21:
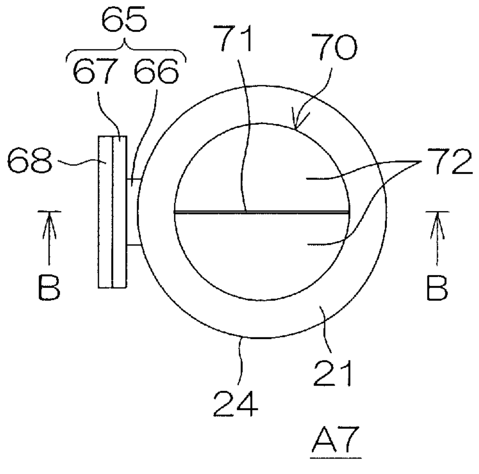
FIG. 21 is a plan view of the cap according to the seventh preferred embodiment of the present invention.
Figure 22:
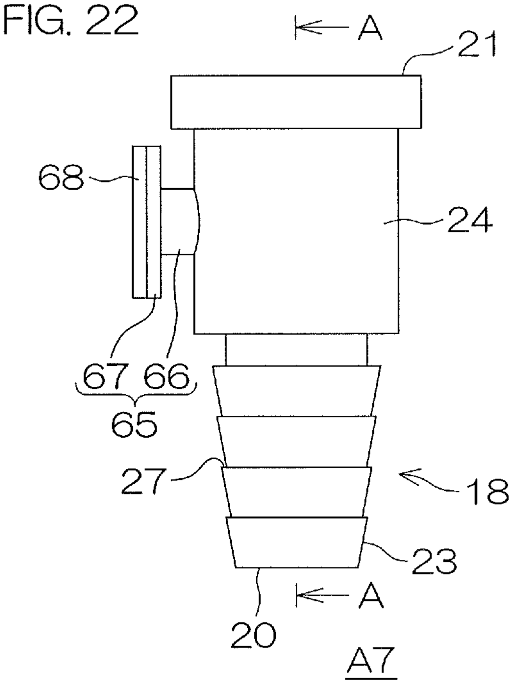
FIG. 22 is a side view of the cap according to the seventh preferred embodiment of the present invention.
Figure 23:
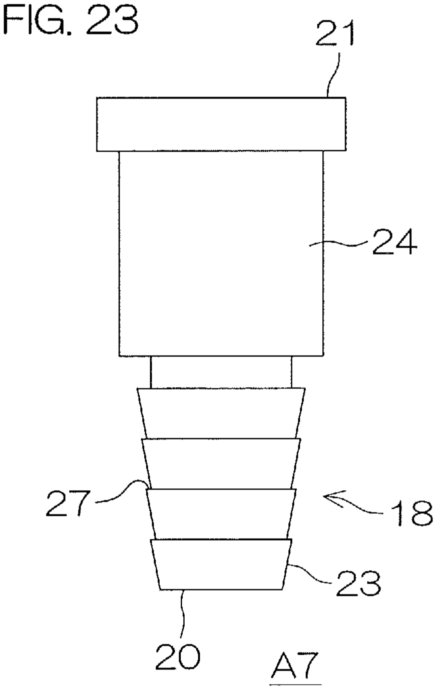
FIG. 23 is a rear view of the cap according to the seventh preferred embodiment of the present invention.
Figure 24:
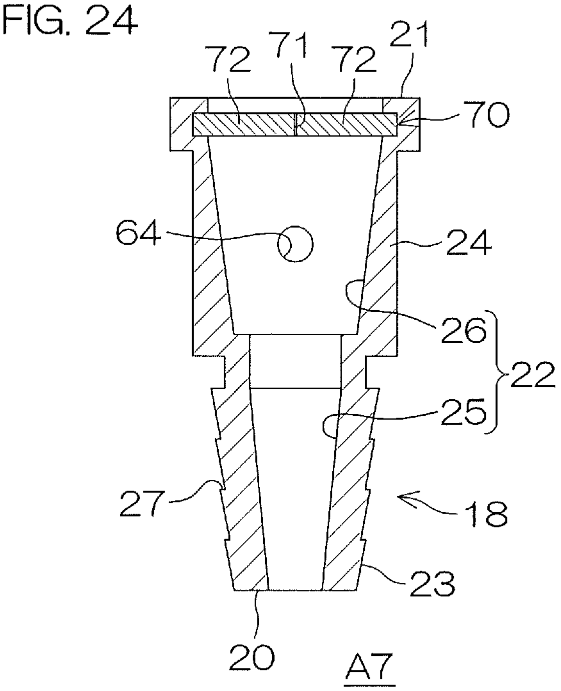
FIG. 24 is a diagram showing a section taken along A-A of FIG. 21.
Figure 25:
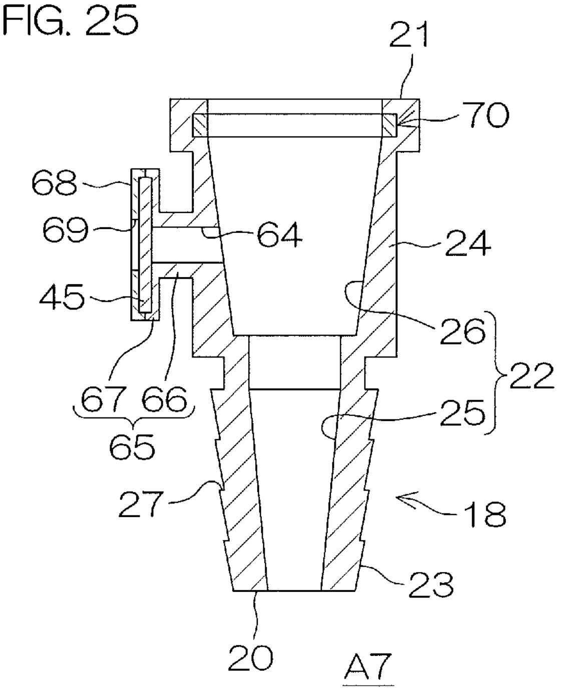
FIG. 25 is a diagram showing a section taken along B-B of FIG. 21.

FIG. 20 is a perspective view of a cap A7 according to a seventh preferred embodiment of the present invention. FIG. 21 is a plan view of the cap A7 according to the seventh preferred embodiment of the present invention. FIG. 22 is a side view of the cap A7 according to the seventh preferred embodiment of the present invention. FIG. 23 is a rear view of the cap A7 according to the seventh preferred embodiment of the present invention. FIG. 24 is a diagram showing a section taken along A-A of FIG. 21. FIG. 25 is a diagram showing a section taken along B-B of FIG. 21. In FIG. 20 to FIG. 25, arrangements equivalent to arrangements indicated in the preferred embodiments described above shall be provided with the same reference signs and description thereof shall be omitted.

With the cap A7 according to this preferred embodiment, a lid portion 70 is formed of a so-called split septum structure. More specifically, the lid portion 70 may include a valve element 72 of disc shape with an insertion hole (slit 71) formed in a central portion. The valve element 72 is formed of an elastic material. As the elastic material, for example, a latex rubber, an isoprene rubber, a silicone, a thermoplastic elastomer (for example, a styrene-based elastomer, etc.), etc., can be used. Such a valve element 72 can be affixed to the open end portion of the drain portion 24 of the main body 18, for example, by being insert molded.

With the cap A7, for example, a urine collection bag, etc., can be inserted directly into the cap A7 because the lid portion 70 is formed of the valve element 72 having the slit 71.

Eighth Preferred Embodiment

Figure 26:
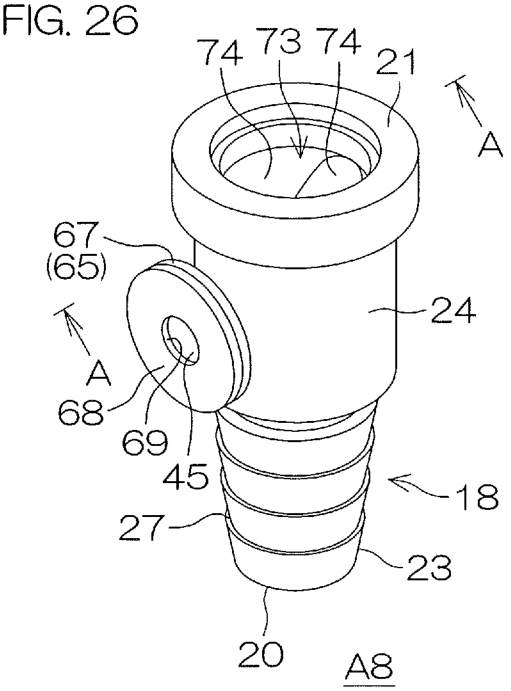
FIG. 26 is a perspective view of a cap according to an eighth preferred embodiment of the present invention.
Figure 27:
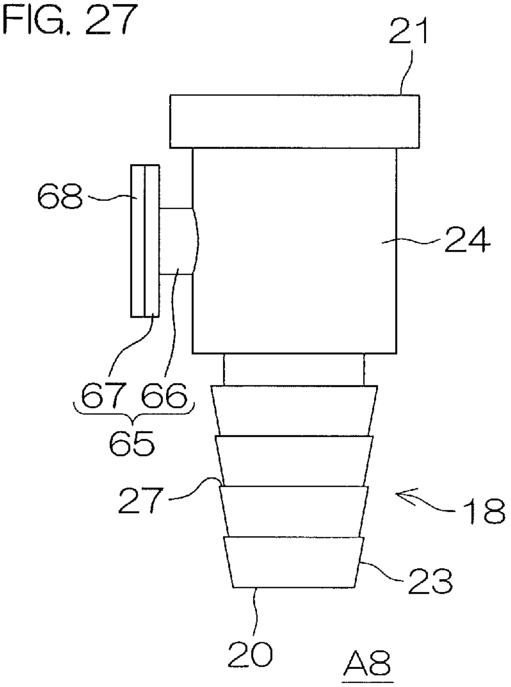
FIG. 27 is a side view of the cap according to the eighth preferred embodiment of the present invention.
Figure 28:
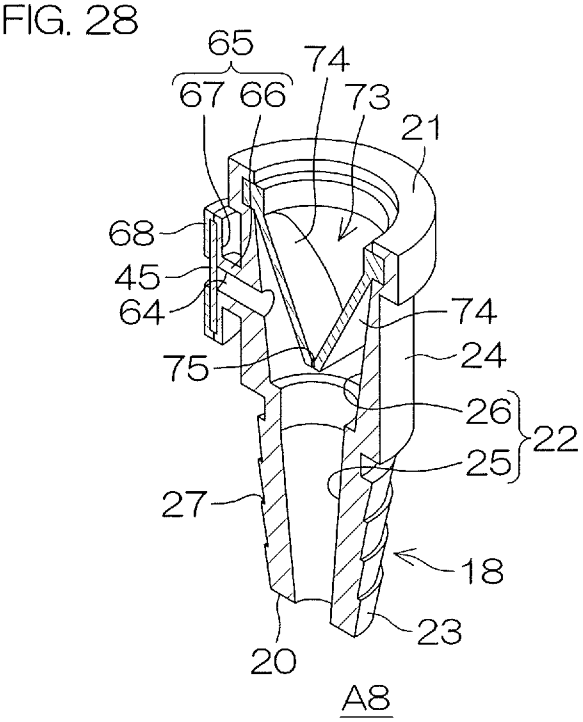
FIG. 28 is a diagram showing a section taken along A-A of FIG. 26.
Figure 29:
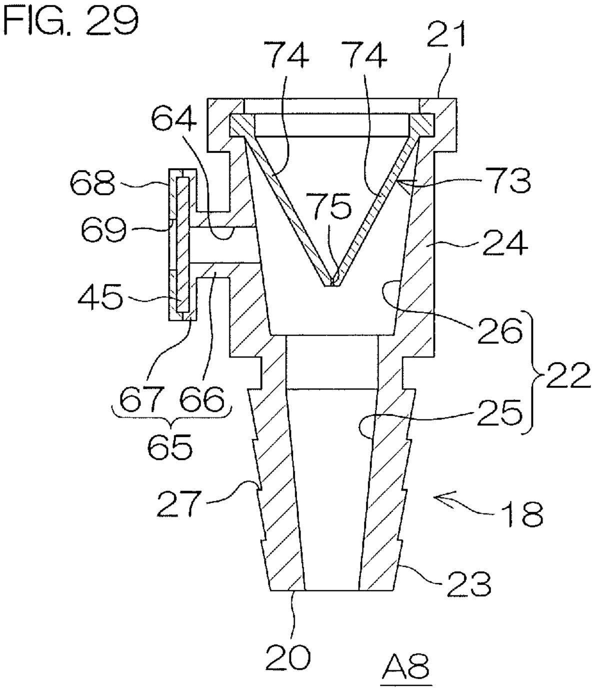
FIG. 29 is a diagram showing the section taken along A-A of FIG. 26.

FIG. 26 is a perspective view of a cap A8 according to an eighth preferred embodiment of the present invention. FIG. 27 is a side view of the cap A8 according to the eighth preferred embodiment of the present invention. FIG. 28 and FIG. 29 are diagrams showing a section taken along A-A of FIG. 26 with FIG. 28 being a diagram as viewed from obliquely above and FIG. 29 being a diagram as viewed from a side. In FIG. 26 to FIG. 29, arrangements equivalent to arrangements indicated in the preferred embodiments described above shall be provided with the same reference signs and description thereof shall be omitted.

With the cap A8 according to this preferred embodiment, a lid portion 73 is formed of a so-called duckbill valve structure. More specifically, the lid portion 73 has a pair of inclining valve elements 74 that extend such as to converge toward the connection hole 25 from the open end of the drain portion 24. The pair of inclining valve elements 74 contact each other at the tips and a slit 75 is formed at the tips. The inclining valve elements 74 are formed of an elastic material. As the elastic material, for example, a latex rubber, an isoprene rubber, a silicone, a thermoplastic elastomer (for example, a styrene-based elastomer, etc.), etc., can be used. Such inclining valve elements 74 can be affixed to the open end portion of the drain portion 24 of the main body 18, for example, by being insert molded.

With the cap A8, for example, a urine collection bag, etc., can be inserted directly into the cap A8 because the lid portion 73 is formed of the inclining valve elements 74 having the slit 75.

Ninth Preferred Embodiment

Figure 30:
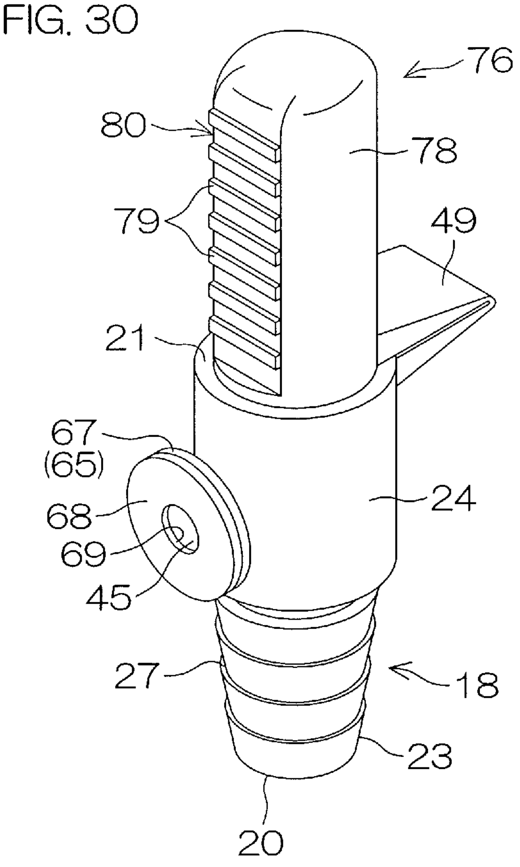
FIG. 30 is a perspective view of a cap according to a ninth preferred embodiment of the present invention.
Figure 31:
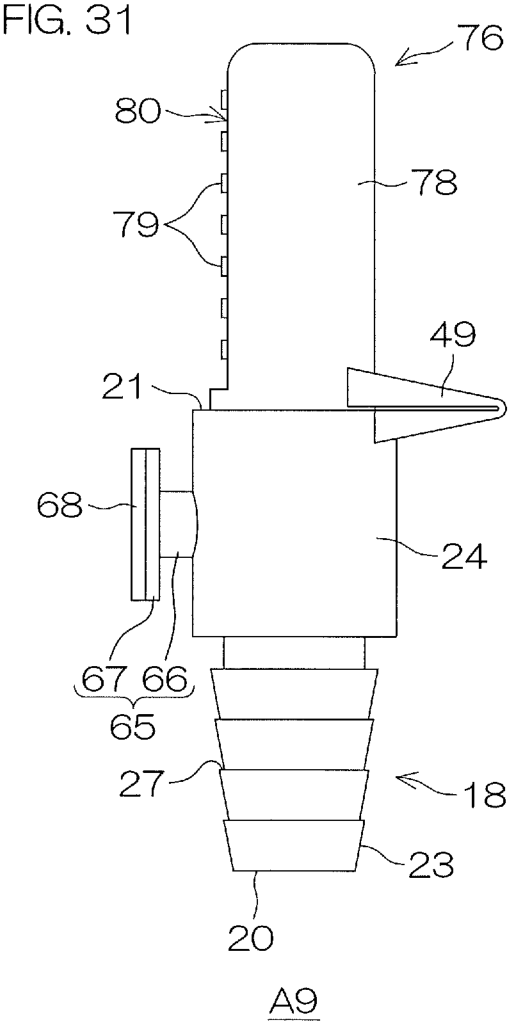
FIG. 31 is a side view of the cap according to the ninth preferred embodiment of the present invention.
Figure 32:
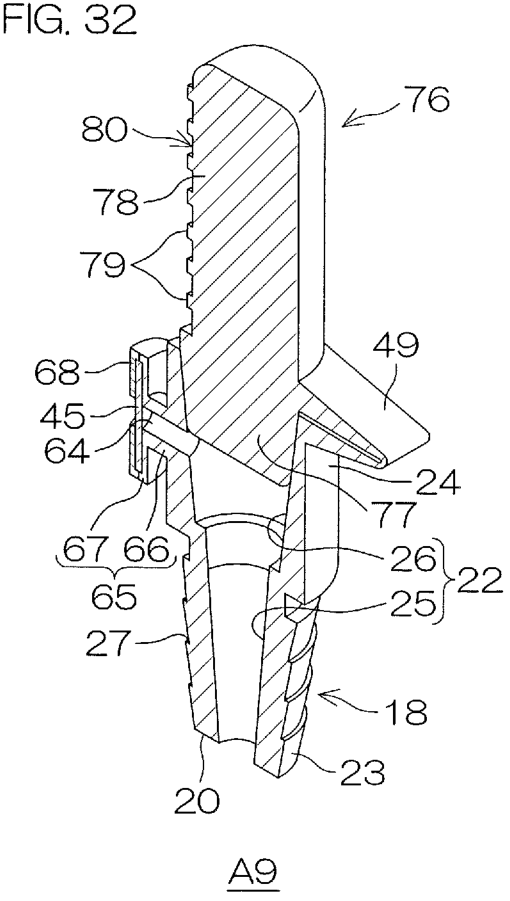
FIG. 32 is a diagram showing a section taken along A-A of FIG. 30.
Figure 33:
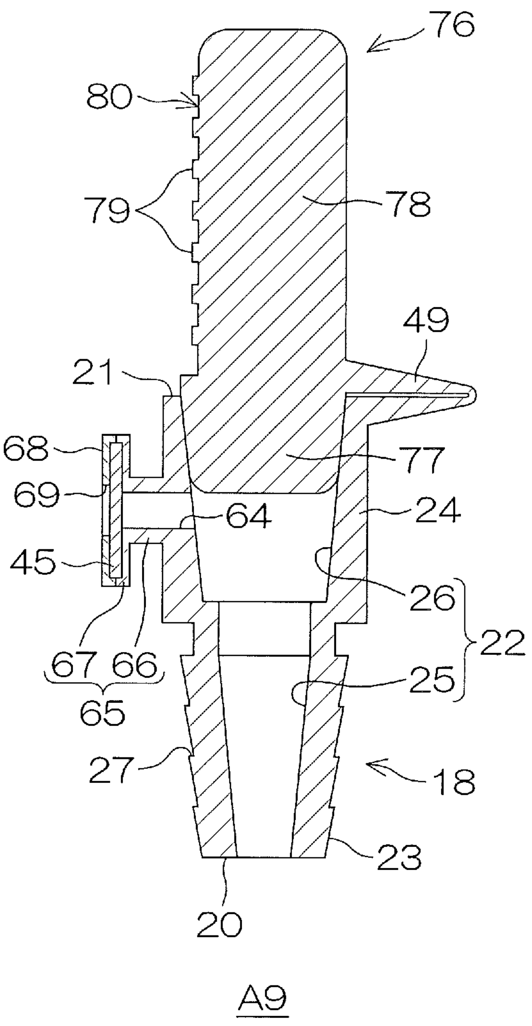
FIG. 33 is a diagram showing the section taken along A-A of FIG. 30.

FIG. 30 is a perspective view of a cap A9 according to a ninth preferred embodiment of the present invention. FIG. 31 is a side view of the cap A9 according to the ninth preferred embodiment of the present invention. FIG. 32 and FIG. 33 are diagrams showing a section taken along A-A of FIG. 30 with FIG. 32 being a diagram as viewed from obliquely above and FIG. 33 being a diagram as viewed from a side. In FIG. 30 to FIG. 33, arrangements equivalent to arrangements indicated in the preferred embodiments described above shall be provided with the same reference signs and description thereof shall be omitted.

With the cap A9 according to this preferred embodiment, a lid portion 76 is formed to a stick shape. More specifically, the lid portion 76 has a plug portion 77 that is inserted into the drain hole 26 and a columnar portion 78 that is coupled to the plug portion 77. The plug portion 77 has a tapered shape that narrows in outer diameter toward a tip of the plug portion 77.

The columnar portion 78 is formed to a circular columnar shape having substantially the same length as the main body 18. An anti-slip structure 80 constituted of a plurality of projecting ridges 79 is formed on a portion of a side surface of the columnar portion 78. The plurality of projecting ridges 79 are aligned at intervals in a length direction of the columnar portion 78. Each projecting ridge 79 extends in a circumferential direction of the columnar portion 78.

The lid portion 76 with the stick shape is coupled integrally to the main body 18 via the hinge mechanism 49. In this preferred embodiment, the hinge mechanism 49 is connected to a plug portion 77 side end portion of the column portion 78 at an opposite side to the anti-slip structure 80.

With this cap A9, since the lid portion 76 has the stick shape, the lid portion 76 can be opened easily with one hand, for example, by placing a thumb on the anti-slip structure 80 and pushing the lid portion 76 with the thumb.

Tenth Preferred Embodiment

Figure 34:
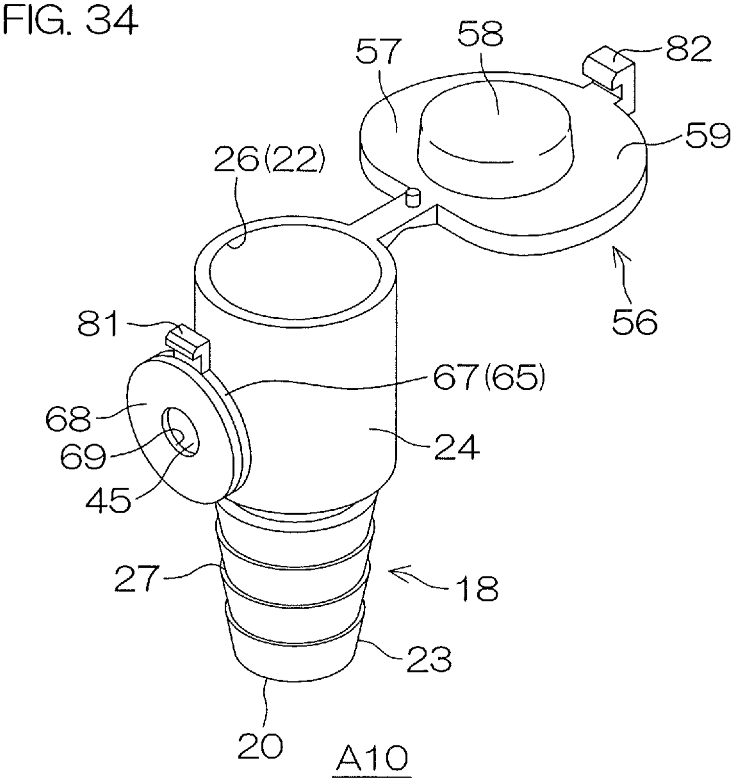
FIG. 34 is a perspective view of a cap according to a tenth preferred embodiment of the present invention.
Figure 35:
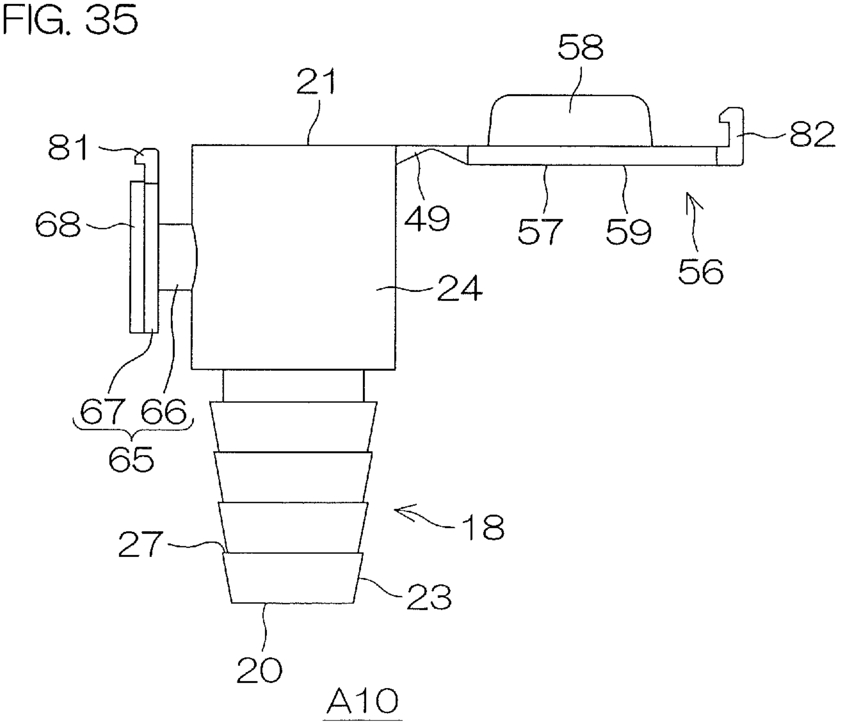
FIG. 35 is a side view of the cap according to the tenth preferred embodiment of the present invention.
Figure 36:
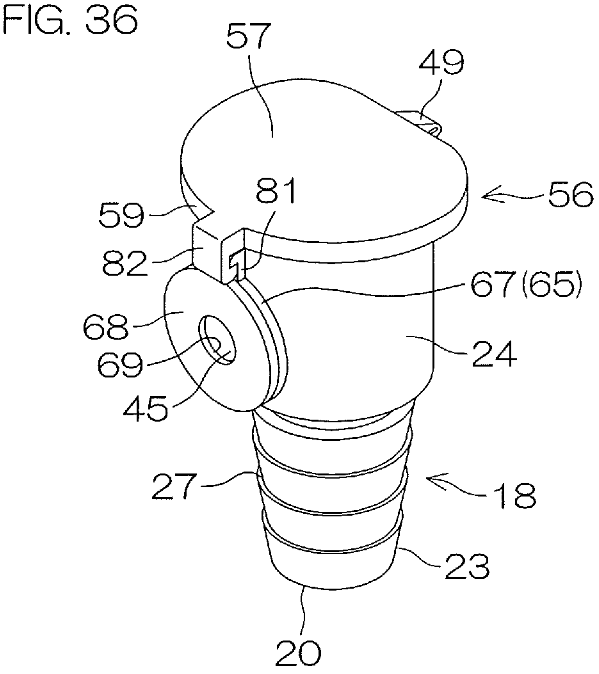
FIG. 36 is a perspective view of the cap according to the tenth preferred embodiment of the present invention.
Figure 37:
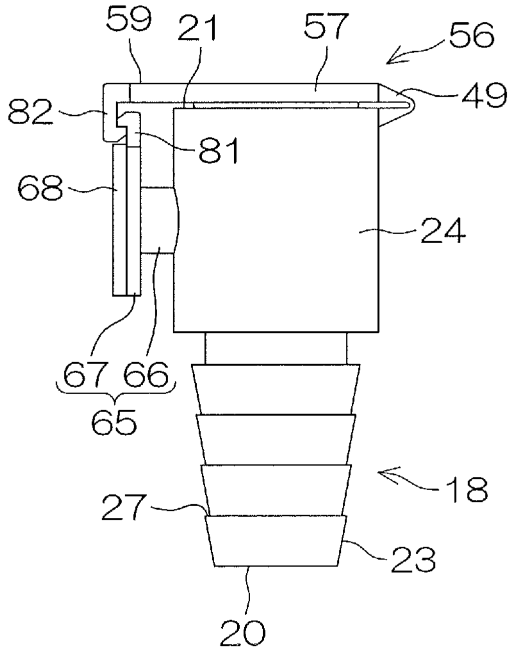
FIG. 37 is a side view of the cap according to the tenth preferred embodiment of the present invention.

FIG. 34 and FIG. 35 are a perspective view and a side view, respectively, of a cap A10 according to a tenth preferred embodiment of the present invention and show a state where the lid portion 56 is opened. FIG. 36 and FIG. 37 are a perspective view and a side view, respectively, of the cap A10 according to the tenth preferred embodiment of the present invention and show a state where the lid portion 56 is closed. In FIG. 34 to FIG. 37, arrangements equivalent to arrangements indicated in the preferred embodiments described above shall be provided with the same reference signs and description thereof shall be omitted.

With the cap A10 according to this preferred embodiment, a first engaging portion 81 is formed at a circumferential edge portion of the film placement plate 67 and a second engaging portion 82 is formed at the outer circumferential portion 59 of the base portion 57 with a disc shape. The first engaging portion 81 and the second engaging portion 82 are mutually engaged in the state where the lid portion 56 is closed. The lid portion 56 can be locked to the main body 18 by this engagement.

Also, for example, if the hinge mechanism 49 is urged in a direction in which the lid portion 56 opens, the lid portion 56 can be opened by an urging force of the hinge mechanism 49 by pressing the film placement plate 67 like a button to release the engagement of the first engaging portion 81 and the second engaging portion 82. The lid portion 56 can be opened without touching it directly and therefore, wetting of a hand with urine during opening of the lid portion 56 can be prevented reliably.

[Method for Affixing the Hydrophobic Film 45]

Next, other modes shall be illustrated in regard to a method for affixing the hydrophobic film 45. Although in the preferred embodiments described above, the hydrophobic film 45 is affixed by covering with the cover member 46, 62, or 68, it can also be affixed by other modes as shown in FIG. 38A and FIG. 38B and FIG. 39A to FIG. 39D.

Figure 38A:
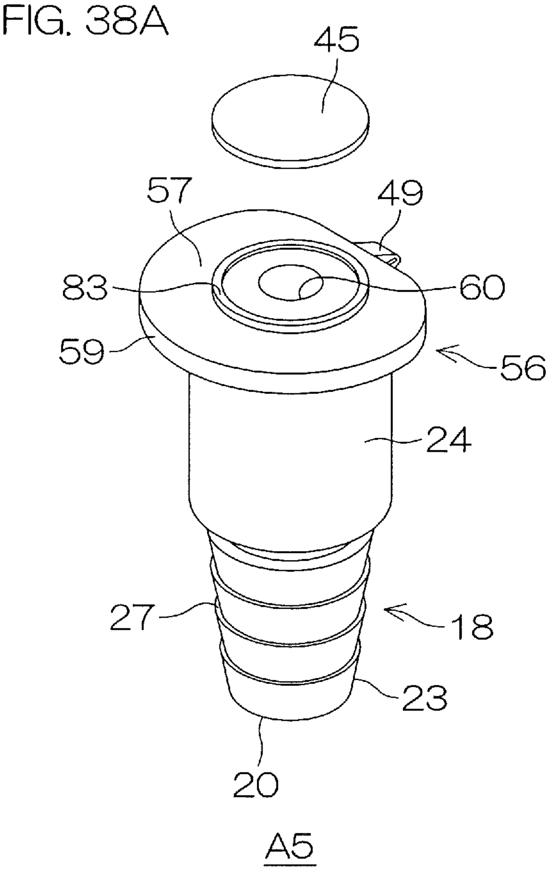
FIG. 38A is a diagram for describing a method for affixing the hydrophobic film.
Figure 38B:
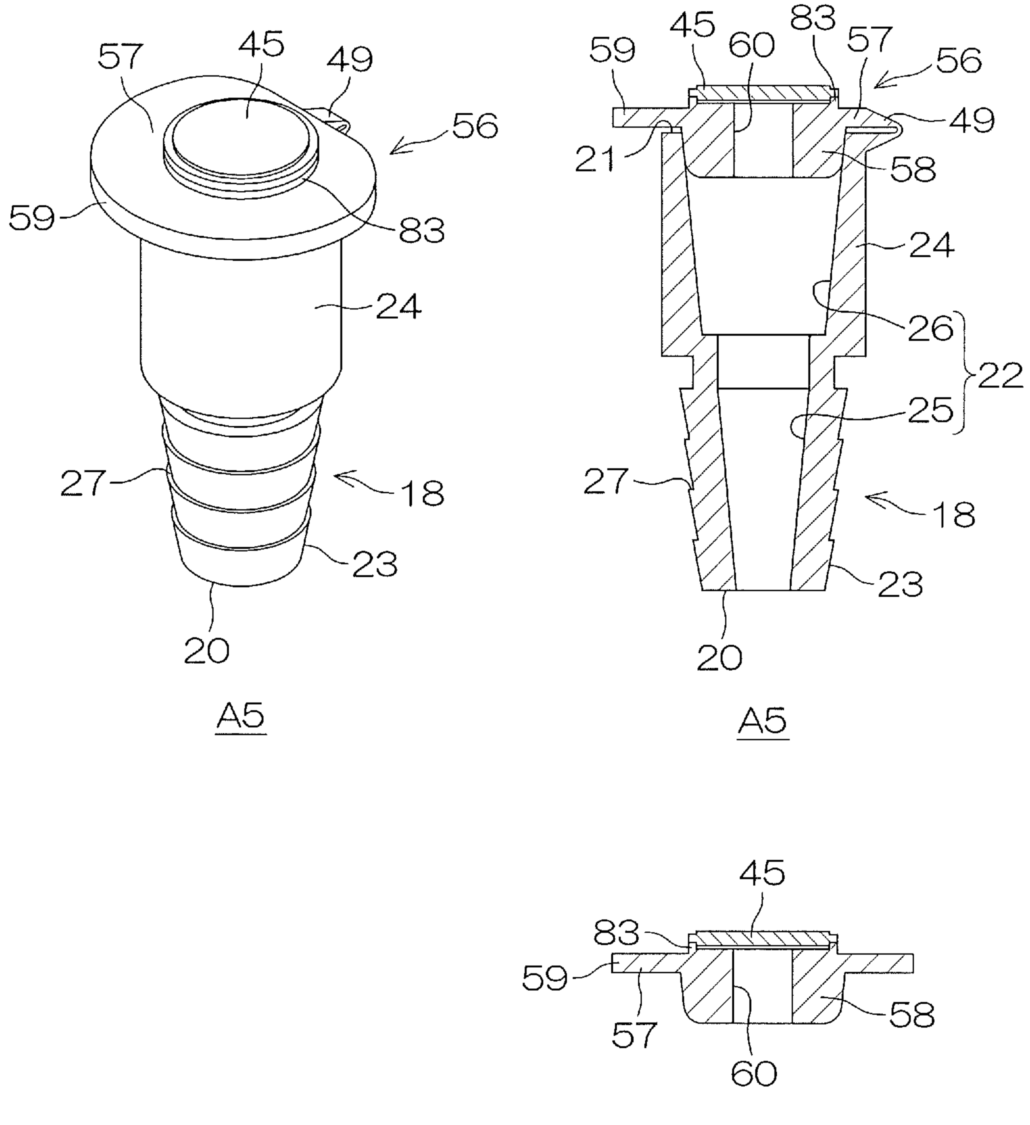
FIG. 38B is a diagram of a step subsequent to that of FIG. 38A.

FIG. 38A and FIG. 38B are diagrams for describing a method for affixing the hydrophobic film 45 (first mode). FIG. 39A to FIG. 39D are diagrams for describing a method for affixing the hydrophobic film 45 (second mode). With FIG. 38A and FIG. 38B and FIG. 39A to FIG. 39D, descriptions shall be provided with reference to the structure of the cap A5 of the fifth preferred embodiment.

<First Mode>

First, as shown in FIG. 38A, the main body 18 and the lid portion 56 that are integrally molded and the hydrophobic film 45 are prepared. The film placement portion 83 is formed, for example, to a circular annular shape that surrounds the open hole 60 and has substantially the same outer diameter as the hydrophobic film 45. Next, as shown in FIG. 38B, the hydrophobic film 45 with a disc shape is placed on the film placement portion 83 with the circular annular shape and the hydrophobic film 45 is heat welded onto the film placement portion 83 from an upper side. The hydrophobic film 45 can thereby be affixed.

<Second Mode>

Figure 39A:
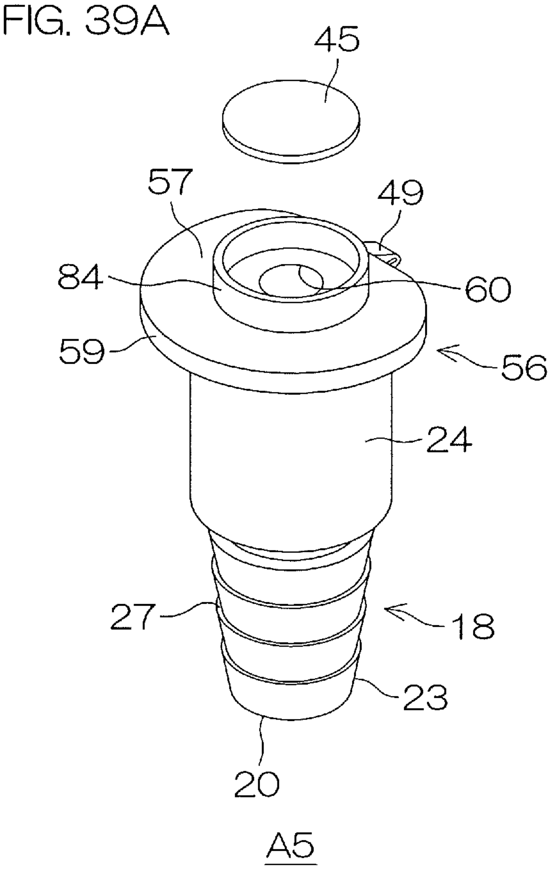
FIG. 39A is a diagram for describing a method for affixing the hydrophobic film.
Figure 39B:
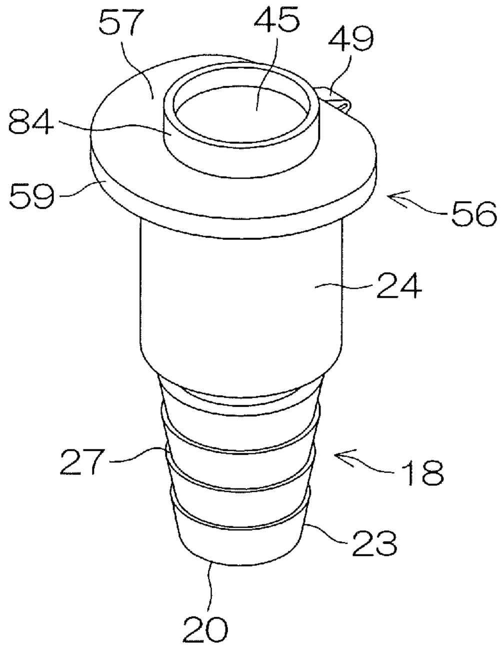
FIG. 39B is a diagram of a step subsequent to that of FIG. 39A.
Figure 39B:
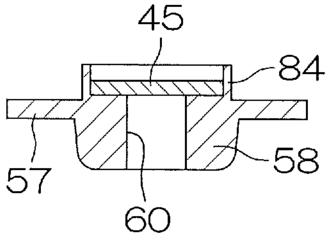
Figure 39C:
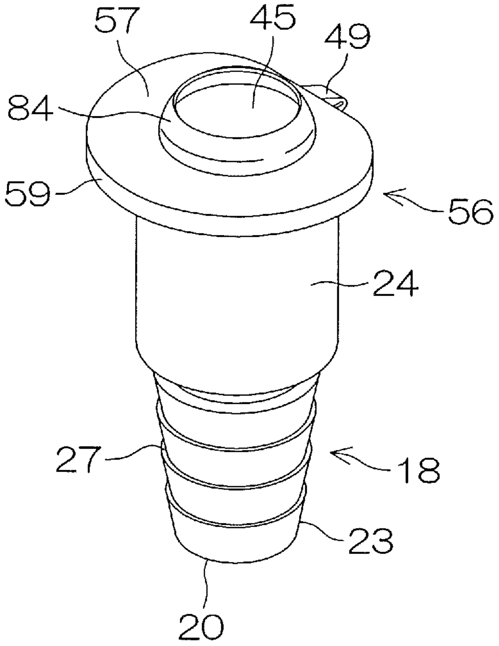
FIG. 39C is a diagram of a step subsequent to that of FIG. 39B.
Figure 39C:
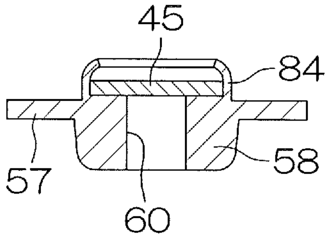
Figure 39D:
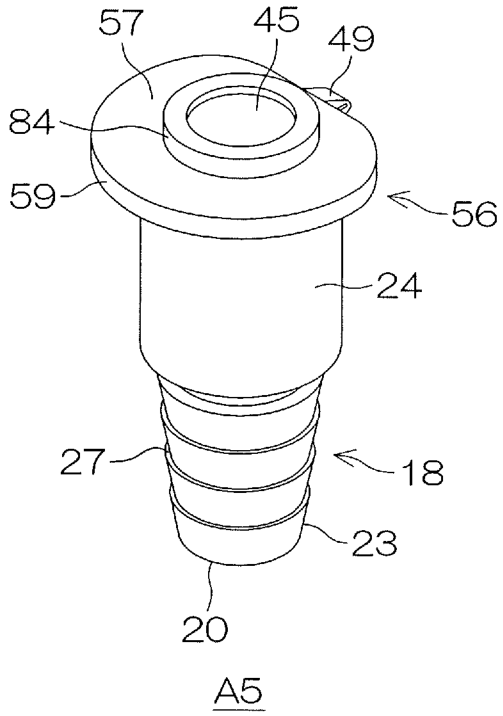
FIG. 39D is a diagram of a step subsequent to that of FIG. 39C.
Figure 39D:
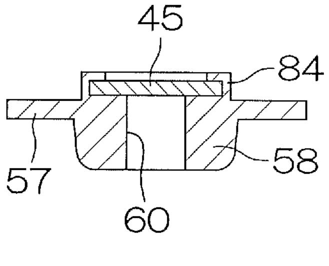

First, as shown in FIG. 39A, the main body 18 and the lid portion 56 that are integrally molded and the hydrophobic film 45 are prepared. The film placement portion 84 is formed, for example, to a circular tubular shape that surrounds the open hole 60 and has an inner diameter that is substantially the same as the outer diameter of the hydrophobic film 45. Next, as shown in FIG. 39B, the hydrophobic film 45 is set in an interior of the film placement portion 84. Next, as shown in FIG. 39C, a side wall (circumferential wall) of the film placement portion 84 is heated to make the side wall flexible and is bent toward an inner side. The hydrophobic film 45 is thereby crimped and affixed by the film placement portion 84.

[Method for Using the Catheter 1 and Effects Due to the Caps A1 to A10]

Figure 40:
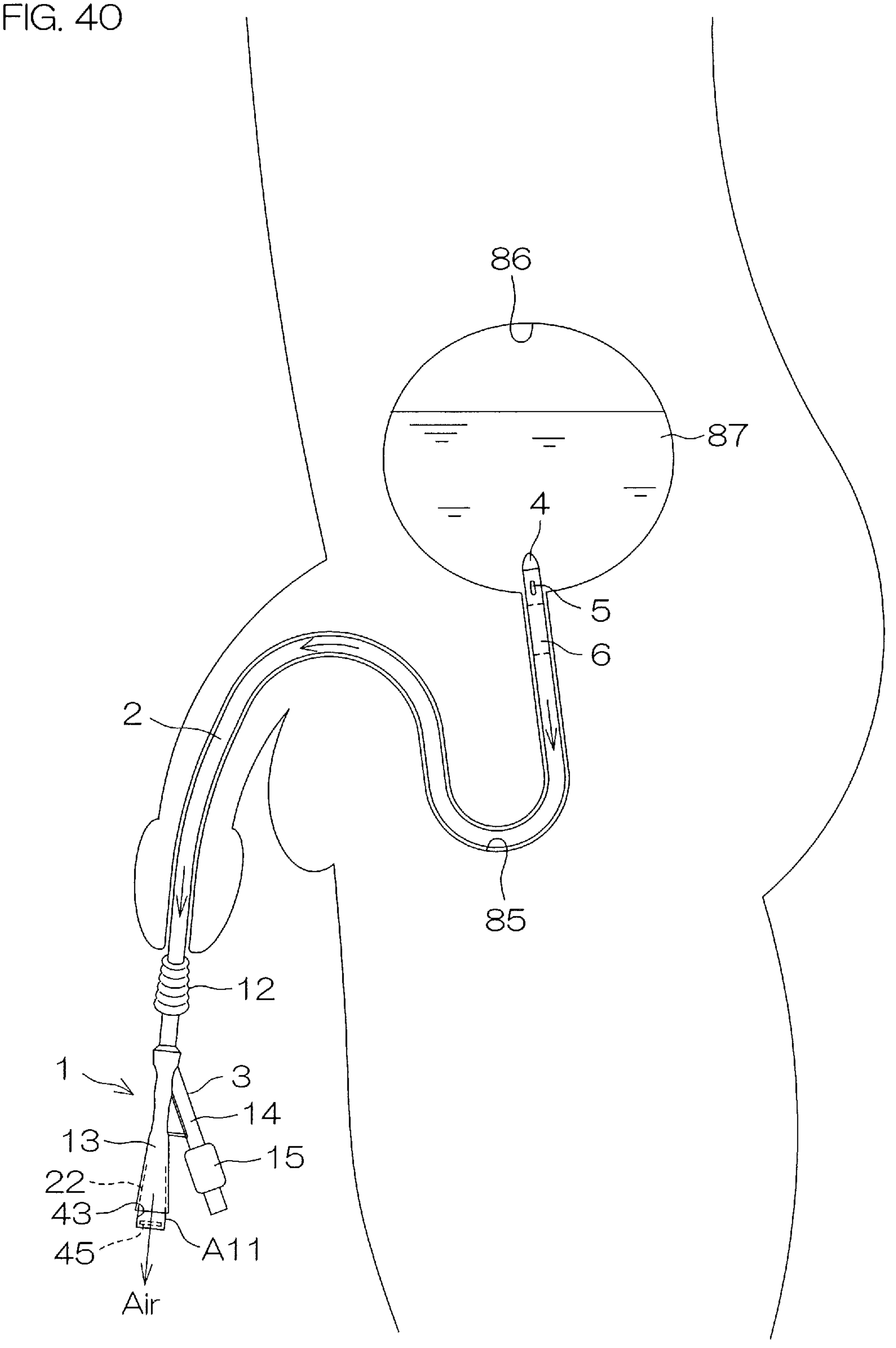
FIG. 40 is a diagram for describing a method for using a catheter.
Figure 41:
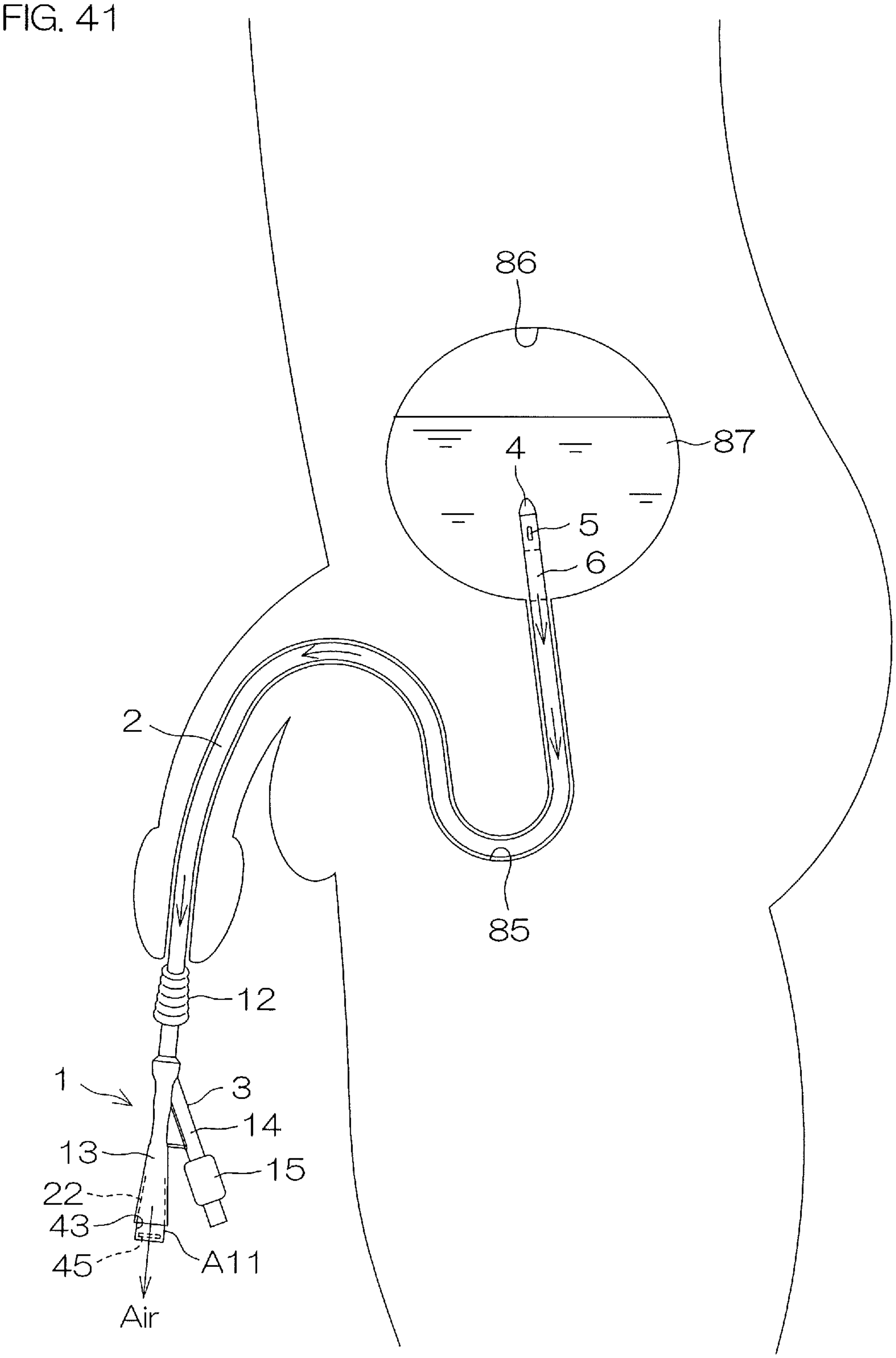
FIG. 41 is a diagram for describing the method for using the catheter.
Figure 42:
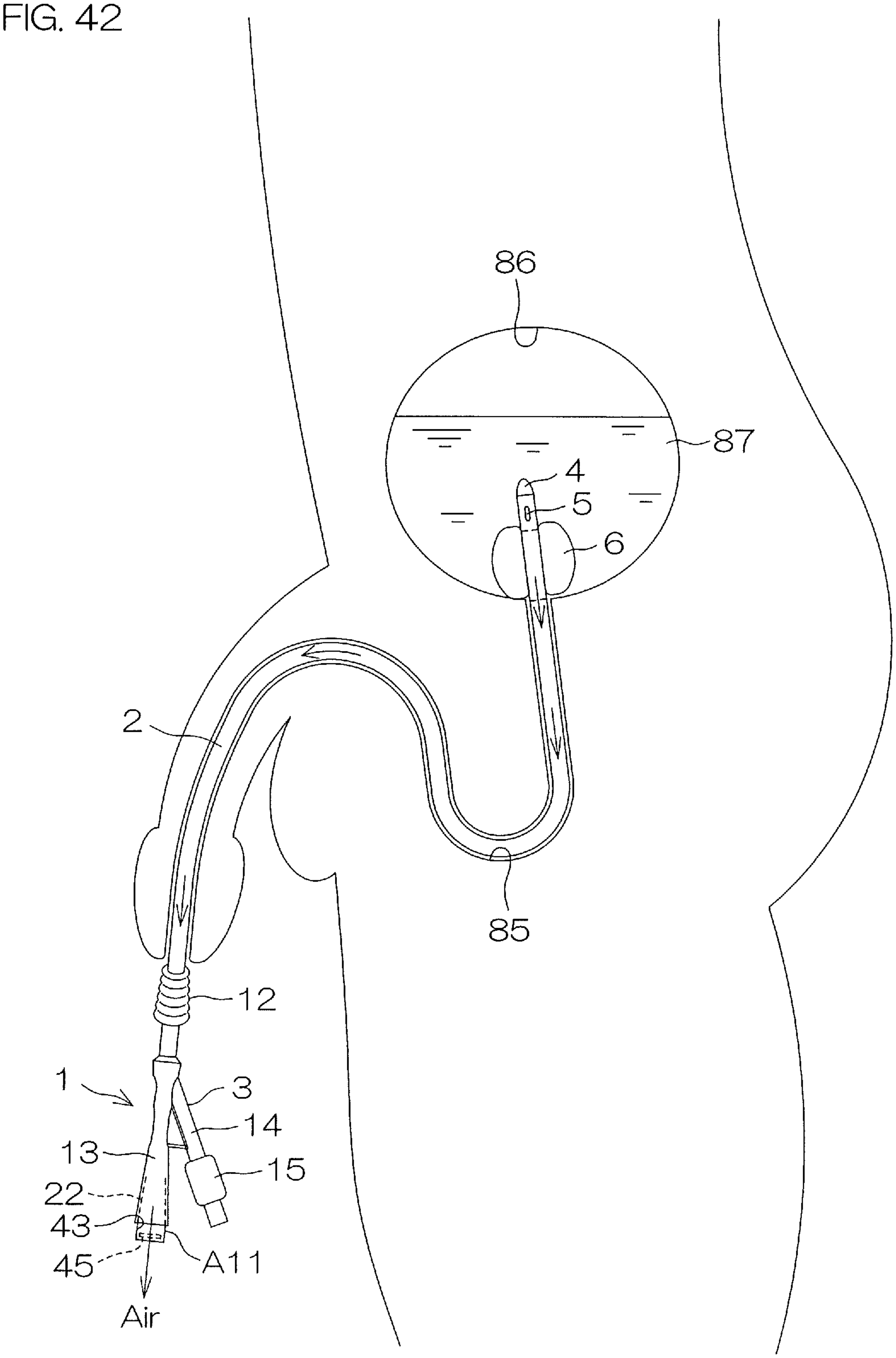
FIG. 42 is a diagram for describing the method for using the catheter.
Figure 43:
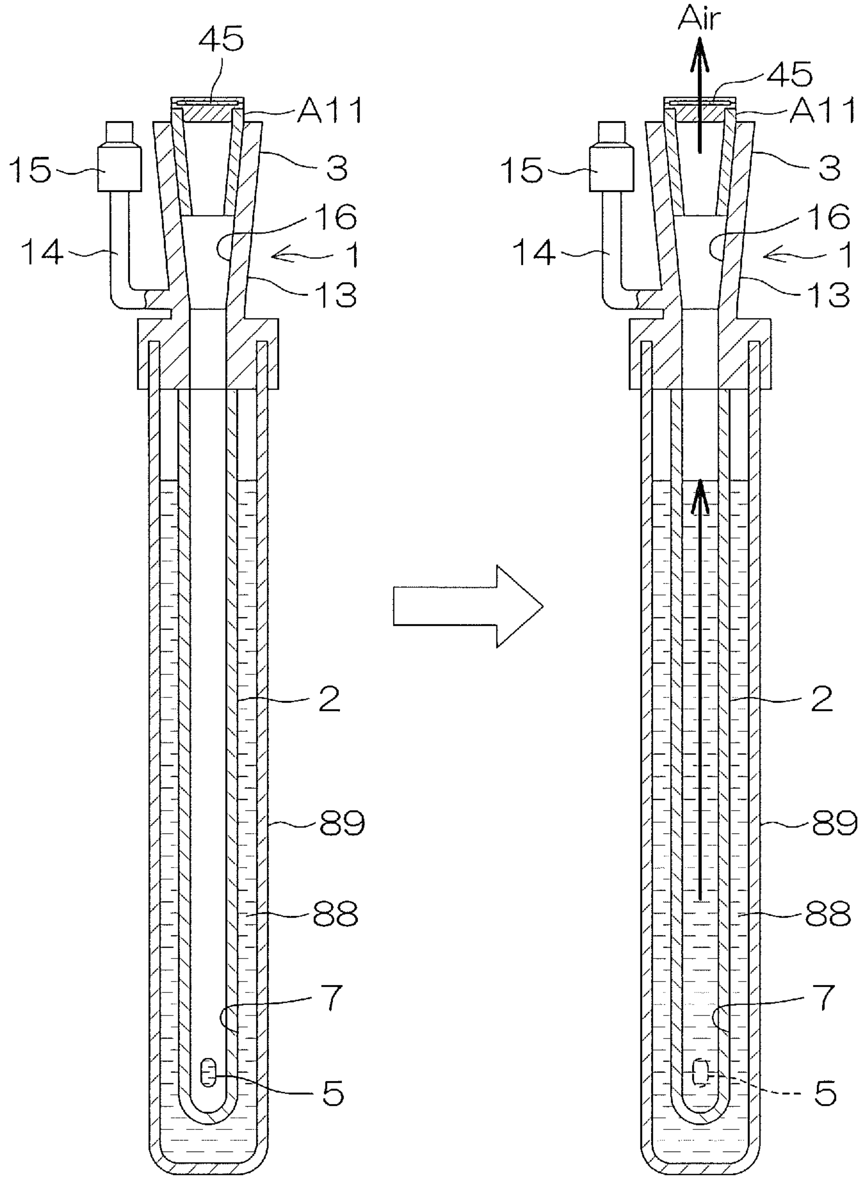
FIG. 43 is a diagram showing states of the catheter during disinfection.

FIG. 40 to FIG. 42 are diagrams for describing, in succession, a method for using the catheter 1. FIG. 43 is a diagram showing states of the catheter 1 during disinfection.

Next, the method for using the catheter 1 and effects due to installation of the caps A1 to A10 according to the preferred embodiments described above shall be described with reference to FIG. 40 to FIG. 43. Here, in FIG. 40 to FIG. 43, the caps A1 to A10 according to the preferred embodiments described above are schematically indicated as a cap A11. Also, although in FIG. 40 to FIG. 42, a method for indwelling catheterization is illustrated as an example, the method for inserting the catheter 1 into a urethra 85 is the same in the case of clean intermittent catheterization (CIC).

For a patient to insert the catheter 1 into the patient's own urethra 85 (to perform self-catheterization), first, the shaft 2 is inserted into the urethra 85 successively from the cap 4 as shown in FIG. 40. In this process, the catheter 1 can be inserted hygienically by inserting the shaft 2 while holding it via the sleeve 12. Then, when the side hole 5 at the tip of the shaft 2 reaches the bladder 86, the urine 87 inside the bladder 86 is guided to the urine withdrawing lumen 7 (see FIG. 2A and FIG. 2B) via the side hole 5. The urine 87 guided to the urine withdrawing lumen 7 moves downstream through the urine withdrawing lumen 7 and reaches the urine introduction passage 22 (not shown) of the cap A11 via the urine drain base 13.

Upon confirming that the urine 87 has reached the cap A11, for example, visually, the patient inserts the catheter 1 slightly further as shown in FIG. 41. The reason for this is that there are cases where even when the side hole 5 of the catheter 1 has reached the interior of the bladder 86, the balloon 6 is positioned inside the urethra 85 as shown in FIG. 40, and there is a possibility of damaging the urethra 85 if the balloon 6 is inflated in this state.

The balloon 6 is thereafter inflated with sterilized water as shown in FIG. 42 by injecting the sterilized water from the balloon base 14. By thereby fixing the balloon 6 inside the bladder 86, the shaft 2 is prevented from slipping out and the catheter 1 is retained inside the bladder 86. Thereafter, the urine 87 stored in the bladder 86 can be drained by connecting a urine collection bag, etc., to the cap A11.

As described above, with each of the caps A1 to A11 described above, the open hole 43, 60, or 64 is formed and the hydrophobic film 45 is formed on the hole 43, 60, or 64. The air inside the catheter 1 can thereby be released to the exterior when inserting the catheter 1 into the urethra 85 and therefore, the urine 87 inside the bladder 86 can be guided smoothly to any of the caps A1 to A11 after the tip of the catheter 1 reaches the bladder 86 (see FIG. 40). On the other hand, the urine 87 that is drained from the bladder 86 is obstructed by the hydrophobic film 45 and the urine 87 can thus be retained in the urine introduction passage 22 of any of the caps A1 to A11. Consequently, a subsequent task can be performed slowly without haste upon confirming that the urine 87 has reached any of the caps A1 to A11.

For example, in performing the indwelling catheterization illustrated in FIG. 40 to FIG. 42, the tasks of confirming the arrival of the urine 87 by the procedure of FIG. 40 and then additionally inserting the catheter 1 as shown in FIG. 41 can be performed calmly. Consequently, the catheter 1 can be inserted calmly to an appropriate position and therefore, positioning of the balloon 6 can be performed satisfactorily. Inflating of the balloon 6 inside the urethra 85 can thereby be prevented. Also, the catheter 1 can be prevented from being inserted excessively inside the bladder 86 as well and therefore, the tip of the catheter 1 can be prevented from contacting the bladder wall and damaging the bladder wall when the bladder 86 contracts during retention of the catheter 1.

On the other hand, there is also a merit to using any of the caps A1 to A11 described above in performing clean intermittent catheterization (CIC). In this case, splashing of the urine 87 can be prevented by confirming the arrival of the urine 87 by the procedure of FIG. 40 and then opening the lid portion 19, 51, 56, 70, 73, or 76 of any of the caps A1 to A11 toward a toilet bowl, etc. Consequently, contamination of surroundings of the toilet bowl, etc., by the urine 87 can be prevented.

Further, after self-catheterization is ended, the catheter 1 must be disinfected by being placed in a case 89 containing a disinfectant solution 88 as shown in FIG. 43. With each of the caps A1 to A11, the air inside the shaft 2 can be released to the exterior via the hydrophobic film 45 even during the disinfection. Consequently, even when it remains installed on the catheter 1, the disinfectant solution 88 can be supplied throughout the interior of the shaft 2 via the side hole 5. Consequently, the catheter 1 can be kept sanitary.

Eleventh Preferred Embodiment

Figure 44:
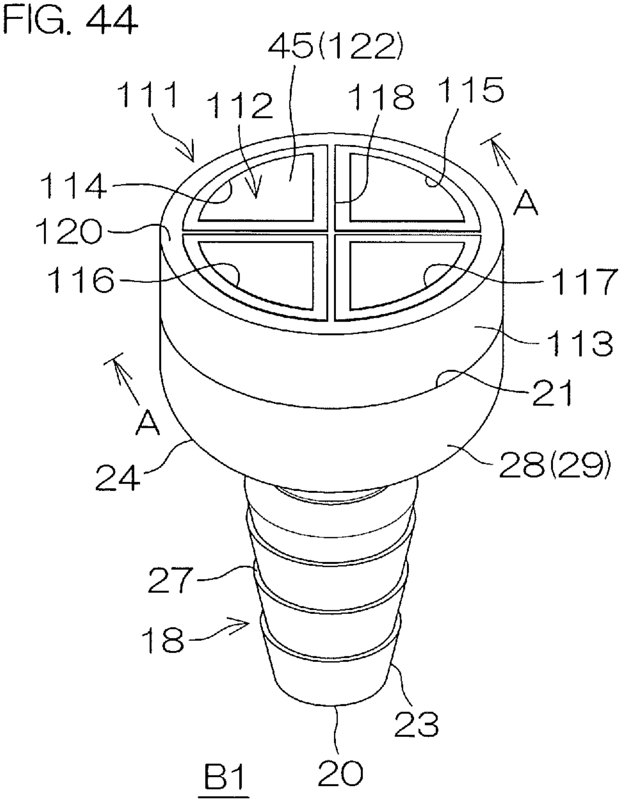
FIG. 44 is a perspective view of a cap according to an eleventh preferred embodiment of the present invention.
Figure 45:
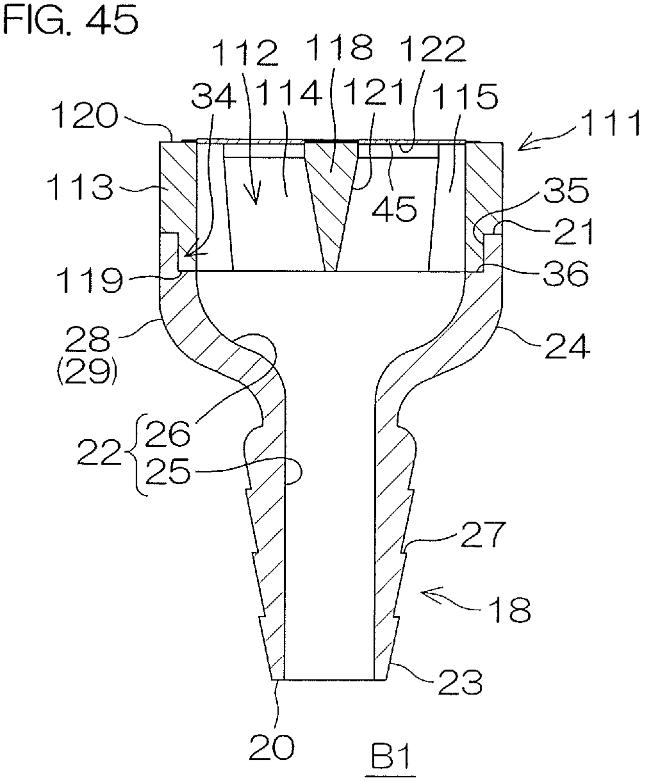
FIG. 45 is a diagram showing a section taken along A-A of FIG. 44.
Figure 46:
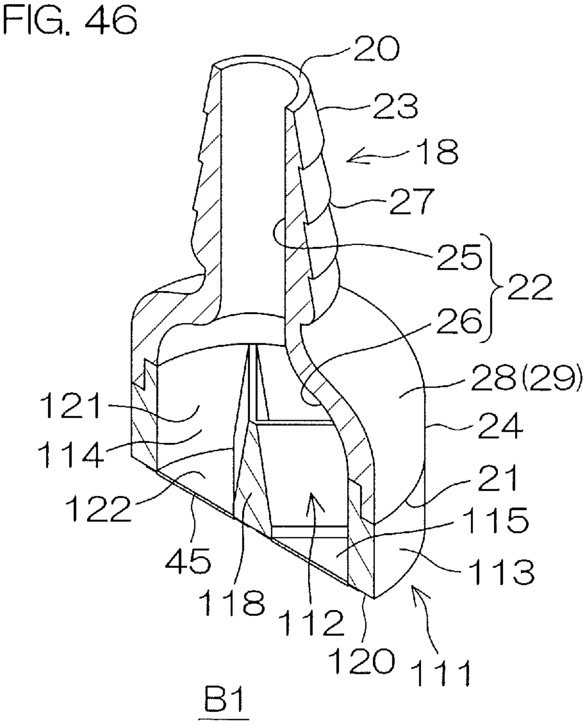
FIG. 46 is a perspective view of the cap of FIG. 45.
Figure 47:
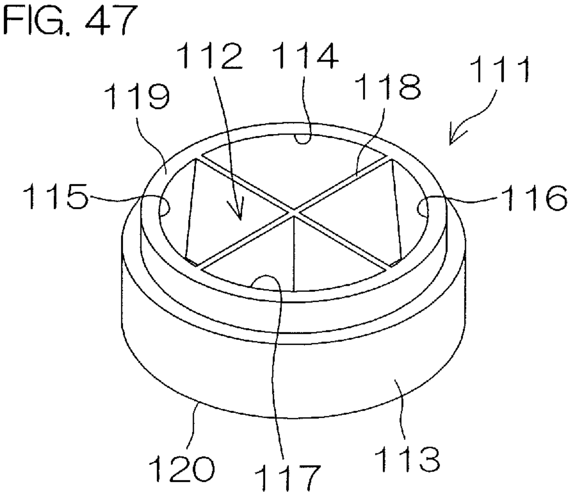
FIG. 47 is a diagram for describing an internal structure of a lid portion of the cap of FIG. 44.

FIG. 44 is a perspective view of a cap B1 according to an eleventh preferred embodiment of the present invention. FIG. 45 is a diagram showing a section taken along A-A of FIG. 44. FIG. 46 is a perspective view of the cap B1 of FIG. 45. FIG. 47 is a diagram for describing an internal structure of a lid portion 111 of the cap B1 of FIG. 44. In FIG. 44 to FIG. 47, a cover member 301 (to be described later) that covers a top surface of the lid portion 111 is omitted from illustration for clarification of features of the cap B1. Also, in FIG. 44 to FIG. 47, arrangements equivalent to arrangements indicated in the preferred embodiments described above shall be provided with the same reference signs and description thereof shall be omitted.

With the cap B1 according to this preferred embodiment, in place of the drain outlet 29 of circular tubular shape in the drain portion 24, the base portion 28 that has a bowl shape also serves as the drain outlet 29. Urine that passes through the connection hole 25 is thus drained via the drain hole 26 formed by an inner wall surface of the base portion 28.

Further, the cap B1 includes, in place of the lid portion 19, the lid portion 111 an interior of which is divided into a plurality of spaces. More specifically, the lid portion 111 includes a base portion 113 and a partition portion 118.

The base portion 113 is formed to a tubular shape that is open at a first end portion 119 and a second end portion 120 and has a space 112 in an interior. The first end portion 119 of the base portion 113 may be an upstream side (connection portion with the main body 18) during urine drainage and the second end portion 120 of the base portion 113 may be a downstream side during urine drainage.

The partition portion 118 divides the space 112 into a plurality of spaces 114 to 117 when the base portion 113 is viewed in an axial direction. The partition portion 118 may include a partitioning plate that is installed between plurality of locations of an inner circumferential surface of the base portion 113. In this preferred embodiment, the partition portion (partitioning plate) 218 includes a partitioning plate with a cross shape and the space 112 is demarcated into the four spaces 114 to 117. Specifically, by the base portion 113 of circular shape in plan view being split by the partition portion 118 with the cross shape, the space 112 is divided equally into four parts and the four spaces 114 to 117 with mutually congruent fan shapes are formed. The four spaces 114 to 117 may include the first space 114, the second space 115, the third space 116, and the fourth space 117. Obviously, the space 112 may instead be demarcated into three spaces by the partition portion 118 being, for example, a partitioning plate with a T shape or may be demarcated into two spaces or five or more spaces.

The hydrophobic film 45 is formed such as to cover at least two or more of the plurality of spaces 114 to 117 at the second end portion 120 of the base portion 113. In this preferred embodiment, the hydrophobic film 45 is formed such as to extend across all of the four spaces 114 to 117. The hydrophobic film 45 is supported by the partition portion 118 with the cross shape. Each of the spaces 114 to 117 is thus closed by the hydrophobic film 45 at a top surface side of the base portion 113. That is, when the cap B1 is turned upside down, the base portion 113 has formed therein the spaces 114 to 117 that are demarcated by side walls 121 constituted of a circumferential wall of the base portion 113 and the partition portion 118 and bottom walls 122 constituted of the hydrophobic film 45. The spaces 114 to 117 may respectively be referred to as a first chamber 114, a second chamber 115, a third chamber 116, and a fourth chamber 117 because the bottom walls 122 are closed by the hydrophobic film 45. Here, with the plurality of spaces 114 to 117, as long as at least two or more of the spaces are covered by the hydrophobic film 45, the remaining spaces do not have to be covered by the hydrophobic film 45. For example, the bottom walls 122 of the first space 114 and the second space 115 may be formed of the hydrophobic film 45 and the bottom walls 122 of the third space 116 and the fourth space 117 may be formed of a plastic material that extends integrally from the second end portion 120 of the base portion 113.

Also, a volume of each of the spaces 114 to 117 is preferably not less than 50% of a volume of the urine withdrawing lumen 7 (see FIG. 2A and FIG. 2B) of the shaft 2. The volume of each of the spaces 114 to 117 can be changed as appropriate, for example, by adjusting a height of the partition portion 118 (partitioning wall).

Next, effects of the cap B1 shall be described. First, as with the caps A1 to A11, the cap B1 is provided with the hydrophobic film 45 and therefore, the air inside the shaft 2 can be released to the exterior via the hydrophobic film 45 during the disinfection of the catheter 1 shown in FIG. 43. Consequently, even when it remains installed on the catheter 1, the disinfectant solution 88 can be supplied throughout the interior of the shaft 2 via the side hole 5.

On the other hand, after the catheter 1 is drawn out from the case 89 for disinfection, the disinfectant solution 88 inside the shaft 2 of the catheter 1 is not drained completely and a portion remains. There are cases where the remaining disinfectant solution 88 flows down into the cap B1 due to gravity. There is thus a possibility for the disinfectant solution 88 to become adhered to the hydrophobic film 45 inside the cap B1 and the hydrophobic film 45 to become clogged. For example, the hydrophobic film 45 tends to become clogged when the disinfectant solution 88 is a liquid that is comparatively viscous such as glycerin with benzalkonium chloride added (glycerin BC solution), etc.

Figure 48:
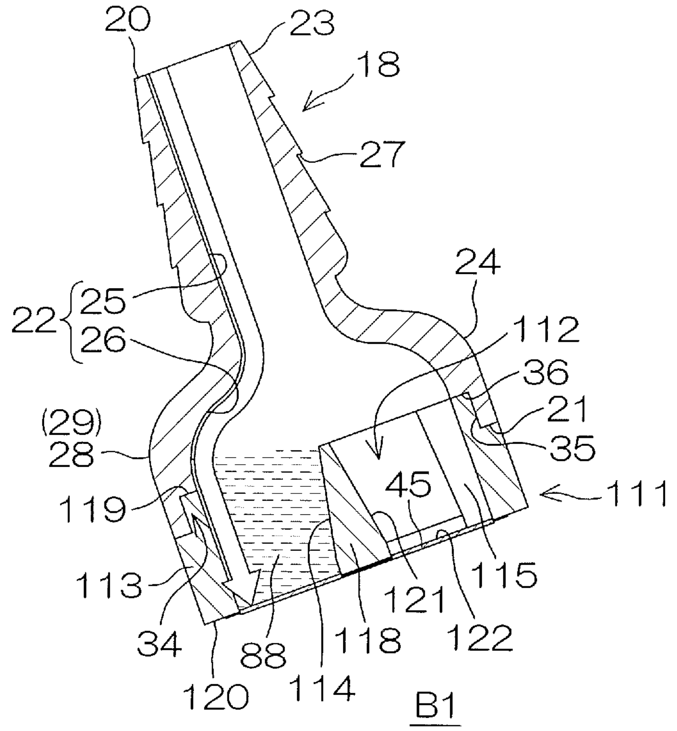
FIG. 48 is a diagram for describing an effect of the cap of FIG. 44.

Thus, with the cap B1, the lid portion 111 is divided into the plurality of spaces 114 to 117 and the bottom wall 122 of each of the spaces 114 to 117 is formed of the hydrophobic film 45. Thereby, even if the disinfectant solution 88 flows down into the cap B1, flowing of the disinfectant solution 88 into all of the spaces 114 to 117 can be avoided, for example, by tilting the cap B1 obliquely as shown in FIG. 48. Consequently, clogging of the hydrophobic film 45 (bottom wall 122) can be avoided in one or some of the spaces 114 to 117 and therefore, air permeability of the hydrophobic film 45 can be secured satisfactorily even after disinfection.

Figure 49:
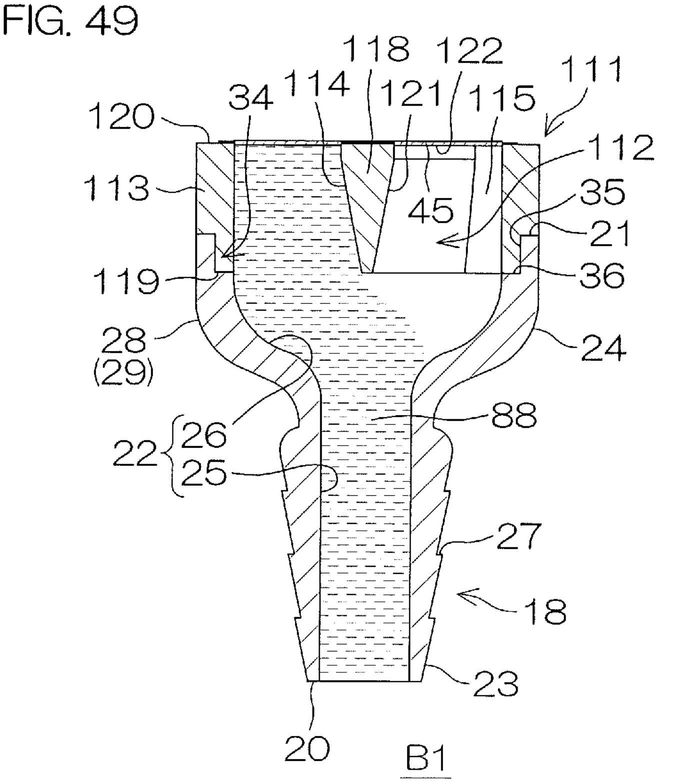
FIG. 49 is a diagram for describing an effect of the cap of FIG. 44.

Also, with the cap B1, the space 112 is divided equally into four parts and the volume of each of the spaces 114 to 117 is comparatively large (for example, in comparison to a cap B2 to be described later). Therefore, even if the disinfectant solution 88 flows into the spaces 114 to 117, influence of surface tension of the disinfectant solution 88 inside the spaces 114 to 117 can be reduced. Consequently, the disinfectant solution 88 inside the spaces 114 to 117 can be eliminated quickly by inverting the cap B1 as shown in FIG. 49.

Twelfth Preferred Embodiment

Figure 50:
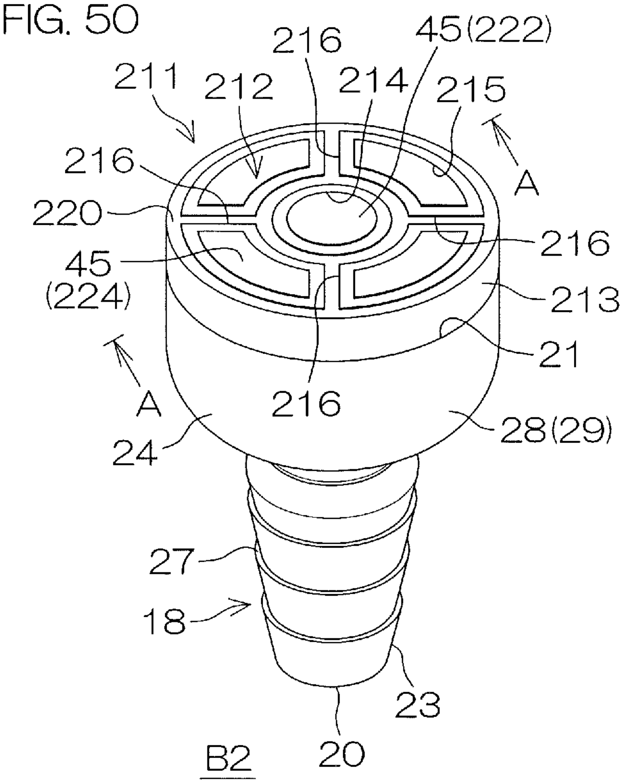
FIG. 50 is a perspective view of a cap according to a twelfth preferred embodiment of the present invention.
Figure 51:
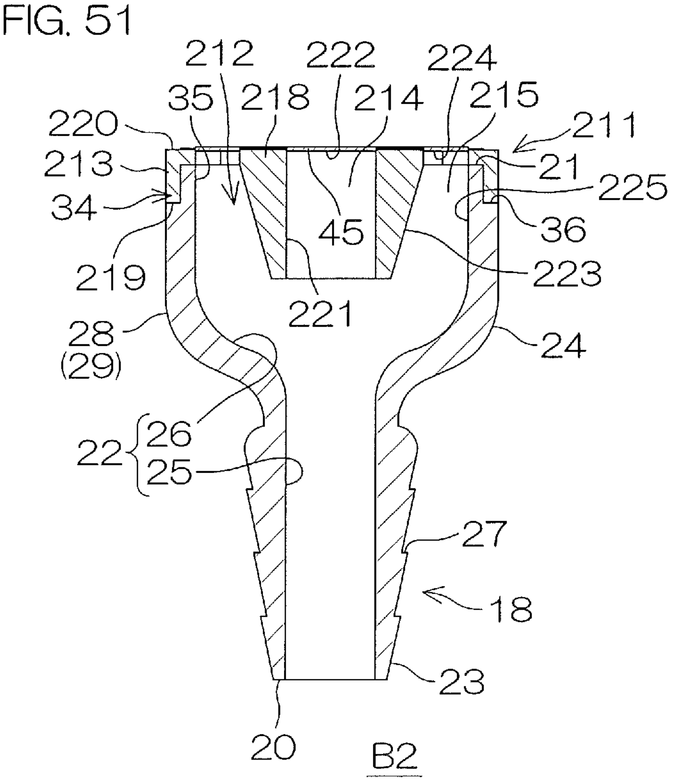
FIG. 51 is a diagram showing a section taken along A-A of FIG. 50.
Figure 52:
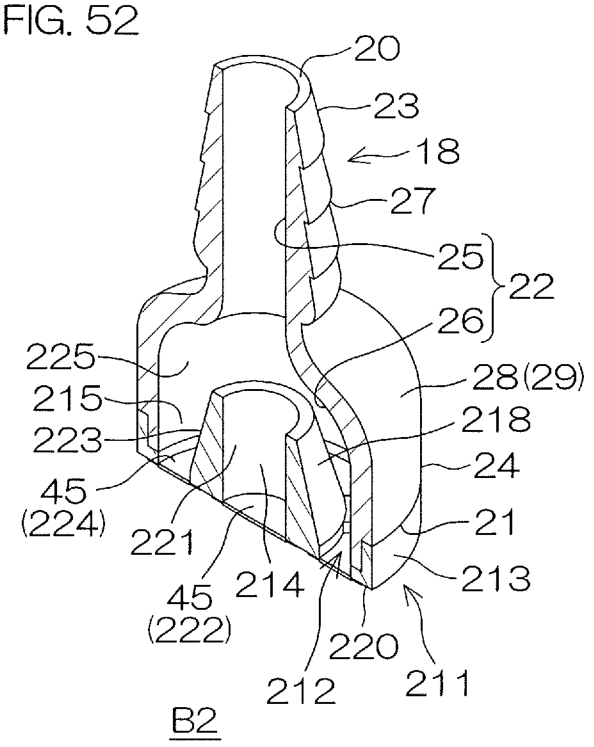
FIG. 52 is a perspective view of the cap of FIG.
Figure 53:
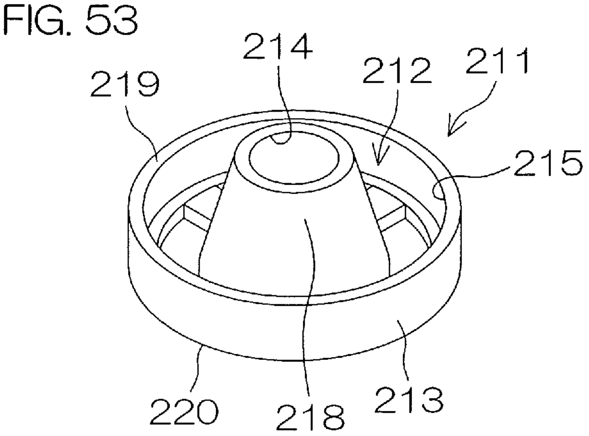
FIG. 53 is a diagram for describing an internal structure of a lid portion of the cap of FIG. 50.

FIG. 50 is a perspective view of a cap B2 according to a twelfth preferred embodiment of the present invention. FIG. 51 is a diagram showing a section taken along A-A of FIG. 50. FIG. 52 is a perspective view of the cap B2 of FIG. 51. FIG. 53 is a diagram for describing an internal structure of a lid portion 211 of the cap B2 of FIG. 50. In FIG. 50 to FIG. 53, the cover member 301 (to be described later) that covers a top surface of the lid portion 211 is omitted from illustration for clarification of features of the cap B2. Also, in FIG. 50 to FIG. 53, arrangements equivalent to arrangements indicated in the preferred embodiments described above shall be provided with the same reference signs and description thereof shall be omitted.

With the cap B2 according to this preferred embodiment, in place of the drain outlet 29 of circular tubular shape in the drain portion 24, the base portion 28 that has a bowl shape also serves as the drain outlet 29. Urine that passes through the connection hole 25 is thus drained via the drain hole 26 formed by the inner wall surface of the base portion 28.

Further, the cap B2 includes, in place of the lid portion 19, the lid portion 211 an interior of which is divided into a plurality of spaces. More specifically, the lid portion 211 includes a base portion 213 and a partition portion 218.

The base portion 213 is formed to a tubular shape that is open at a first end portion 219 and a second end portion 220 and has a space 212 in an interior. The first end portion 219 of the base portion 213 may be an upstream side (connection portion with the main body 18) during urine drainage and the second end portion 220 of the base portion 213 may be a downstream side during urine drainage.

The partition portion 218 divides the space 212 into a plurality of spaces 214 and 215 when the base portion 213 is viewed in an axial direction. The partition portion 218 may include a partitioning tube that is erected in the space 212 and is formed to a tubular shape having an axial direction of the same direction as the axial direction of the base portion 213. As a partitioning tube, the partition portion separates, by a wall portion of tubular shape, a space at an inner side of the wall portion and a space at an outer side of the wall portion into mutually independent spaces. In this preferred embodiment, the partition portion (partitioning tube) 118 includes a partitioning tube with a circular tubular shape and the space 212 is demarcated into the two spaces 214 and 215. Specifically, by the base portion 213 of circular shape in plan view being split by the partition portion 218 with the circular tubular shape, the first space 214 as a circular columnar shape at an inner side of the partition portion 218 and the second space 215 as a circular annular space at an outer side of the partition portion 218 are formed in the space 212. Obviously, the partition portion 218 may, for example, have a quadrilateral tubular shape or have a triangular tubular shape. The partition portion 218 is coupled to the base portion 213 by supporting portions 216 of rectilinear shape that extend toward radially inner sides of the base portion 213 from a circumferential wall of the base portion 213. In this preferred embodiment, four supporting portions 216 that extend in four directions from the partition portion 218 support the partition portion 218.

The hydrophobic film 45 is formed such as to cover the two spaces 214 and 215 at the second end portion 220 of the base portion 213. The hydrophobic film 45 is supported by the partition portion 218 and the supporting portions 216. Each of the spaces 214 and 215 is thus closed by the hydrophobic film 45 at a top surface side of the base portion 213. That is, when the cap B2 is turned upside down, the base portion 213 has formed therein the first space 214 that is demarcated by a side wall 221 constituted of an inner circumferential wall of the partition portion 218 and a bottom wall 222 constituted of the hydrophobic film 45. Also, the second space 215 that is demarcated by a side wall 223 constituted of an outer circumferential wall of the partition portion 218, a side wall 225 constituted of the circumferential wall of the base portion 213, and a bottom wall 224 constituted of the hydrophobic film 45 is formed. The spaces 214 and 215 may respectively be referred to as a first chamber 214 and a second chamber 215 because the bottom walls 222 and 224 are closed by the hydrophobic film 45.

Also, a volume of each of the spaces 214 and 215 is preferably not less than 50% of the volume of the urine withdrawing lumen 7 (see FIG. 2A and FIG. 2B) of the shaft 2. The volume of each of the spaces 214 and 215 can be changed as appropriate, for example, by adjusting a height of the partition portion 218 (partitioning tube).

With the cap B2, the lid portion 211 is divided into the plurality of spaces 214 and 215 and the bottom walls 222 and 224 of the respective spaces 214 and 215 are formed of the hydrophobic film 45. Thereby, even if the disinfectant solution 88 flows down into the cap B2, flowing of the disinfectant solution 88, for example, into the first spaces 214 can be avoided, by tilting the cap B2 obliquely. Consequently, clogging of the hydrophobic film 45 (bottom wall 222) can be avoided in at least the first space 214 and therefore, air permeability of the hydrophobic film 45 can be secured satisfactorily even after disinfection.

Thirteenth Preferred Embodiment

Figure 54:
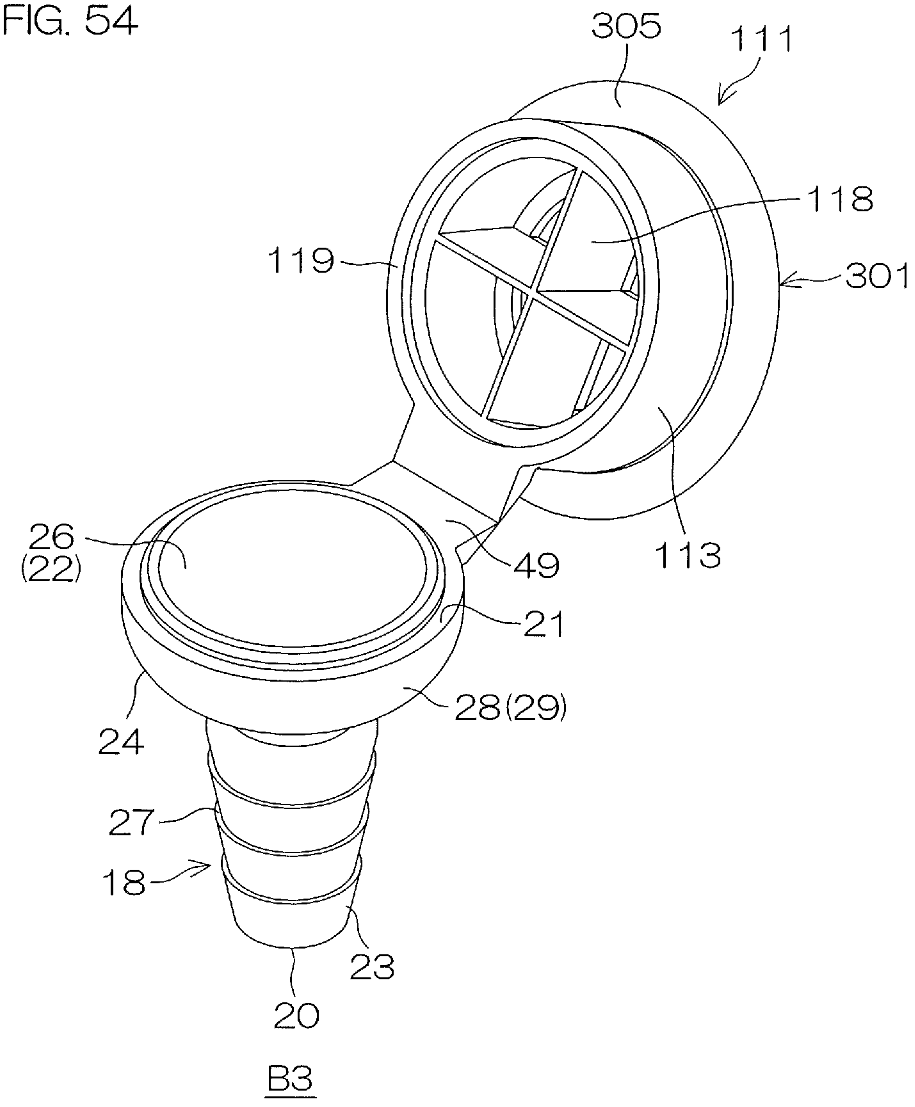
FIG. 54 is a perspective view of a cap according to a thirteenth preferred embodiment of the present invention.
Figure 55:
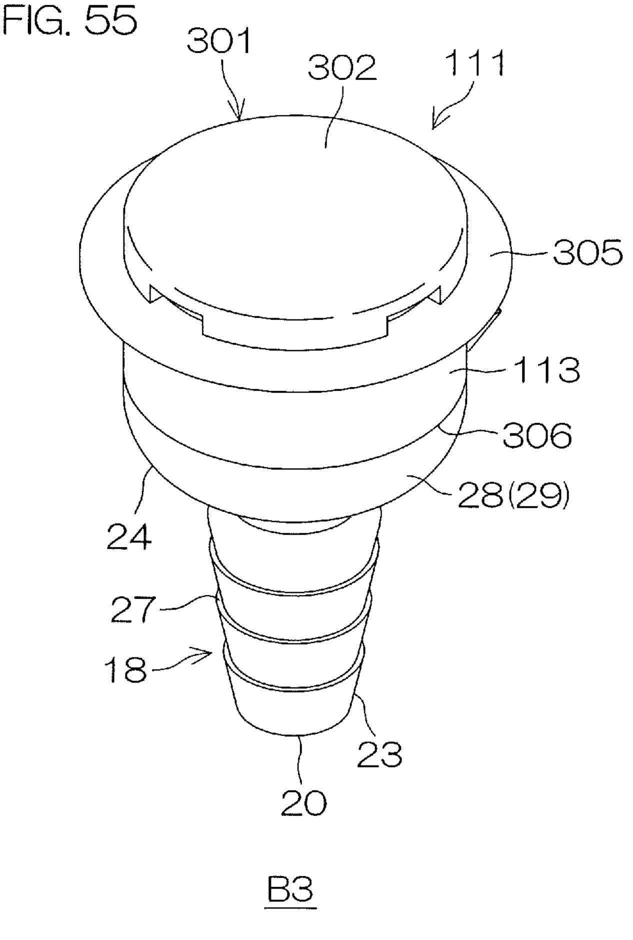
FIG. 55 is a perspective view of the cap according to the thirteenth preferred embodiment of the present invention.
Figure 56:
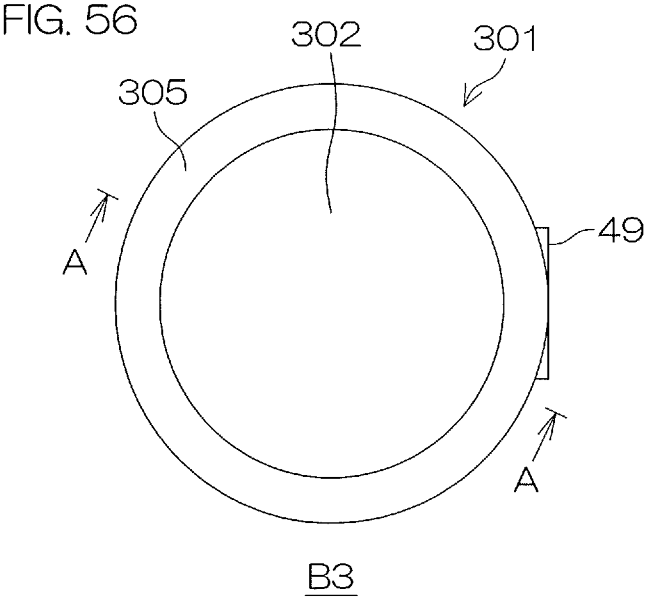
FIG. 56 is a plan view of the cap according to the thirteenth preferred embodiment of the present invention.
Figure 57:
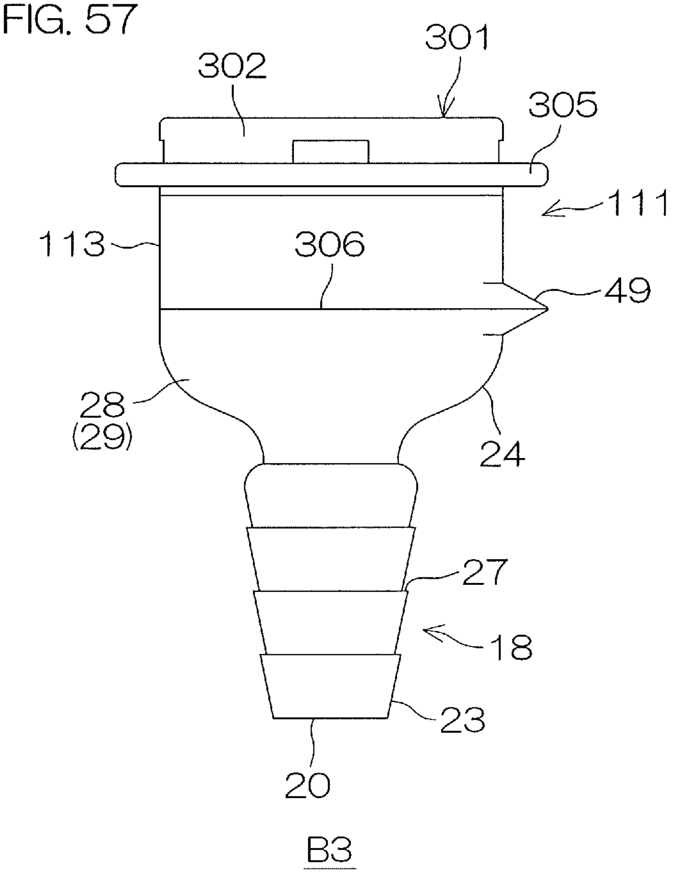
FIG. 57 is a side view of the cap according to the thirteenth preferred embodiment of the present invention.
Figure 58:
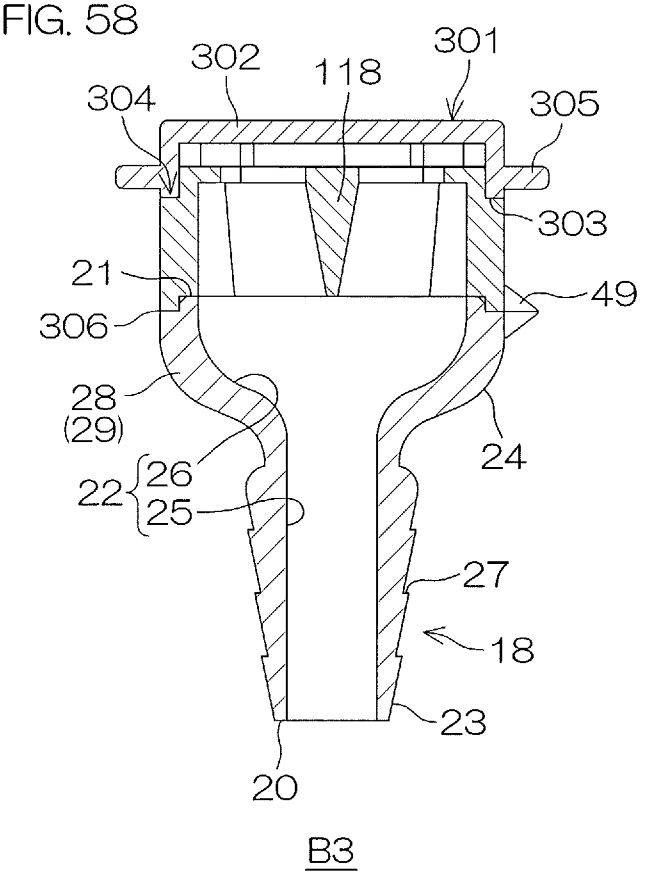
FIG. 58 is a diagram showing a section taken along A-A of FIG. 56.
Figure 59:
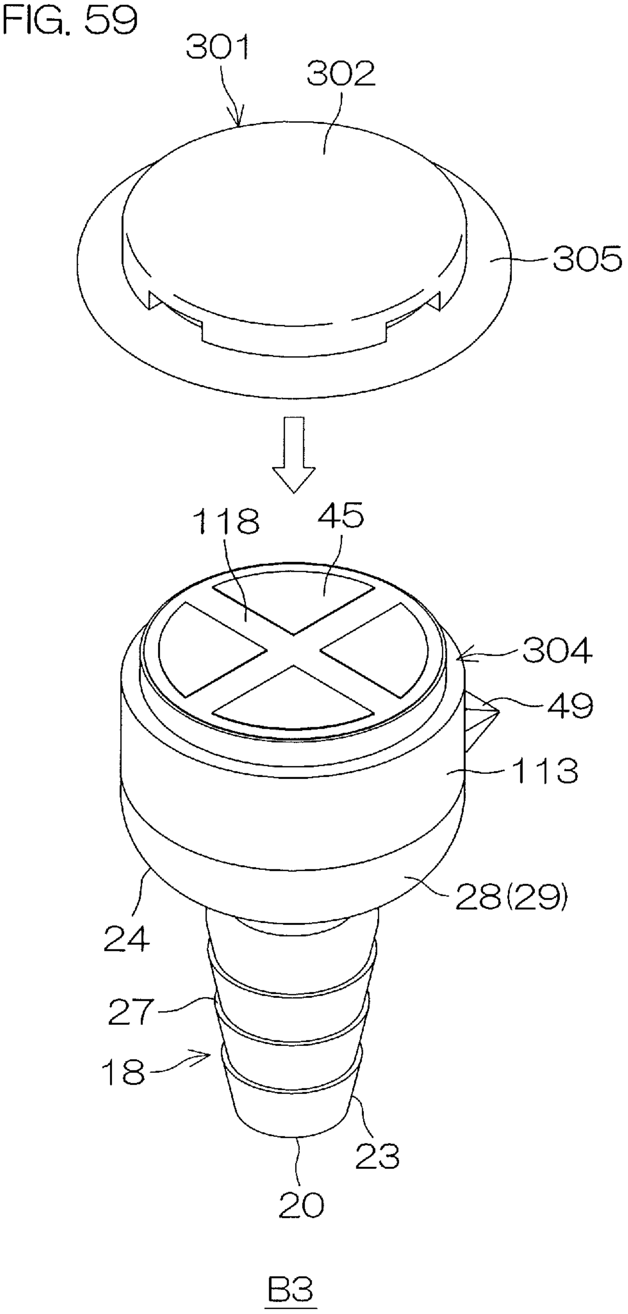
FIG. 59 is an exploded view of the cap according to the thirteenth preferred embodiment of the present invention.

FIG. 54 is a perspective view of a cap B3 according to a thirteenth preferred embodiment of the present invention. FIG. 55 is a perspective view of the cap B3 according to the thirteenth preferred embodiment of the present invention. FIG. 56 is a plan view of the cap B3 according to the thirteenth preferred embodiment of the present invention. FIG. 57 is a side view of the cap B3 according to the thirteenth preferred embodiment of the present invention. FIG. 58 is a diagram showing a section taken along A-A of FIG. 56. FIG. 59 is an exploded view of the cap B3 according to the thirteenth preferred embodiment of the present invention. Also, in FIG. 54 to FIG. 59, arrangements equivalent to arrangements indicated in the preferred embodiments described above shall be provided with the same reference signs and description thereof shall be omitted.

The lid portion 111 of the cap B3 includes a cover member 301 with a cap shape that covers the top surface of the base portion 113. The cover member 301 covers and protects the hydrophobic film 45 and may therefore be referred to as a protective member. The cover member 301 is formed to a circular annular shape having a top wall portion 302. An opposite side to the top wall portion 302 of the cover member 301 is a connection portion 303 that is open.

A recessed groove 304 is formed to a circular shape along an entire circumference in a circumferential direction of the base portion 113 at an outer side surface of the second end portion 120 of the base portion 113. The cover member 301 is affixed to the base portion 113 by the recessed groove 304 and the connection portion 303 being fitted together.

Also, the cover member 301 has a flange portion 305 that projects outward from a portion of circular annular shape. A patient can open the lid portion 111, for example, by setting a thumb against the flange portion 305.

With the cap B3, the flange portion 305 for opening and closing of the lid portion 111 is separated from an opening/closing position 306 (in this preferred embodiment, a connection position of the first end portion 119 of the base portion 113 and the second end portion 21 of the main body 18) of the lid portion 111 of the cap B3. For example, the flange portion 305 is separated from the opening/closing position 306 by a height of the base portion 113. Contact of urine with a hand can thus be avoided when opening the lid portion 111 to drain the urine.

Here, the same effect can also be expressed by a projecting portion that projects selectively outward from a portion of circular annular shape of the cover member 301 in place of the flange portion 305. For example, although in this preferred embodiment, the above effect is expressed by the cover member 301 of a hat shape having the flange portion 305, the same effect can also be expressed by the cover member 301 having a cap shape.

[Variations of the Cover Member 301]

Next, variations of the cover member 301 of the cap B3 shall be described with reference to FIG. 60 to FIG. 68. The cover member 301 may be any of cover members 311, 321, and 331 indicated below. The cover member 301 illustrated in FIG. 54 to FIG. 59 described above may be the cover member 311 instead.

(First Mode)

Figure 60:
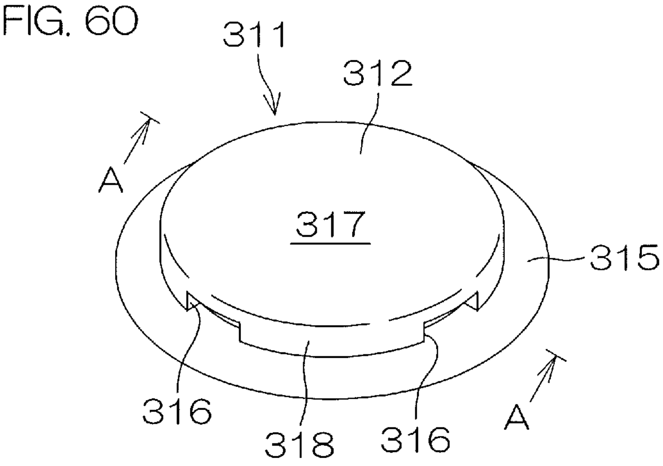
FIG. 60 is a diagram showing a first mode of a cover member of the cap of FIG. 55.
Figure 61:
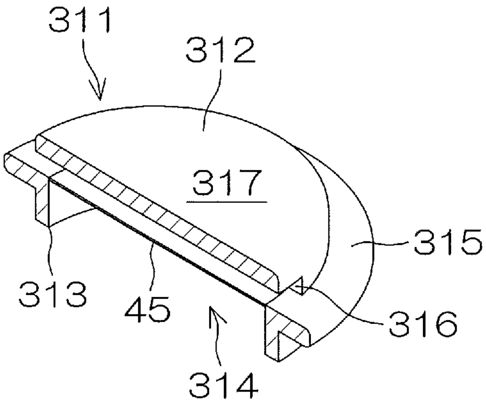
FIG. 61 is a sectional view of a section taken along A-A of FIG. 60.
Figure 62:
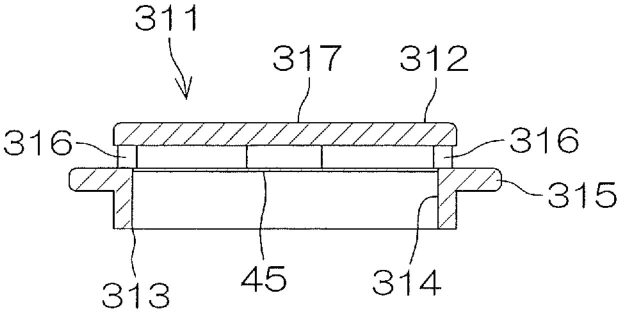
FIG. 62 is a sectional view of the section taken along A-A of FIG. 60.

FIG. 60 is a diagram showing a first mode of the cover member 311 of the cap of FIG. 55. FIG. 61 is a sectional view of a section taken along A-A of FIG. 60. FIG. 62 is a sectional view of the section taken along A-A of FIG. 60.

The cover member 311 is a member that protects the hydrophobic film 45 and secures flow of air inside and outside the cap B3. The cover member 311 is formed to a circular annular shape having a top wall portion 312. An opposite side to the top wall portion 312 of the cover member 311 is a connection portion 313 that is open. The cover member 311 may have a circular tubular shape. The cover member 311 has a space 314 that is closed at one side by the top wall portion 312. The hydrophobic film 45 is housed in the space 314 in a state of being covered by the top wall portion 312.

The cover member 311 includes a flange portion 315 that protrudes outward from its outer circumferential surface. The flange portion 315 is of a circular annular shape that is formed across an entirety of the outer circumferential surface of the cover member 311.

The top wall portion 312 of the cover member 311 has a plain surface without a hole formed on its flat upper surface 317. Here, "plain surface" may mean that an open hole for flow with respect to the space 314 is not formed in the upper surface 317 of the top wall portion 312 and an entirety of the upper surface 317 is constituted of a material constituting the cover member 311.

Flow ports 316 that secure flow of air inside and outside the space 314 are formed in a circumferential surface 318 of the cover member 311. When the cover member 311 is divided into a top wall portion 312 side and a connection portion 313 side with the flange portion 315 as a boundary, the flow ports 316 are formed at the top wall portion 312 side with respect to the flange portion 315. The flow ports 316 are formed in horizontal directions along the upper surface 317 of the top wall portion 312 and may be referred to as lateral holes that form a flow of air in lateral directions. The flow ports 316 are formed in plurality at intervals in a circumferential direction of the cover member 311.

With the cover member 311, the hydrophobic film 45 is housed in the space 314 in an interior of the cover member 311 and therefore, the hydrophobic film 45 cannot be touched directly with a finger, etc. The hydrophobic film 45 can thereby be protected. Further, with the cover member 311, the upper surface 317 of the top wall portion 312 is completely closed and therefore, even if, for example, water contacts the cap B3 during cleaning of the catheter 1, contact of water and the hydrophobic film 45 can be prevented. The hydrophobic film 45 can thereby be protected from water pressure as well.

(Second Mode)

Figure 63:
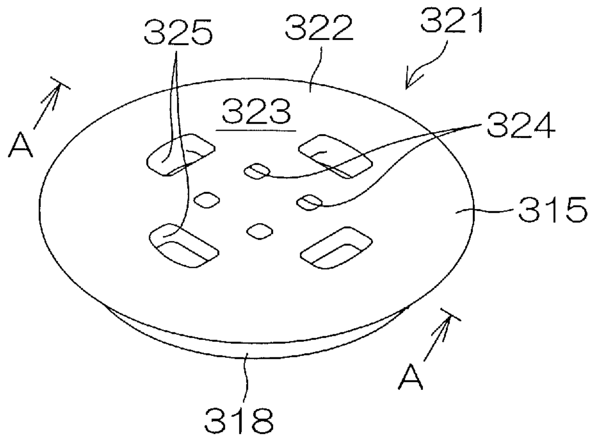
FIG. 63 is a diagram showing a second mode of a cover member of the cap of FIG. 55.
Figure 64:
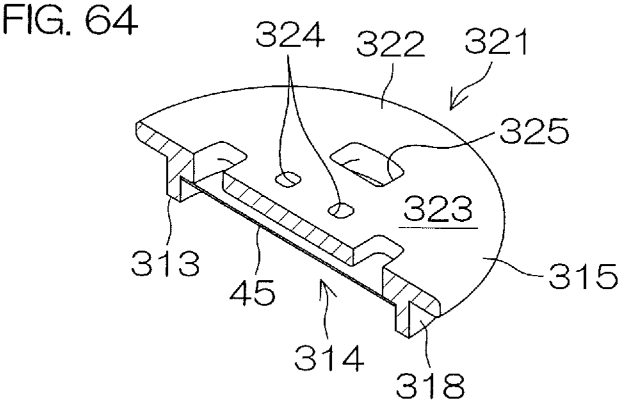
FIG. 64 is a sectional view of a section taken along A-A of FIG. 63.
Figure 65:
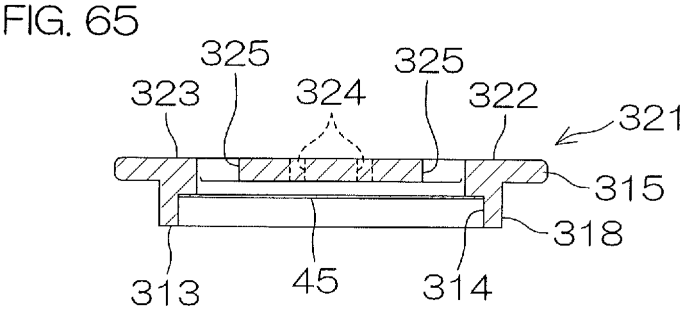
FIG. 65 is a sectional view of the section taken along A-A of FIG. 63.

FIG. 63 is a diagram showing a second mode of a cover member 321 of the cap of FIG. 55. FIG. 64 is a sectional view of a section taken along A-A of FIG. 63. FIG. 65 is a sectional view of the section taken along A-A of FIG. 63. In FIG. 63 to FIG. 65, arrangements equivalent to arrangements of the cover member 311 described above shall be provided with the same reference signs and description thereof shall be omitted.

In place of the top wall portion 312 having the plain surface (upper surface 317), the cover member 321 includes a top wall portion 322 having an upper surface 323 with holes formed therein. A plurality of flow ports 324 and 325 are formed in the upper surface 323. The flow ports 324 and 325 are formed in a vertical direction of penetrating through the top wall portion 322 in a thickness direction and may be referred to as vertical holes that form a flow of air in the vertical direction. The flow ports 324 and 325 may include the first flow ports 324 and the second flow ports 325 that differ mutually in diameter.

The plurality of first flow ports 324 having a relatively small diameter are formed in a central portion of the top wall portion 322. The second flow ports 325 having a relatively larger diameter than the first flow ports 324 may be formed such as to surround the first flow ports 324.

With the cover member 321, the hydrophobic film 45 is housed in the space 314 in an interior of the cover member 321 and therefore, the hydrophobic film 45 cannot be touched directly with a finger, etc. The hydrophobic film 45 can thereby be protected.

(Third Mode)

Figure 66:
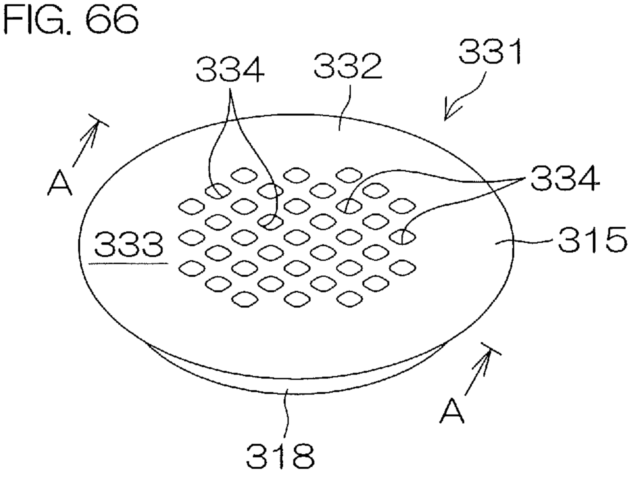
FIG. 66 is a diagram showing a third mode of a cover member of the cap of FIG. 55.
Figure 67:
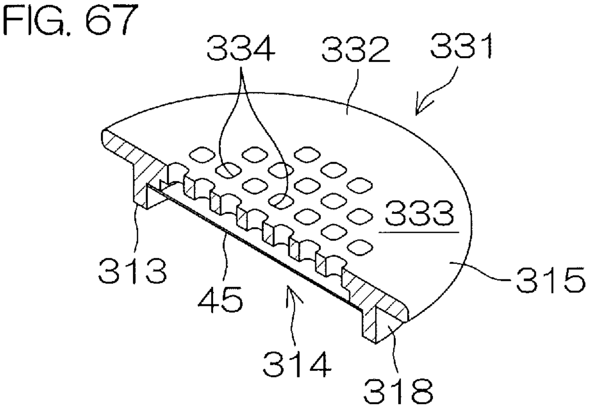
FIG. 67 is a sectional view of a section taken along A-A of FIG. 66.
Figure 68:
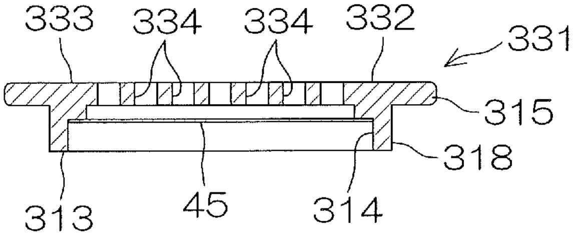
FIG. 68 is a sectional view of the section taken along A-A of FIG. 66.

FIG. 66 is a diagram showing a third mode of a cover member 331 of the cap of FIG. 55. FIG. 67 is a sectional view of a section taken along A-A of FIG. 66. FIG. 68 is a sectional view of the section taken along A-A of FIG. 66. In FIG. 66 to FIG. 68, arrangements equivalent to arrangements of the cover member 311 described above shall be provided with the same reference signs and description thereof shall be omitted.

In place of the top wall portion 312 having the plain surface (upper surface 317), the cover member 331 includes a top wall portion 332 having an upper surface 333 with holes formed therein. A plurality of flow ports 334 are formed in the upper surface 333. The flow ports 334 are formed in a vertical direction of penetrating through the top wall portion 332 in a thickness direction and may be referred to as vertical holes that form a flow of air in the vertical direction. The plurality of flow ports 334 have a mutually equal diameter. The plurality of flow ports 334 are formed in a regular configuration in a central portion of the top wall portion 332.

With the cover member 331, the hydrophobic film 45 is housed in the space 314 in an interior of the cover member 331 and therefore, the hydrophobic film 45 cannot be touched directly with a finger, etc. The hydrophobic film 45 can thereby be protected.

[Performance of the Hydrophobic Film 45]

With the preferred embodiments described above, an example of physical quantities such as the material, the thickness, and the pore diameter, etc., of the hydrophobic film 45 was indicated.

For example, the hydrophobic film 45 may be formed of a known material for hydrophobic film such as polytetrafluoroethylene (PTFE), acrylic copolymer, polyethersulfone (PES), glass fiber, etc. Also, for example, the diameter (pore diameter) of the pores formed in the hydrophobic film 45 may be 0.05 μm to 50 μm. Also, the thickness of the hydrophobic film 45 may be 0.01 mm to 2 mm.

Also, the hydrophobic film 45 is preferably such that its air permeation (Gurley value) measured in conformance to JIS P 8117 (Gurley method) is 0.1 seconds to 500 seconds/100 mL and its water pressure resistance measured in conformance to JIS L 1092-B (high water pressure method) is not less than 0.1 kPa (more preferably 0.1 kPa to 500 kPa).

According to this arrangement, water repellency, air permeability, pressure resistance, and long-term water repellency of the hydrophobic film 45 can be maintained even when any of the caps A1 to A11 and B1 to B3 is used over a long term.

The water repellency is a physical property that indicates, for example, an unlikelihood of the hydrophobic film 45 to be wetted by a disinfectant solution (same as the disinfectant solution 88) (likelihood of repelling the disinfectant solution) when the disinfectant solution is dropped onto the hydrophobic film 45 and can be evaluated visually. For example, if the disinfectant solution that is dropped onto a surface of the hydrophobic film 45 maintains a spherical shape on the surface of the hydrophobic film 45 due to surface tension, it can be said that the water repellency is high.

Also, the long-term water repellency is a physical property that indicates, for example, an unlikelihood of the hydrophobic film 45 to be wetted by the disinfectant solution (likelihood of repelling the disinfectant solution) when the hydrophobic film 45 is contacted with the disinfectant solution for a long time and can be evaluated visually. For example, if after the hydrophobic film 45 is exposed to the disinfectant solution for approximately 1 month, it can be visually confirmed that the surface of the hydrophobic film 45 is not drenched with the disinfectant solution, it can be said that the long-term water repellency is high.

The pressure resistance is a physical property that indicates, for example, an unlikelihood of liquid leakage through the hydrophobic film 45 when a liquid pressure is applied to the hydrophobic film 45 and can be evaluated visually. The following method can be cited as an example of an evaluation method. For example, the catheter 1 with any of the caps A1 to A11 and B1 to B3 mounted thereto is installed in the case 89 containing the disinfectant solution 88. During the installation or, if the case 89 is provided with a bellows structure for collapsing, during collapsing of the case 89, an interior of the case 89 becomes pressurized positively. If, in this process, the disinfectant solution 88 permeates through the hydrophobic film 45 and appears as droplets on an opposite side, it can be said that the pressure resistance is comparatively low. On the other hand, if during the positive pressurization, the disinfectant solution 88 does not appear at the opposite side of the hydrophobic film 45 and the surface of the hydrophobic film 45 is observed to be maintained in a dry state, it can be said that the pressure resistance is high.

The air permeability is a physical property that indicates, for example, whether or not the urine 87 inside the bladder 86 is guided smoothly to any of the caps A1 to A11 and B1 to B3 and can be evaluated visually. For example, if, when the catheter 1 is inserted into one's own urethra 85, urine reaches any of the caps A1 to A11 and B1 to B3 such as to flow continuously from the bladder 86, it can be said that the air permeability is high. On the other hand, if the urine reaches any of the caps A1 to A11 and B1 to B3 but the flow is of an intermittently dripping state, it can be said that the air permeability is not high.

And when the hydrophobic film 45 having the thickness of 10 μm to 2 mm, the air permeation of 0.1 seconds to 500 seconds/100 mL, and the pressure resistance of not less than 0.1 kPa was mounted on a cap (that may be any of the caps A1 to A11 and B1 to B3) and use of the catheter 1 and disinfection were repeated, it could be confirmed that the water repellency, the air permeability, the pressure resistance, and the long-term water repellency can be maintained even upon elapse of two months or more.

Although the preferred embodiments of the present invention have been described above, the present invention can also be implemented in other modes.

For example, with the caps A1 to A11 and B1 to B3 of the preferred embodiments described above, the arrival of urine to the caps A1 to A11 and B1 to B3 can be easily confirmed visually by forming the caps A1 to A11 and B1 to B3 from a translucent resin, making a substance having a function of generating color by action of water be contained in the material of the caps A1 to A11 and B1 to B3, or forming an embossment on the urine introduction passage 22.

Figure 69:
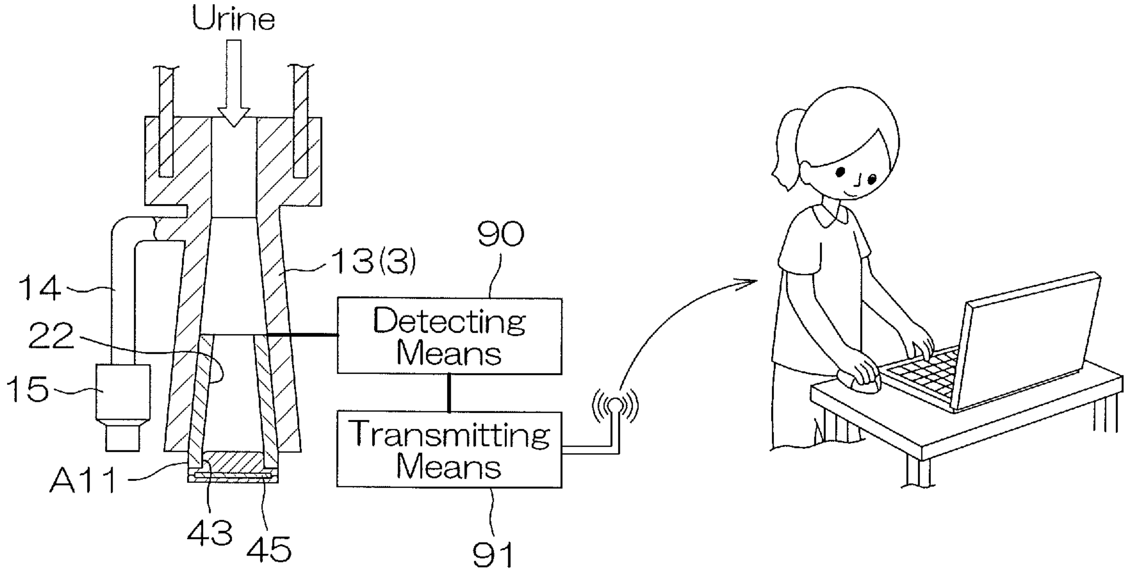
FIG. 69 is a diagram showing a modification example of the cap.

In place of or in addition to such features, any of the caps A1 to A11 and B1 to B3 may be provided with a detecting means 90 and a transmitting means 91 as shown for example in FIG. 69. The detecting means 90 may be a device (for example, an optical device such as a photo-interrupter) that can detect the arrival of urine without contact with the urine. Also, the transmitting means 91 suffices to be that which can transmit arrival information of the urine based on detection by the detecting means 90. For example, the transmitting means 91 may be a wireless communication device that wirelessly transmits the arrival information of the urine 87 to a tablet or other mobile terminal or a personal computer.

By thus including the detecting means 90 and the transmitting means 91, various information can be obtained in accordance with the type of the transmitting means 91. For example, if the transmitting means 91 is a sound generating means, the arrival of urine can be easily confirmed aurally, and if the transmitting means 91 is a vibrating means, the arrival of urine can be easily confirmed by skin sensation. Also, if the transmitting means 91 is a wireless transmitting means, a medical staff or the patient him/herself can indirectly obtain objective information on whether or not the catheter 1 is inserted correctly.

Figure 70:
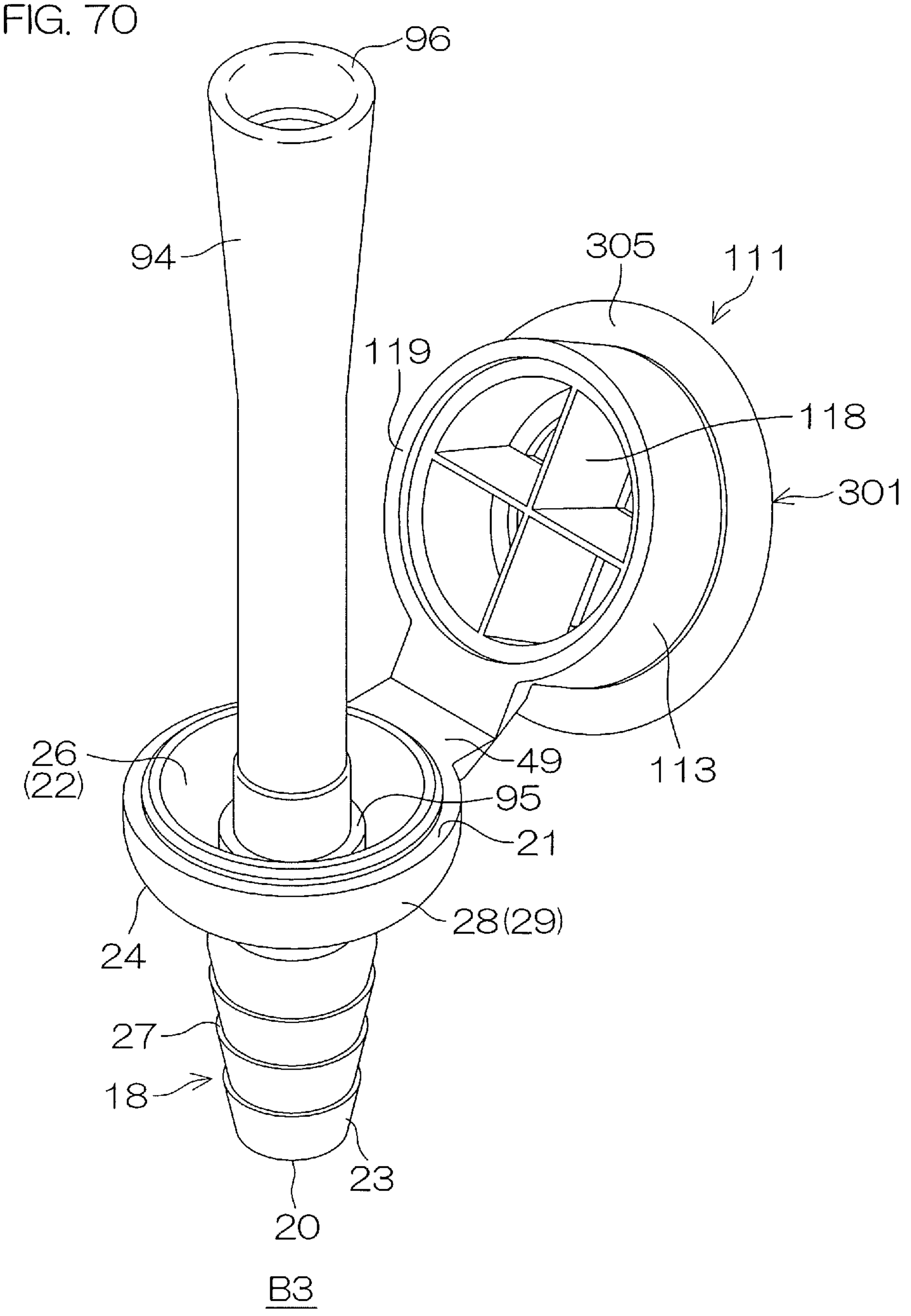
FIG. 70 is a diagram showing an example of a method for using the cap.

Also, an extension attachment 94 may be connected to the connection hole 25 of the main body 18 as shown in FIG. 70. The extension attachment 94 is formed to a tubular shape having a connection side end portion 95 that is connected to the connection hole 25 and a drain side end portion 96 at the opposite side. The extension attachment 94 is formed to a tapered shape that gradually widens in diameter toward the drain side end portion 96. The extension attachment 94 extends the urine introduction passage 22 and enables connection of the urine collection bag with any of the caps A1 to A11 and B1 to B3 remaining installed.

In addition, various design modifications can be applied within the scope of matters described in the claims.

The present application corresponds to Japanese Patent Application No. 2020-076920 filed on Apr. 23, 2020 in the Japan Patent Office, and the entire disclosure of this application is incorporated herein by reference.

REFERENCE SIGNS LIST

1: catheter
2: shaft
3: base
4: cap
5: side hole
6: balloon
7: urine withdrawing lumen
8: balloon lumen
9: circumferential surface
10: rib
11: boundary

12: sleeve
13: urine drain base
14: balloon base
15: check valve
16: urine introduction passage
17: water introduction passage
18: main body
19: lid portion
20: first end portion
21: second end portion
22: urine introduction passage
23: connection portion
24: drain portion
25: connection hole
26: drain hole
27: step portion
28: base portion
29: drain outlet
30: first surface
31: second surface
32: first portion
33: second portion
34: step portion
35: side surface
36: bottom surface
37: projecting ridge
38: curved portion
39: base portion
40: plug portion
41: flange portion
42: recessed groove
43: open hole
44: film placement portion
45: hydrophobic film
46: cover member
47: recess portion
48: flow port
49: hinge mechanism
50: string
51: lid portion
52: screw thread
53: projecting ridge
54: anti-slip structure
55: screw thread
56: lid portion
57: base portion
58: plug portion
59: outer circumferential portion
60: open hole
61: film placement portion
62: cover member
63: flow port
64: open hole
65: film placement portion
66: supporting body
67: film placement portion
68: cover member
69: flow port
70: lid portion
71: slit
72: valve element
73: lid portion
74: inclining valve element
75: slit
76: lid portion
77: plug portion
78: columnar portion
79: projecting ridge
80: anti-slip structure
81: first engaging portion
82: second engaging portion
83: film placement portion
84: film placement portion
85: urethra
86: bladder
87: urine
88: disinfectant solution
89: case
90: detecting means
91: transmitting means
111: lid portion
112: space
113: base portion
114: first space
115: second space
116: third space
117: fourth space
118: partition potion
119: (base portion) first end portion
120: (base portion) second end portion
121: (space) side wall
122: (space) bottom wall
211: lid portion
212: space
213: base portion
214: first space
215: second space
216: supporting portion
218: partition portion
219: (base portion) first end portion
220: (base portion) second end portion
221: (space) side wall
222: (space) bottom wall
223: (space) side wall
224: (space) bottom wall
225: (space) side wall
301: cover member
302: top wall portion
303: connection portion
304: recessed groove
305: flange portion
306: opening/closing position
311: cover member
312: top wall portion
313: connection portion
314: space
315: flange portion
316: flow port
317: (top wall portion) upper surface
318: (cover member) circumferential surface
321: cover member
322: top wall portion
323: (top wall portion) upper surface
324: first flow port
325: second flow port
331: cover member
332: top wall portion
333: (top wall portion) upper surface
334: flow port
A1: cap
A2: cap
A3: cap
A4: cap
A5: cap A6: cap
A7: cap
A8: cap
A9: cap
A10: cap
A11: cap
B1: cap
B2: cap
B3: cap

The invention claimed is:

1. A urinary catheter cap comprising:

a main body that includes a urine introduction passage including a connection hole configured to be connected to a urinary catheter and a drain hole for draining urine;

a lid portion that has a tubular portion having a first end portion at the drain hole side and a second end portion at an opposite side and opens and closes the drain hole;

a partitioning plate disposed inside the tubular portion of the lid portion and that divides the tubular portion of the lid portion into a plurality of spaces; and a hydrophobic film configured to block at least two or more of the spaces at the second end portion of the lid portion, wherein the hydrophobic film is disposed at a distal end and downstream of the partitioning plate in a urine flow direction.

2. The urinary catheter cap according to claim 1, wherein the partitioning plate has a cross shape such that the tubular portion of the lid portion is demarcated into four spaces by the partitioning plate, and the hydrophobic film is formed such that the hydrophobic film extends across all of the four spaces.

3. The urinary catheter cap according to claim 2, wherein the four spaces have mutually congruent fan shapes.

4. The urinary catheter cap according to claim 2, wherein the hydrophobic film is supported by the partition plate with the cross shape.

5. The urinary catheter cap according to claim 1, wherein the lid portion includes a cover member that is formed at the second end portion of the tubular portion of the lid portion such that the cover member covers the hydrophobic film, and the cover member has a projecting portion that projects outward from a side wall thereof.

6. The urinary catheter cap according to claim 5, wherein the projecting portion projects selectively outward from a part of the side wall of the cover member, and the cover member is in a shape of a cap.

7. The urinary catheter cap according to claim 5, wherein the projecting portion includes a flange portion with an annular shape that is formed across an entire outer circumference of the cover member.

8. The urinary catheter cap according to claim 5, wherein the cover member includes a top wall portion that covers the hydrophobic film and has an upper surface constituted of a plain surface without holes formed therein and a flow port that secures flow of air inside and outside the cover member in a lateral direction along the upper surface of the top wall portion is formed in a side wall of the cover member.

9. The urinary catheter cap according to claim 5, wherein the cover member is provided such that the hydrophobic film is accommodated inside, and the hydrophobic film is fixed between the cover member and the lid portion.

10. The urinary catheter cap according to claim 1, wherein the lid portion is openably and closably coupled to the main body via a hinge mechanism.

11. The urinary catheter cap according to claim 1, wherein the main body is formed of a material that contains a substance with antibacterial action.

12. The urinary catheter cap according to claim 1, wherein the main body is formed of a translucent material that contains a substance configured to generate color upon contact with water.

13. The urinary catheter cap according to claim 1, wherein an embossment is formed on an inner surface of the urine introduction passage of the main body.

14. The urinary catheter cap according to claim 1, further comprising:

a detecting device that detects a presence of urine at the urine introduction passage; and a transmitting device that transmits information relating to the presence of the urine based on detection by the detecting device.

15. The urinary catheter cap according to claim 1, wherein the hydrophobic film is formed of a material that contains an ammonia degrading enzyme.

16. The urinary catheter cap according to claim 1, wherein the hydrophobic film contains an acidic agent.

17. The urinary catheter cap according to claim 1, wherein the hydrophobic film has a thickness of 0.01 mm to 2 mm and its air permeation (Gurley value) measured in conformance to JIS P 8117 (Gurley method) is 0.1 seconds to 500 seconds/100 mL and its water pressure resistance measured in conformance to JIS L 1092-B (high water pressure method) is not less than 0.1 kPa.

18. A urinary catheter cap comprising:

a main body that includes a urine introduction passage including a connection hole configured to be connected to a urinary catheter and a drain hole for draining urine;

a lid portion that opens and closes the drain hole;

an open hole that is formed in the main body or the lid portion and faces the urine introduction passage;

a hydrophobic film configured to block the open hole via a film placement portion; and a cover member provided such that the film placement portion and the hydrophobic film are accommodated inside, the hydrophobic film being fixed between the cover member and the lid portion, wherein the hydrophobic film is disposed at a distal end and downstream of the open hole in a urine flow direction.

19. The urinary catheter cap according to claim 18, wherein the open hole is formed in the lid portion.

20. The urinary catheter cap according to claim 19, wherein the lid portion is openably and closably coupled to the main body via a hinge mechanism and the lid portion has a plug portion with a tubular shape that is inserted into the drain hole and has the open hole formed therein.

21. The urinary catheter cap according to claim 19, wherein the lid portion includes a lid portion of a screw type that is detachable from the main body.

22. The urinary catheter cap according to claim 18, wherein the open hole is formed such that the open hole is connected to an intermediate portion of the urine introduction passage of the main body in a flow direction of urine.

23. The urinary catheter cap according to claim 18, wherein the main body is formed of a material that contains a substance with antibacterial action.

24. The urinary catheter cap according to claim 18, wherein the drain hole has a curved shape and a diameter that increases toward an open end of the drain hole.

25. The urinary catheter cap according to claim 18, wherein the main body is formed of a translucent material that contains a substance configured to generate color upon contact with water.

26. The urinary catheter cap according to claim 18, wherein an embossment is formed on an inner surface of the urine introduction passage of the main body.

27. The urinary catheter cap according to claim 18, further comprising:

a detecting device that detects a presence of urine at the urine introduction passage; and a transmitting device that transmits information relating to the presence of the urine based on detection by the detecting device.

28. The urinary catheter cap according to claim 18, wherein the hydrophobic film is formed of a material that contains an ammonia degrading enzyme.

29. The urinary catheter cap according to claim 18, wherein the hydrophobic film contains an acidic agent.

* * * * *